United States Patent
Ishii et al.

(10) Patent No.: US 9,855,546 B2
(45) Date of Patent: Jan. 2, 2018

(54) COMPOSITE OXIDE CATALYST AND METHOD FOR PRODUCING THE SAME

(75) Inventors: Yusuke Ishii, Tokyo (JP); Takaaki Kato, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 365 days.

(21) Appl. No.: 13/992,031

(22) PCT Filed: Dec. 27, 2011

(86) PCT No.: PCT/JP2011/080152
§ 371 (c)(1),
(2), (4) Date: Jun. 6, 2013

(87) PCT Pub. No.: WO2012/090979
PCT Pub. Date: Jul. 5, 2012

(65) Prior Publication Data
US 2013/0253217 A1 Sep. 26, 2013

(30) Foreign Application Priority Data
Dec. 27, 2010 (JP) .................................. 2010-290711

(51) Int. Cl.
| | | |
|---|---|---|
| *B01J 23/30* | (2006.01) | |
| *C07C 253/24* | (2006.01) | |
| *B01J 23/00* | (2006.01) | |
| *B01J 23/28* | (2006.01) | |
| *B01J 35/10* | (2006.01) | |
| *B01J 37/08* | (2006.01) | |
| *C07C 51/215* | (2006.01) | |

(52) U.S. Cl.
CPC ............. *B01J 23/30* (2013.01); *B01J 23/002* (2013.01); *B01J 23/28* (2013.01); *B01J 35/1009* (2013.01); *B01J 35/1014* (2013.01); *B01J 37/08* (2013.01); *C07C 51/215* (2013.01); *C07C 253/24* (2013.01); *B01J 2523/00* (2013.01); *Y02P 20/52* (2015.11)

(58) Field of Classification Search
CPC combination set(s) only.
See application file for complete search history.

(56) References Cited

U.S. PATENT DOCUMENTS

| | | | |
|---|---|---|---|
| 2006/0235238 A1 | 10/2006 | Komada et al. | |
| 2010/0240921 A1 | 9/2010 | Tateno et al. | |
| 2010/0286432 A1* | 11/2010 | Tateno | ................... B01J 23/002 |
| | | | 558/330 |
| 2015/0231604 A1* | 8/2015 | Ishii | ....................... B01J 23/002 |
| | | | 558/321 |

FOREIGN PATENT DOCUMENTS

| | | | |
|---|---|---|---|
| EP | 2392399 A1 | 12/2011 | |
| EP | 2 636 451 A1 | 9/2013 | |
| JP | 2003-320248 A | 11/2003 | |
| JP | 2007-216212 A | 8/2007 | |
| JP | 2007-326036 A | 12/2007 | |
| JP | 2007326036 A * | 12/2007 | ............. B01J 23/28 |
| JP | 2009-262146 A | 11/2009 | |
| TW | 200800384 A | 1/2008 | |
| WO | WO 2004/108278 A1 | 12/2004 | |
| WO | WO 2009/081758 A1 | 7/2009 | |
| WO | WO 2010/087262 A1 | 8/2010 | |

OTHER PUBLICATIONS

European Search Report, dated Oct. 17, 2013, for European Application No. 11853903.0.
International Search Report, issued in PCT/JP2011/080152, dated Feb. 7, 2012.

* cited by examiner

*Primary Examiner* — Joseph R Kosack
(74) *Attorney, Agent, or Firm* — Birch, Stewart, Kolasch & Birch, LLP

(57) ABSTRACT

A method for producing a complex oxide catalyst containing a complex oxide represented by the formula:

$$Mo_1V_aSb_bNb_cW_dZ_eO_n$$

(wherein a component Z represents an element such as La, Ce, Pr, Yb, Y, Sc, Sr, and Ba; a, b, c, d, e, and n each represent an atomic ratio of an element to one Mo atom; $0.1 \leq a \leq 0.4$, $0.1 \leq b \leq 0.4$, $0.01 \leq c \leq 0.3$, $0 \leq d \leq 0.2$, and $0 \leq e \leq 0.1$; an atomic ratio a/b is $0.85 \leq a/b < 1.0$, and an atomic ratio a/c is $1.4 < a/c < 2.3$.), the method including: a step of preparing a specific raw material-formulated solution containing Mo, V, Sb, Nb, W, and Z; a step of drying the raw material-formulated solution to obtain a dry powder; a step of pre-stage calcining the dry powder to obtain a pre-stage calcined product; a step of main-calcining the pre-stage calcined product to obtain a calcined product having a protrusion on the surface of the particle; and a step of removing the protrusion by an air stream, wherein the reduction rate of the pre-stage calcined product is 8 to 12%, and the specific surface area of the calcined product is 7 to 20 m²/g.

22 Claims, 6 Drawing Sheets

COMPOSITE OXIDE CATALYST AND METHOD FOR PRODUCING THE SAME

BACKGROUND OF THE INVENTION

Field of the Invention

The present invention relates to a composite oxide catalyst used for a vapor-phase catalytic oxidation or vapor-phase catalytic ammoxidation reaction of propane or isobutane and a method for producing the composite oxide catalyst, and a method for producing an unsaturated acid or unsaturated nitrile using the composite oxide catalyst.

Description of the Related Art

It is conventionally known that a method for subjecting propylene or isobutylene to a vapor-phase catalytic oxidation or vapor-phase catalytic ammoxidation reaction to produce corresponding unsaturated carboxylic acid or unsaturated nitrile. In recent years, attention has been directed to a method for subjecting propane or isobutane instead of propylene or isobutylene to a vapor-phase catalytic oxidation or vapor-phase catalytic ammoxidation to produce corresponding unsaturated carboxylic acid or unsaturated nitrile.

For this reason, as a catalyst of vapor-phase catalytic ammoxidation of propane or isobutane, a variety of oxide catalysts have been proposed.

The ammoxidation catalyst is usually a metal oxide obtained by mixing, drying, and calcining molybdenum, vanadium, antimony, niobium, and the like when necessary. The composition of metals contained in the metal oxide has been examined in a variety of composition ratios because the composition ratio directly influences the ability of the catalyst. Further, recently, it is found that physical properties of the metal oxide that cannot be expressed only by the composition ratio also influence the ability of the catalyst.

For example, Patent Literature 1 describes a metal oxide containing molybdenum, vanadium, antimony, and niobium, and having a reduction rate of 8 to 12%, and a specific surface area of 5 to 30 m²/g.

Patent Literature 2 describes production of a protruding substance that inhibits fluidity on the surface of an ammoxidation catalyst. According to Patent Literature 2, by removing the substance from the surface of the catalyst, a yield of a target product can be maintained, and an unsaturated acid and an unsaturated nitrile can be produced.

Patent Literature 1: International Publication WO 2004-108278
Patent Literature 2: Japanese Patent Application Laid-Open No. 2007-216212

Problems to be Solved by the Invention

As described in Patent Literatures 1 and 2, to be sure, if the reduction rate and specific surface area of the metal oxide are optimized by selection of a catalyst preparation condition, the ability of the catalyst is improved. Moreover, if the protruding substance (hereinafter, referred to as a "protrusion") produced on the surface of the catalyst is removed after calcination, the yield of the target object is easily maintained.

According to the examination by the present inventors, however, the composition of the protrusion is different from that of the core portion of the catalyst. For this reason, if the protrusion is removed, the composition of the catalyst to be produced is different from the composition at the time of preparation. Namely, it was found out that even if the composition at the time of preparation is optimized, and the reduction rate and the specific surface area are determined based on the composition at the time of preparation, part of the composition at the time of preparation is removed as the protrusion after the preparation; for this reason, the composition after preparation is deviated from the optimal value.

In consideration of the circumstances above, an object of the present invention is to provide a complex oxide catalyst used for a vapor-phase catalytic oxidation or a vapor-phase catalytic ammoxidation reaction of propane or isobutane, in which metals that form the complex oxide catalyst have a proper composition ratio after a step of removing a protrusion that exists on a surface of a particle, and a method for producing the complex oxide catalyst.

Means for Solving the Problems

As a result by extensive research in order to solve the problems above, the present inventors discovered that of the composition of the complex oxide, the step of removing a protrusion is greatly influenced particularly by a composition ratio of vanadium and antimony V/Sb and a composition ratio of vanadium and niobium V/Nb. It was also found out that if a composition at the time of preparation is optimized at a stage of preparing a raw material, a catalyst containing a complex oxide having a proper metal composition ratio is obtained. Thus, the present invention has been achieved.

Namely, the present invention is as follows.

[1] A complex oxide catalyst used for a vapor-phase catalytic oxidation reaction or vapor-phase catalytic ammoxidation reaction of propane or isobutane, the catalyst comprising a complex oxide represented by the following formula (1):

$$Mo_1V_aSb_bNb_cW_dZ_eO_n \tag{1}$$

(wherein a component Z represents one or more elements selected from La, Ce, Pr, Yb, Y, Sc, Sr, and Ba; a, b, c, d, e, and n each represent an atomic ratio of an element to one Mo atom; $0.1 \leq a \leq 0.4$, $0.1 \leq b \leq 0.4$, $0.01 \leq c \leq 0.3$, $0 \leq d \leq 0.2$, and $0 \leq e \leq 0.1$; an atomic ratio a/b is $0.85 \leq a/b < 1.0$, and an atomic ratio a/c is $1.4 < a/c < 2.3$).

[2] The complex oxide catalyst according to [1] above containing 20 to 70% by mass of silica in terms of $SiO_2$.

[3] A method for producing a complex oxide catalyst comprising a complex oxide represented by the following formula (1):

$$Mo_1V_aSb_bNb_cW_dZ_eO_n \tag{1}$$

(wherein a component Z represents one or more elements selected from La, Ce, Pr, Yb, Y, Sc, Sr, and Ba; a, b, c, d, e, and n each represent an atomic ratio of an element to one Mo atom; $0.1 \leq a \leq 0.4$, $0.1 \leq b \leq 0.4$, $0.01 \leq c \leq 0.3$, $0 \leq d \leq 0.2$, and $0 \leq e \leq 0.1$; an atomic ratio a/b is $0.85 \leq a/b < 1.0$, and an atomic ratio a/c is $1.4 < a/c < 2.3$), the method comprising the steps (I) to (V):

(I) preparing a raw material-formulated solution containing Mo, V, Sb, Nb, W, and Z, wherein an atomic ratio a of V to one Mo atom is $0.1 \leq a \leq 0.5$, an atomic ratio b of Sb to one Mo atom is $0.1 \leq b \leq 0.5$, an atomic ratio c of Nb to one Mo atom is $0.01 \leq c \leq 0.5$, an atomic ratio d of W to one Mo atom is $0 \leq d \leq 0.4$, and an atomic ratio e of Z to one Mo atom is $0 \leq e \leq 0.2$;

(II) drying the raw material-formulated solution to obtain a dry powder;

(III) pre-stage calcining the dry powder to obtain a pre-stage calcined product;

(IV) main-calcining the pre-stage calcined product to obtain a calcined product having a protrusion on a surface of a particle; and (V) removing the protrusion existing on the surface of the particle of the calcined product by an air stream, wherein a reduction rate of the pre-stage calcined product is 8 to 12%, and a specific surface area of the calcined product is 7 to 20 m²/g.

[4] The method for producing a complex oxide catalyst according to [3] above, wherein a content of particles having a particle size of not more than 25 μm in the dry powder is not more than 20% by mass, and an average particle size of the dry powder is 35 to 75 μm.

[5] The method for producing a complex oxide catalyst according to [3] or [4] above, wherein in the step (V), the protrusion is removed so that the amount of the protrusion that the calcined product has is not more than 2% by mass based on a total mass of the calcined product.

[6] The method for producing a complex oxide catalyst according to any of [3] to [5] above, wherein a length of the air stream in a direction of the air stream flowing is not less than 55 mm, and an average flow rate of the air stream is not less than 80 m/s and not more than 500 m/s as a linear velocity at 15° C. and 1 atmospheric pressure.

[7] The method for producing a complex oxide catalyst according to any of [3] to [6] above, wherein the step (I) comprises the steps (a) to (d):

(a) preparing an aqueous mixed-solution containing Mo, V, Sb, and the component Z;

(b) adding silica sol and a hydrogen peroxide solution to the aqueous mixed-solution obtained in the step (a);

(c) mixing an aqueous solution containing Nb, dicarboxylic acid, and the hydrogen peroxide solution and a W compound with the solution obtained in the step (b); and (d) adding a powder silica-containing suspension to the solution obtained in the step (c) and aging the solution.

[8] The method for producing a complex oxide catalyst according to any of [3] to [7] above, wherein the (III) pre-stage calcination step and/or the (IV) main calcination step comprises the steps (i) and (ii):

(i) giving impact to a calcining apparatus in which the pre-stage calcined product and/or the calcined product is calcined; and (ii) annealing the pre-stage calcined product and/or the calcined product at a temperature lower than the calcining temperature in the main calcination.

[9] A method for producing an unsaturated acid using the complex oxide catalyst according to [1] or [2] above, wherein propane or isobutane is subjected to a vapor-phase catalytic oxidation reaction to produce a corresponding unsaturated acid.

[10] A method for producing an unsaturated nitrile using the complex oxide catalyst according to [1] or [2] above, wherein propane or isobutane is subjected to a vapor-phase catalytic ammoxidation reaction to produce a corresponding unsaturated nitrile.

Advantages of the Invention

According to the present invention, a complex oxide catalyst having an optimized metal composition ratio of metals that form the complex oxide catalyst can be provided. The complex oxide catalyst according to the present invention shows a high ability of a catalyst because the metal composition ratio is optimized.

DETAILED DESCRIPTION OF THE PREFERRED EMBODIMENT

Figure 1:
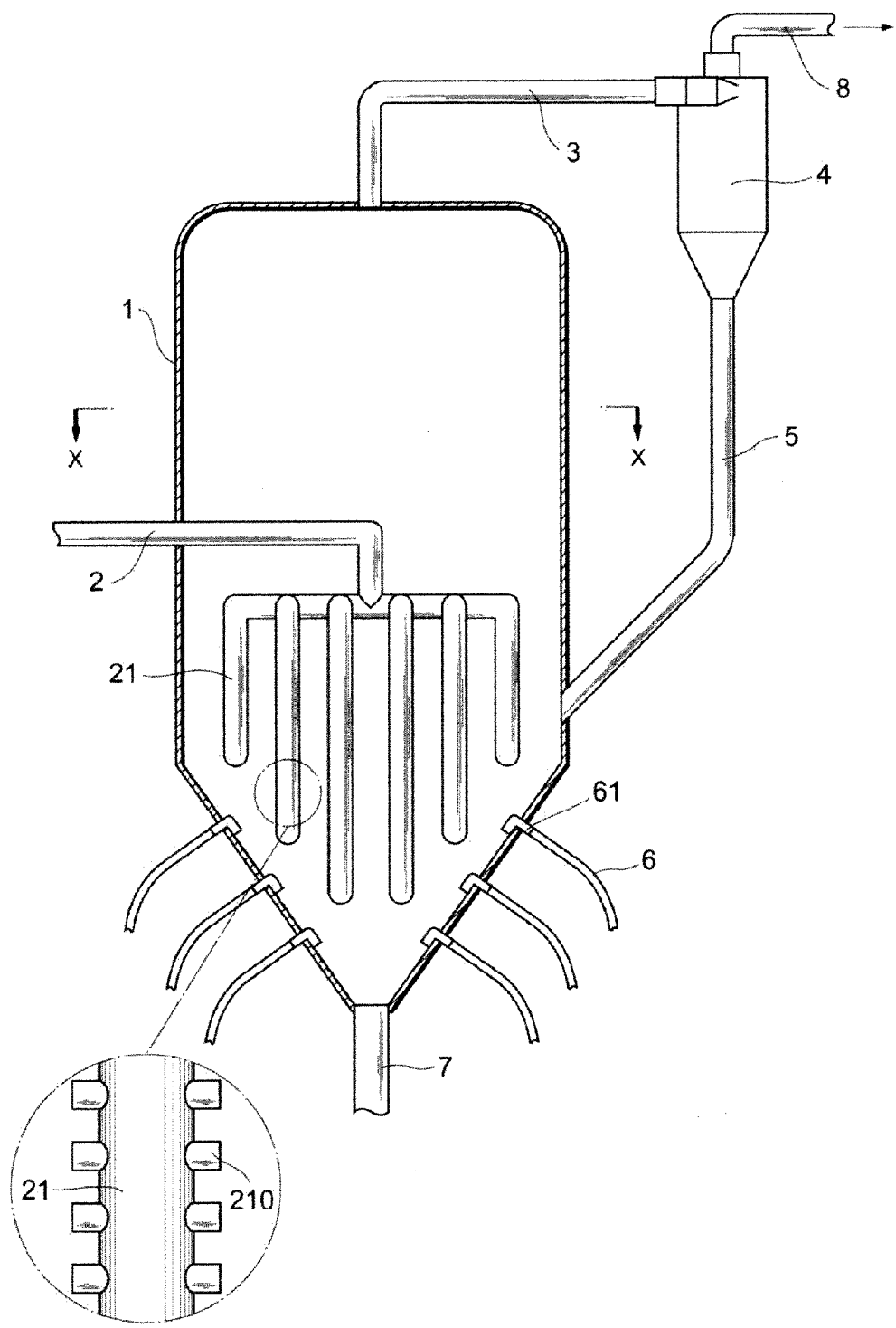
FIG. 1 is a diagram schematically showing one example of a protrusion removing apparatus according to the present embodiment.

Hereinafter, an embodiment of the present invention (hereinafter, referred to as "the present embodiment") will be described in detail. Note that the present invention is not limited to the following embodiment, and many variations may be made within the scope of the present invention.

In the drawings, same reference numerals will be given to same elements, and duplication of description will be omitted. Moreover, vertical and horizontal positional relationships are based on the positional relationships shown in the drawings, unless otherwise specified. The ratios of sizes in apparatuses and members are not limited to the ratios shown in the drawings.

The complex oxide catalyst according to the present embodiment is a complex oxide catalyst used for a vapor-phase catalytic oxidation reaction or vapor-phase catalytic ammoxidation reaction of propane or isobutane, the catalyst containing a complex oxide represented by the following formula (1):

$$Mo_1V_aSb_bNb_cW_dZ_eO_n \qquad (1)$$

(wherein a component Z represents one or more elements selected from La, Ce, Pr, Yb, Y, Sc, Sr, and Ba; a, b, c, d, e, and n each represent an atomic ratio of an element to one Mo atom; $0.1 \leq a \leq 0.4$, $0.1 \leq b \leq 0.4$, and $0.01 \leq c \leq 0.3$, $0 \leq d \leq 0.2$, and $0 \leq e \leq 0.1$; an atomic ratio a/b is $0.85 \leq a/b < 1.0$, and an atomic ratio a/c is $1.4 < a/c < 2.3$.)

The complex oxide catalyst according to the present embodiment has a high ability of a catalyst because the metal composition ratio is optimized. The method for producing the complex oxide catalyst according to the present embodiment is not particularly limited. Preferably, the complex oxide catalyst according to the present embodiment is produced by the method comprising the following steps (I) to (V):

(I) a step of preparing a raw material-formulated solution containing Mo, V, Sb, Nb, W, and Z, wherein an atomic ratio a of V to one Mo atom is $0.1 \leq a \leq 0.5$, an atomic ratio b of Sb to one Mo atom is $0.1 \leq b \leq 0.5$, an atomic ratio c of Nb to one Mo atom is $0.01 \leq c \leq 0.5$, an atomic ratio d of W to one Mo atom is $0 \leq d \leq 0.4$, and an atomic ratio e of Z to one Mo atom is $0 \leq e \ 0.2$;

(II) a step of drying the raw material-formulated solution to obtain a dry powder;
(III) a step of pre-stage calcining the dry powder to obtain a pre-stage calcined product;
(IV) a step of main-calcining the pre-stage calcined product to obtain a calcined product having a protrusion on the surface of a particle; and
(V) a step of removing the protrusion existing on the surface of the particle of the calcined product by an air stream, wherein the reduction rate of the pre-stage calcined product is 8 to 12%, and the specific surface area of the calcined product is 7 to 20 $m^2/g$.

(Step (I) Raw Material Formulating Step)

Step (I) is a step of preparing a raw material-formulated solution containing Mo, V, Sb, Nb, W, and Z, wherein the atomic ratio of V to one Mo atom is $0.1 \leq a \leq 0.5$, the atomic ratio b of Sb to one Mo atom is $0.1 \leq b \leq 0.5$, the atomic ratio c of Nb is $0.01 \leq c \leq 0.5$, the atomic ratio d of W to one Mo atom is $0 \leq d \leq 0.4$, and the atomic ratio e of Z to one Mo atom is $0 \leq e \leq 0.2$. Herein, "formulation" and "preparation" are synonymous.

In the raw material formulating step, elements that form the complex oxide catalyst are dissolved or dispersed in a solvent and/or a disperse medium in a specific proportion to obtain a raw material-formulated solution. As the solvent for the raw material-formulated solution, an aqueous medium is preferable. Usually, water can be used. The raw material-formulated solution contains Mo, V, Sb, Nb, W, and Z (Z represents one or more elements selected from La, Ce, Pr, Yb, Y, Sc, Sr, and Ba). As a raw material for the raw material-formulated solution, a salt or compound containing elements that form the complex oxide catalyst can be used.

In the raw material formulating step, the raw material-formulated solution is prepared so that the atomic ratio of V to one Mo atom is $0.1 \leq a \leq 0.5$, the atomic ratio b of Sb to one Mo atom is $0.1 \leq b \leq 0.5$, the atomic ratio c of Nb to one Mo atom is $0.01 \leq c \leq 0.5$, the atomic ratio d of W to one Mo atom is $0 \leq d \leq 0.4$, and the atomic ratio e of Z to one Mo atom is $0 \leq e \leq 0.2$. The composition ratio is set at different values from those in the composition ratio of the complex oxide catalyst to be finally obtained. This is because the protrusion in the catalyst described later has a composition different from that of the catalyst main body, and if the protrusion is removed the catalyst main body, the composition ratio of the catalyst as a whole is deviated from the composition ratio in the raw material formulating step. Herein, the "protrusion" indicates objects exuded and/or adhering onto the surface of the calcined product obtained by the main calcination described later, and refers to objects protruding from the surface of the calcined product or adhering thereto. Here, many protrusions are protruding crystals of oxides and other impurities. Particularly, in the case of the calcined product containing a plurality of metals, oxides having a composition different from that of the crystals that constitute most of the calcined product may be formed in such a shape that the oxides are exuded from the calcined product main body. In this case, the protrusion is often formed in a shape of a plurality of protrusions (for example, a height of 0.1 μm to 20 μm) on the surface of a spherical calcined product (for example, a diameter of 30 to 150 μm). The composition of the protrusion and the step of removing the protrusion will be described in detail later.

As a raw material for Mo, ammonium heptamolybdate $[(NH_4)_6Mo_7O_{24} \cdot 4H_2O]$, molybdenum trioxide $[MoO_3]$, phosphorus molybdate $[H_3PMo_{12}O_{40}]$, silicon molybdate $[H_4SiMo_{12}O_{40}]$, molybdenum pentachloride $[MoCl_5]$, and the like can be used. Particularly preferred is ammonium heptamolybdate $[(NH_4)_6Mo_7O_{24} \cdot 4H_2O]$.

As a raw material for V, ammonium metavanadate $[NH_4VO_3]$, vanadium pentoxide $[V_2O_5]$, vanadium chlorides $[VCl_4, VCl_3]$ and the like can be used. Particularly preferred is ammonium metavanadate $[NH_4VO_3]$.

As a raw material for Sb, antimony oxides $[Sb_2O_3, Sb_2O_5]$, antimonous acid $[HSbO_2]$, antimonic acid $[HSbO_3]$, ammonium antimonate $[(NH_4)SbO_3]$, antimony chloride $[Sb_2Cl_3]$, organic acid salts such as tartaric acid salt of antimony, metal antimony, and the like can be used. Particularly preferred is diantimony trioxide $[Sb_2O_3]$.

As raw materials for Nb, niobic acid, an inorganic niobate and an organic niobate can be used. In particular, niobic acid is preferable. Niobic acid is represented by $Nb_2O_5 \cdot nH_2O$ and is also referred to as niobium hydroxide or niobium oxide hydrate. Further, as raw materials for Nb, a Nb raw material solution in which a molar ratio of dicarboxylic acid/niobium is 1 to 4 is also preferably used, and as the dicarboxylic acid, oxalic acid is preferable.

As a raw material for W, salts of tungsten such as ammonium salts, nitric acid salts, carboxylic acid salts, carboxylic acid ammonium salts, peroxocarboxylic acid salts, peroxocarboxylic acid ammonium salts, halogenated ammonium salts, halides, acetyl acetonate, alkoxide, triphenyl compounds, polyoxometalate, and polyoxometalate ammonium salts of tungsten; tungsten trioxide, tungsten dioxide, tungsten acid, an ammonium metatungstate aqueous solution, ammonium para tungstate, tungstosilicic acid, silicotungstomolybdic acid, tungstosilicic acid, and the like can be used. Among these, an ammonium metatungstate aqueous solution is preferred.

Raw materials for Z (one or more elements selected from La, Ce, Pr, Yb, Y, Sc, Sr and Ba) are not particularly limited as long as the raw materials contain these elements. A compound containing these elements and a solution in which the metal of these elements is solubilized in an appropriate reagent can be used. As the compound containing these elements, an ammonium salt, a nitrate, a carboxylate, an ammonium salt of a carboxylic acid, a peroxocarboxylate, an ammonium salt of a peroxocarboxylic acid, a halogenated ammonium salt, a halide, acetyl acetate, and an alkoxide can usually be used. Preferably, an aqueous raw material such as a nitrate, and a carboxylate can be used.

In the formulation of the raw material, the procedure of dissolving the raw materials for the catalyst constituting elements, the procedure of mixing the raw material, or the procedure of dispersing the raw material is not particularly limited. The raw materials may be dissolved, mixed, or dispersed in the same aqueous medium. Alternatively, the raw materials may be separately dissolved, mixed, or dispersed in an aqueous medium, and the aqueous mediums may be mixed. When necessary, heating and/or stirring may be performed.

In the complex oxide catalyst, one of important points is that the component Z is uniformly distributed in the catalyst particles. Preferably, the catalyst is in such a state. Here, "uniformity" means that the distribution of the component Z in the catalyst particles is not uneven. Preferably, the "uniformity" means that not less than 80% of oxide particles containing the component Z (mass ratio) exist in the catalyst particles as fine particles having a particle size of not more than 1 μm. In the case where the complex oxide catalyst contains silica, a suitable definition of the "uniformity" is that when the cross section of the catalyst particle is subjected to composition analysis, a dispersion value (a value obtained by dividing the standard deviation by the average value) of a signal intensity ratio of the component Z to Si is in the range of 0 to 0.5. Here, the dispersion value is shown by "Dx."

An ordinary composition analysis method can be used for the composition analysis. For example, SEM-EDX, XPS, SIMS, EPMA, and the like can be used. Preferably, the EPMA can be used. Here, the EPMA is commonly called an Electron Probe X-ray Microanalyzer (the term X-ray may be omitted to refer to the apparatus). The analysis apparatus is an apparatus in which a characteristic X-ray obtained by irradiating a substance with an accelerated electron beam is observed to perform the composition analysis of the fine region (spot) irradiated with the electron beam. By the EPMA, usually, about the cross section of the solid particle such as catalyst particles and carrier particles, information on a specific element such as the concentration distribution and change in the composition is obtained.

The dispersion value (Dx) of the intensity ratio of the component Z to Si analyzed by the EPMA is a value obtained by measuring the cross section of the particle to be measured and performing calculation according to an ordinary method for plane analysis of the cross section of the particle by the EPMA, which is performed in the field of the catalyst, as follows. Namely, first, distribution of X-ray peak intensity of Si (the number of count ISi) in any position (x, y) in the cross section of the catalyst particle is measured so that the entire cross section of the catalyst particle is covered. Next, similarly, distribution of X-ray peak intensity (the number of count IX) of the component Z is measured so that the entire cross section of the catalyst particle is covered. Based on the obtained series of data (x, y, ISi, IX) on Si and the component Z, a peak intensity ratio IR of the component Z to Si (IR=IX/ISi) in the same position (x, y) is determined, and the simple average (IR)av and standard deviation S of IR are determined. The value obtained by dividing the standard deviation S by the simple average (IR)av is defined as the dispersion value (Dx). At this time, the simple average and the standard deviation may be determined by an ordinary method. Herein, the "complex oxide catalyst (simply referred to as a "catalyst" in some cases)" means a product obtained by removing the protrusion produced on the surface of the particle from the calcined product after the main calcination. The measurement of the dispersion value is performed by observation of the cross section, and is not influenced by the state of the surface of the catalyst. Accordingly, the dispersion value indicates the same value even if the value is measured after the main calcination and before the step of removing the protrusion.

Preferably, in order to avoid uncertainty of data due to an edge effect of the cross section of the particle in the measurement, a region that is 10% of the cross section area in the cross section of the catalyst particle and corresponds to the outer periphery of the particle is excluded, a region of 90% from the center in the cross section of the catalyst particle is used as an effective region, and the data of the effective region is calculated. Of course, from the beginning, the plane analysis by the EPMA may be performed on only the inside of the cross section of the catalyst particle from which 10% of the region corresponding to the outer periphery of the particle is excluded, and the dispersion value Dx may be determined from the data.

Next, a suitable method for plane analysis of the cross section of the catalyst particle will be described.

First, the particles to be measured are embedded in a proper matrix resin. The matrix resin is polished, and entirely scraped until the cross sections of the embedded catalyst particles are exposed. Next, the EPMA measurement is performed on the catalyst particles whose cross sections are exposed, as follows.

(1) A sample is positioned so that the cross section of the catalyst particle is within the observation field in the EPMA measurement.

(2) The cross section of the catalyst particle is irradiated with an electron beam, the intensity of the characteristic X-ray of Si or the component Z coming from the portion irradiated with the electron beam is counted, and the region to be analyzed is scanned with an electron beam to perform the plane analysis.

In the case where the complex oxide catalyst according to the present embodiment is a catalyst containing silica, and preferably a silica-carried catalyst carried on silica, the raw material-formulated solution is preferably prepared so as to contain a silica raw material. As the raw material for silica, silica sol can be used. Powder silica can be used for part of the silica raw material or the whole silica raw material.

The content of silica contained in the catalyst, preferably, the content of a carrier silica is preferably not less than 20% by mass from the viewpoint of improving strength of the catalyst, and preferably not more than 70% by mass from the viewpoint of giving sufficient activity, in terms of $SiO_2$ based on the total mass of the catalyst containing complex oxide and silica. The content is more preferably 40 to 65% by mass based on the total mass of the catalyst.

Preferably, the silica sol contains 10 to 270 wtppm, and more preferably 10 to 270 wtppm of nitric acid ions based on the mass of $SiO_2$ in the silica so. Although the reason is not certain, the following factor can be thought. The factor is not limited to this. Namely, the concentration of nitric acid ions in the silica sol that is a silica carrier raw material can be properly adjusted in a specific range to properly control the aggregation of the silica sol. By use of such silica sol as the carrier raw material, a high yield of the target object is provided, and a silica-carried catalyst having high physical strength is obtained.

Here, the concentration of nitric acid ions to silica in the silica sol can be determined by ion chromatography. The measurement apparatus and the measurement condition are shown below. As the measurement apparatus, an apparatus (trade name "IC-2001") made by Tosoh Corporation can be used. As the column, a TSKgel superIC-AZ (trade name) is used. As a guard column, a TSKguardcolumn superIC-AZ (trade name) is used. Further, as a suppressor valve washing liquid, a TSKsupress A (trade name) is used. As an eluent, 1.9 mmol/L of a $NaHCO_3$ aqueous solution and 3.2 mmol/L of $Na_2CO_3$ aqueous solution are mixed and used. The flow rate at this time is 0.8 mL/min.

In order to describe a method for adjusting the concentration of nitric acid ions in the silica sol, first, an industrial method for producing silica sol will be described. Examples of the industrial method for producing silica sol include (1) dialysis after neutralization of water glass, (2) electrical dialysis, (3) dissolving of metal silicon in an ammonia or amine aqueous solution, (4) peptization of silica gel, and (5) removing Na from water glass by an ion exchange resin. Among these, the most ordinary method for producing silica sol is (5) the method using an ion exchange resin (ion exchange resin method). In order to enhance stability under a high concentration, LiOH, NaOH, or KOH as a stabilizer is added to the silica sol produced by the ion exchange resin method. For this reason, usually, a stable pH region for the silica sol is appropriately 8 to 10. In order to keep a stable dispersion state of the silica sol, silica particles in the sol need to repel each other with respect to electric charge. For this season, the stabilizer is added as described above, $OH^-$ is adsorbed to the surfaces of the silica particles, and the stabilizing effect by negative charge is demonstrated. Thereby, gelation is prevented. However, it is known that if excessive alkalis (alkali metal ions in the stabilizer) are added, the alkali ions are adsorbed to reduce negative charge, resulting in an unstable state of the silica sol. Recently, many silica sols that have properties intrinsic to these silica sols and can be used in various applications are commercially available. Examples of the commercially available silica sol include SNOWTEX series made by Nissan Chemical Industries, Ltd., specifically, SNOWTEX 30 having a concentration of the silica sol of 30%, SNOWTEX C used in applications in which gelation may occur, SNOWTEX N used to prevent alkalis to remain using a volatile weak base as a stabilizer, and SNOWTEX O suitable for applications in which use in an acidic state is necessary (reference: Shokubai Kougakukouza 10, Gensobetu Shokubai Binran, published Feb. 25, Showa 42).

Looking at the surfaces of the silica particles of the silica sol obtained by the method above, the silica sol is classified into an acid type and an alkali type. In both types, however, nitric acid ions hardly exist in the silica sol. For example, mainly hydrogen ions are used as the stabilizer in the acid type. On the other hand, sodium ions or ammonium ions are used as the stabilizer in the alkali type. As a counter anion in the acid type, $SO_4^{2-}$, $Cl^-$, and the like are used. As a counter anion in the alkali type, $OH^-$ is usually used.

In both cases of the acid type and the alkali type of the silica sol, to obtain a silica sol in which a mass proportion of nitric acid ions are 10 to 270 wtppm based on the mass of silica, in using an ordinary method for producing silica sol such as neutralization of a water glass aqueous solution with sulfuric acid or hydrochloric acid, a nitric acid or a nitric acid salt such as ammonium nitrate is preferably added to adjust the amount of nitric acid ions to silica at 10 to 270 wtppm. Alternatively, after neutralization with sulfuric acid or hydrochloric acid, anions in the water glass aqueous solution may be exchanged for nitric acid ions by ion exchange. Nitric acid ions may be added to an existing silica sol by a pipette or the like to adjust the amount of nitric acid ions. The nitric acid source may be nitric acid, and salts such as ammonium nitrate. The primary particle of the silica sol is usually spherical. A non-spherical silica sol, or a sol having spherical particles connected to one another may be used.

As the raw material for the silica carrier, only silica sol may be used. Alternatively, part of the raw material can be replaced by powder silica. If the powder silica is used as the raw material for the silica carrier, an effect of improving the activity of the catalyst and/or yield of the target object is expected. On the other hand, if only the powder silica is used without using the silica sol to prepare the catalyst, the resistance to wear of the catalyst is remarkably reduced. Herein, the term "powder silica" indicates fine particles of solid $SiO_2$. If the primary particle size of the powder silica is excessively large, the catalyst to be obtained is likely to be fragile. Accordingly, the powder silica of a nanometer size is preferred. The powder silica is preferably produced by a high-temperature method. Specific examples of preferred powder silica include Aerosil 200 (trade name) made by Nippon Aerosil Co., Ltd.

From the viewpoint of easiness in addition to and mixing with the raw material-formulated solution, the powder silica is preferably dispersed in advance in water. A method of dispersing the powder silica in water is not particularly limited, and the power silica can be dispersed using an ordinary homogenizer, homomixer, or ultrasonic vibrator alone or in combination thereof. The primary shape of the powder silica at this time may be spherical, or non-spherical.

In the case where the silica sol and the powder silica are used as the raw material for the silica carrier, the amount of the powder silica is preferably 20 to 70% by mass of the total amount of the silica sol and the powder silica. If the amount of the powder silica is more than 70% by mass, the resistance to wear of the catalyst is likely to be reduced. If the amount is less than 20% by mass, the activity of the catalyst and/or the yield of the target object is likely to be reduced. The powder silica may not contain nitric acid ions. Even if the concentration of nitric acid ions in the silica sol (the mass proportion of nitric acid ions to the mass of silica) is adjusted to 10 to 270 wtppm based on $SiO_2$ in order to increase the yield and/or physical strength of the target object, nitric acid ions contained in the powder silica do not need to be adjusted.

Hereinafter, the raw material formulating step will be described using an example in which the solvent and/or disperse medium is water, and the raw material-formulated solution for the silica-carried catalyst containing an Mo compound, a V compound, an Sb compound, an Nb compound, a W compound, and a Z compound is prepared. The raw material formulating step is not limited to this.

First, an aqueous mixed-solution containing Mo, V, Sb, and the component Z is prepared. More specifically, the Mo compound, the V compound, the Sb compound, and the component Z compound are added to water, and the solution is heated to prepare an aqueous mixed-solution (A). The heating temperature and heating time during preparation of the aqueous mixed-solution (A) are preferably adjusted so that the raw material compound is sufficiently dissolved. The heating temperature is preferably 70° C. to 100° C., and the heating time is preferably 30 minutes to 5 hours. The number of rotation of stirring during heating can be similarly adjusted to the number of rotation at which the raw material is easily dissolved. In the case where the raw material is a metal salt, the state of stirring is preferably kept from the viewpoint of sufficiently dissolving the metal salt. At this time, the inside of a container may be an air atmosphere. From the viewpoint of adjusting the oxidation number of the complex oxide catalyst to be obtained, a nitrogen atmosphere can be used. The state where heating of the aqueous mixed-solution (A) is completed is called an aqueous mixed-solution (A'). The aqueous mixed-solution (A') is preferably kept at a temperature of not less than 20° C. and not more than 80° C., and more preferably not less than 40° C. and not more than 80° C. At a temperature of the aqueous mixed-solution (A') less than 20° C., a metal kind dissolved in the aqueous mixed-solution (A') may be precipitated.

Next, the silica sol is added to the aqueous mixed-solution (A) or the aqueous mixed-solution (A') after heating is completed. The silica sol functions as a carrier. The temperature when the silica sol is added is preferably not more than 80° C. In the case where the silica sol is added at a temperature more than 80° C., the stability of the silica sol may be reduced to gelate the raw material-formulated solution. The timing at which the silica sol is added may be a time of starting aging described later, during aging, or a time immediately before drying the raw material-formulated solution. Preferably, the silica sol is added to the aqueous mixed-solution (A'). Further, from the viewpoint of adjusting the oxidation number of the complex oxide to be obtained, a proper amount of a hydrogen peroxide solution is preferably added to the aqueous mixed-solution (A') when necessary. The hydrogen peroxide solution may be added at any timing; the hydrogen peroxide solution may be added to the aqueous mixed-solution (A') itself, or added while the aqueous mixed-solution (A') is formulated, or added before or after the silica sol is added. At this time, from the viewpoint of adjusting the oxidation number of the complex oxide catalyst to be obtained in a proper range, the amount of the hydrogen peroxide solution to be added is preferably 0.01 to 5, more preferably 0.5 to 3, and particularly preferably 1 to 2.5 in $H_2O_2/Sb$ (molar ratio).

The heating temperature and heating time after the hydrogen peroxide solution is added to the aqueous mixed-solution (A') is preferably adjusted so that liquid phase oxidation reaction by the hydrogen peroxide solution can sufficiently progress. The heating temperature is preferably 30° C. to 70° C., and the heating time is preferably 5 minutes to 4 hours. Similarly, the number of rotation of stirring during heating can be adjusted at the number of rotation that the liquid phase oxidation reaction by the hydrogen peroxide solution easily progresses. From the viewpoint of sufficient progression of the liquid phase oxidation reaction by the hydrogen peroxide solution, stirring is preferably continued during the heating. The thus-prepared aqueous mixed-solution is called an aqueous mixed-solution (A").

Next, the Nb compound and dicarboxylic acid are heated and stirred in water to prepare a mixed-solution ($B_0$). Examples of dicarboxylic acid include oxalic acid $[(COOH)_2]$. Next, a hydrogen peroxide solution is preferably added to the mixed-solution ($B_0$) to prepare an aqueous mixed-solution (C). At this time, $H_2O_2/Nb$ (molar ratio) is preferably 0.5 to 20, and more preferably 1 to 10 from the viewpoint of forming a complex with the Nb compound and stabilizing the complex in a dissolved state, properly adjusting the state of oxidation and reduction of the catalyst constituting elements, and optimizing the ability of the catalyst to be obtained.

Next, depending on a target composition, the aqueous mixed-solution (A"), the aqueous mixed-solution (C), the W compound, and the powder silica are suitably mixed to obtain an aqueous mixed-solution (D). Subsequently, the obtained aqueous mixed-solution (D) is aged to obtain a raw material-formulated solution. Preferably, the powder silica used here is added to a solution obtained by mixing the aqueous mixed-solution (A"), the aqueous mixed-solution (C), and the W compound from the viewpoint of optimizing the ability of the catalyst to be obtained. The powder silica can be added as it is. More preferably, the power silica is added as a solution in which the powder silica is dispersed in water, namely, a powder silica-containing suspension. The concentration of the powder silica in the powder silica-containing suspension at this time is preferably 1 to 30% by mass, and more preferably 3 to 20% by mass. At a concentration of the powder silica less than 1% by mass, the viscosity of a slurry is excessively low. For this reason, the shape of the particle to be obtained may be distorted, and depressions may be likely to be produced in the catalyst particles. On the other hand, at a concentration of the powder silica more than 30% by mass, the viscosity of the raw material-formulated solution is excessively high, and the raw material-formulated solution may be gelated to produce cloggings within a pipe. As a result, it may be difficult to obtain a dry powder, and the ability of the catalyst may be reduced.

Aging of the aqueous mixed-solution (D) means to leave standstill or stir the aqueous mixed-solution (D) for a predetermined time. The aging time is preferably 90 minutes or more and 50 hours or less, and more preferably 90 minutes or more and 6 hours or less. At an aging time less than 90 minutes or more than 50 hours, an aqueous mixed-solution (D) having a suitable state (potential) of oxidation and reduction is difficult to prepare, and the ability of the catalyst of the complex oxide to be obtained is likely to be reduced. Here, in the case where the complex oxide catalyst is industrially produced through drying by a spray dryer, usually, the spray dryer has a rate-limiting treatment speed. For this, it takes some time to spray dry part of the aqueous mixed-solution (D), and complete spray drying of the entire mixed-solution. During this dry spraying, the aqueous mixed-solution not spray dried is continuously aged. Accordingly, the aging time includes not only the aging time before drying in step (II) described later but also the time after the start of drying to the end of drying. An aging temperature is preferably 25° C. or more from the viewpoint of preventing the condensation of a Mo component and the deposition of metal oxide of V and other metal species or a plurality of metals. The aging temperature is preferably 65° C. or less from the viewpoint of preventing the excessive generation of the hydrolysis of a complex containing Nb and hydrogen peroxide and forming a slurry in a preferable form. From the viewpoint above, the aging temperature is preferably 25° C. or more and 65° C. or less, and more preferably 30° C. or more and 60° C. or less.

An atmosphere in the container in aging preferably has a sufficient oxygen concentration. Insufficient oxygen concentration may hardly cause substantial change of the aqueous mixed-solution (D). More specifically, an oxygen concentration of a vapor-phase part in the container is preferably 1 vol % or more, for example, the aqueous mixed-solution (D) can be aged in air atmosphere. The vapor-phase oxygen concentration can be measured by general methods, for example, by a measurement method using a zirconia type oxygen meter. A place where the vapor-phase oxygen concentration is measured is preferably near an interface between the aqueous mixed-solution (D) and vapor phase. For example, preferably, the vapor-phase oxygen concentration is measured three times at the same point within 1 minute, and the mean value of the three measurement results is used as the vapor-phase oxygen concentration.

A dilution gas for reducing the vapor-phase oxygen concentration is not particularly limited. Examples of the dilution gas include nitrogen, helium, argon, carbon dioxide, and steam. Industrially, nitrogen is preferable. As a gas for increasing the vapor-phase oxygen concentration, pure oxygen or air with a high oxygen concentration is preferable.

Some change is considered to occur in an oxidation/reduction state of the component contained in the aqueous mixed-solution (D) by the aging. The occurrence of some change is suggested from the occurrence of change in color and change in an oxidation-reduction potential, or the like of the aqueous mixed-solution (D) during the aging. As a result, the difference in the ability between the composite oxide catalysts occurs, which are obtained by the presence or absence of the aging for 90 minutes or more and 50 hours or less in an atmosphere having an oxygen concentration of 1 to 25 vol %. Specifically, it is extremely difficult to correctly identify change in the form of the component in the liquid during the aging. However, catalysts having a different aging time are produced, and the ability is evaluated, and thereby it can be inferred that an aging time imparted to a catalyst having a good ability is preferable and a slurry having some preferable form is formed on this occasion.

The oxidation-reduction potential of the aqueous mixed-solution (D) is controlled by a potential (600 mV/AgCl) of an aqueous raw-material solution (C). For example, it is considered that when the aqueous raw-material solution (C)

contains Nb oxalate peroxide, Nb oxalate peroxide and other metal components cause some oxidation-reduction reaction to cause temporal reduction in the potential. The oxidation-reduction potential of the aqueous mixed-solution (D) is preferably 450 to 530 mV/AgCl, and more preferably 470 to 510 mV/AgCl.

The oxygen concentration during the aging is preferably 1 vol % or more from the viewpoint of preventing excessive delay in the progress of the oxidation-reduction reaction having some influence on the oxidation/reduction state of the components contained in the aqueous mixed-solution (D), and preventing some excessive reduction of the oxidation/reduction state in the raw material-formulated solution. On the other hand, the oxygen concentration during the aging is preferably 25 vol % or less from the viewpoint of preventing some excessive oxidation of the raw material-formulated solution caused by the excessive progress of the oxidation-reduction reaction. Anyhow, it is necessary to maintain the oxygen concentration in an appropriate range since vapor-phase oxygen has an influence on the oxidation-reduction condition of the raw material-formulated solution. The range is more preferably 5 to 23 vol %, and still more preferably 10 to 22 vol %.

During aging of the aqueous mixed-solution (D), moisture content may be vaporized to produce condensation. If aging is performed in an open system, the moisture content is naturally vaporized. If aging is not performed under an atmosphere of a concentration of oxygen of 1 to 25 vol %, the ability of the catalyst may not be improved.

In the stirring during the aging, the density of the solution, the amount of the raw material-formulated solution, the number of rotation of a stirring blade, or the like is preferably controlled from the viewpoint of preventing gelation of the raw material-formulated solution, and adjusting the viscosity of the raw material-formulated solution to be obtained in a proper state. If the viscosity of the raw material-formulated solution is excessively low, the shape of the particle to be obtained may be distorted, and depressions may be likely to be produced in the catalyst particles in the spray drying step described later. On the other hand, if the viscosity is excessively high, the raw material-formulated solution may be gelated to produce cloggings within a pipe. As a result, it may be difficult to obtain a dry powder, and the ability of the catalyst may be reduced. Accordingly, preferably, the density of the solution, the amount of the raw material-formulated solution, the number of rotation of the stirring blade or the like is controlled to obtain a raw material-formulated solution having a proper viscosity.

In the stirring during the aging, as ordinary stirring blades, stirring vanes, and the like, a multi blade, an anchor blade, a helical blade, a helical ribbon blade, and the like can be used. Moreover, as a stirring blade for a solution having a low viscosity, a propeller, a disk turbine, a fan turbine, a curved-blade fan turbine, an arrow feather shaped turbine, an inclined blade turbine, and the like can be used.

The power per units volume given to the raw material-formulated solution by the stirring blade of the stirrer in the apparatus for preparing the raw material-formulated solution (hereinafter, referred to as a "Pv") is preferably 0.005 to 300 kW/m³, more preferably 0.01 to 280 kW/m³, and still more preferably 0.1 to 250 kW/m³. If the raw material-formulated solution is stirred by the stirring power at Pv less than 0.005 kW/m³, the raw material-formulated solution may be gelated to produce cloggings within a pipe. As a result, it may be difficult to obtain a dry powder, and the ability of the catalyst may be reduced. If the raw material-formulated solution is stirred by the stirring power at Pv more than 300 kW/m³, depressions may be likely to be produced in the catalyst particles after spray drying. Presence of the depressions adversely affects the strength of the catalyst. The Pv value is represented by the following equation (A), and can be controlled by adjusting the density of the solution, the amount of the raw material-formulated solution, the number of rotation of the stirring blade, and the like.

$$Pv = Np \times \rho \times n^3 \times d^5/V \quad (A)$$

wherein Np: power number that is a dimensionless number concerning the power needed for stirring (–), ρ: density of the solution (kg/m³), n: the number of rotation of the stirring blade (s⁻¹), d: the size of the stirring blade (m), V: the amount of the raw material-formulated solution (m³)

The Np value can be calculated using the following equation (B1):

[Expression 1]

$$Np = \frac{A}{Re} + B\left(\frac{10^3 + 1.2Re^{0.66}}{10^3 + 3.2Re^{0.66}}\right)^v \times \left(\frac{Z}{D}\right)^{(0.35+b/D)} \times (\sin\theta)^{1.2} \quad (B1)$$

wherein $$A = 14 + (b/D)\{670(d/D - 0.6)^2 + 185\} \quad (B2)$$

$$B = 10^{\{1.3 - 4(b/D - 0.5)^2 - 1.14(d/D)\}} \quad (B3)$$

$$p = 1.1 + 4(b/D) - 2.5(d/D - 0.5)^2 - 7(b/D)^4 \quad (B4)$$

$$Re + 10^{4(1-\sin\theta)} \times (25/(b/D) \times (d/D - 0.4)^2 + \quad (B5)$$
$$[(b/D)/\{0.11(b/D) - 0.0048\}])$$

wherein the equations (B1) to (B5) above are as follows:

b represents a width of the stirring blade (m), d represents the size of the stirring blade (m), D represents the size of a stirring tank (m), Z represents the depth of the solution (m), and θ represents the tilt angle (°) of the stirring blade with respect to the horizon.

The viscosity of the raw material-formulated solution to be obtained at room temperature (25° C.) is preferably 1 to 100 cp, more preferably 2 to 90 cp, and still more preferably 2.5 to 80 cp from the viewpoint of suppressing gelation of the raw material-formulated solution, cloggings of the pipe, and difficulties to obtain a dry powder, further suppressing reduction in the ability of the catalyst, and suppressing production of depression in the catalyst particles after spray drying or a distorted shape of the catalyst particles.

The viscosity of the raw material-formulated solution can be measured, for example, by a method in which measurement is conducted using a commercially available viscometer, or a method in which the pressure loss within the pipe through which the raw material-formulated solution flows is measured. For example, in the case where such a viscosity of the solution that gelation gradually progresses without stirring is measured, the viscosity may be gradually changed in measuring the viscosity using a commercially available viscometer. Then, from the viewpoint of reproducibility of the measured value, the viscosity is preferably measured by a method in which the pressure loss within the pipe through which the raw material-formulated solution flows is measured.

In the case where the viscosity of the raw material-formulated solution is measured by method in which the pressure loss within the pipe through which the raw material-formulated solution flows is measured, the viscosity of the solution can be calculated by the following equation (C1):

[Expression 2]

$$\mu = \frac{9.8 \times \Delta P \times D^2}{32 \times 10^{-3} \times uL} \quad (C1)$$

wherein symbols are as follows:
μ: the viscosity of the solution (cp), ΔP: the pressure loss within the pipe (mmH$_2$O), u: the average flow rate of the solution (m/s), L: the length of the pipe (m), D: the diameter of the pipe (m)

In the case where a plurality of raw material solutions in which the respective components of the catalyst are dissolved are mixed to obtain the raw material-formulated solution, the upper limit of Pv when each of the raw material solutions is prepared is not particularly limited. The lower limit of Pv is not particularly limited. Preferably, Pv is not less than the Pv value at which all of or most of the solid particles are away from the bottom of the tank in the apparatus for obtaining the raw material solution and flow in the apparatus. In preparation of the raw material solution, stirring may be stopped after all the solid particles in the respective raw material solutions are substantially dissolved.

In order to adjust the pH of the raw material-formulated solution, an acid and/or alkali may be added to the raw material-formulated solution when necessary.

In the case where the complex oxide catalyst is the silica-carried catalyst, the raw material-formulated solution is preferably prepared so as to contain silica sol from the viewpoint of sufficiently dissolving and/or dispersing the compound containing the catalyst constituting element, properly adjusting the state of oxidation and reduction of the catalyst constituting element, providing a preferred shape and/or strength of the catalyst particles to be obtained, and improving the ability of the catalyst of the complex oxide to be obtained. The silica sol can be properly added. An aqueous dispersion of the silica powder can be used as a portion of the silica sol. The aqueous dispersion of silica powder can also appropriately be added.

The raw material formulating step can be repeatedly performed depending on the amount of production.

The raw material formulating step in the present embodiment preferably includes the following steps (a) to (d):
(a) a step of preparing an aqueous mixed-solution containing Mo, V, Sb, and the component Z;
(b) a step of adding silica sol and a hydrogen peroxide solution to the aqueous mixed-solution obtained in the step (a);
(c) a step of mixing an aqueous solution containing Nb, dicarboxylic acid and a hydrogen peroxide solution and a W compound with the solution obtained in the step (b); and
(d) a step of adding a powder silica-containing suspension to the solution obtained in the step (c), and aging the solution.

(Step (II) Drying Step)

Step (II) is a step of dying the raw material-formulated solution to obtain a dry powder.

The slurry raw material-formulated solution subjected to the raw material formulating step is dried to obtain a dry powder. The drying can be performed by a known method. For example, the drying can be performed by spray drying or evaporation to dryness. In the case where a fluidized bed reaction method is used for the vapor-phase catalytic oxidation reaction or the vapor-phase catalytic ammoxidation reaction, use of spray drying is preferred because it is preferable that a micro spherical dry powder be obtained from the viewpoint of preferable fluidity within the reactor. Spraying in the spray drying method can be performed by a centrifugal system, a two-fluid-nozzle system, or a high-pressure nozzle system. Air heated by steam, and an electric heater or the like can be used as a heat source for drying. The temperature of a heat source for drying at a dryer inlet of a spray dryer (hereinafter, referred to as a "temperature at the inlet of the dryer" in some cases.) is preferably 150 to 300° C. from the viewpoint of providing a preferred shape and/or strength of the catalyst particles to be obtained, and improving the ability of the catalyst of the complex oxide to be obtained. The temperature of discharged air at a dryer outlet (hereinafter, referred to as a "temperature at the outlet of the dryer" in some cases.) is preferably 100 to 160° C.

Preferably, the spray rate, the feeding rate of the raw material-formulated solution, and the number of rotation of an atomizer in the case of a centrifugal type are adjusted so that the dry powder to be obtained has a suitable size. The average particle size of the dry powder is preferably 5 μm to 200 μm, and more preferably 10 to 150 μm.

The average particle size of the dry powder can be determined as follows: according to JIS R 1629-1997 "a Particle Size Distribution Measuring Method By a Laser Diffraction Scattering Method for a Fine Ceramic Raw Material," particle size distribution is measured, and averaged based on the volume. More specifically, part of the dry powder is calcined in the air at 400° C. for 1 hour, and the obtained particles are measured using a laser diffraction scattering particle size distribution measurement apparatus LS230 (trade name) made by Beckman Coulter, Inc.

The average particle size is measured after part of the dry powder is "calcined in the air at 400° C. for 1 hour," because the dry powder is prevented from being dissolved in water. Namely, "calcination in the air at 400° C. for 1 hour" is mainly for measurement, and has nothing to do with the calcining step described later. It may be thought that the particle size is substantially not changed before and after the calcination.

More specifically, the average particle size of the dry powder is measured according to the manual attached to the laser diffraction scattering particle size distribution measurement apparatus (made by Beckman Coulter, Inc., trade name "LS230") as follows. First, after background measurement (Run Speed 60) is performed, 0.2 g of the particles is weighed and placed in a screw cap tube having a proper size, and 10 cc of water is added. The screw cap tube is capped (tightly closed), and sufficiently shaken to disperse the particles in water. 300 W of an ultrasonic wave is applied by the apparatus, and the screw cap tube is sufficiently shaken again. Subsequently, while the ultrasonic wave is applied, the particles dispersed in water are injected into the apparatus main body using a pipette so as to obtain a proper concentration (concentration of 10, PIDS of 60). When the concentration displayed is stabilized, application of the ultrasonic wave is stopped. The screw cap tube is left as it is for 10 seconds, and the measurement is started (measurement time of 90 seconds). The value (D50) of a median size in the measurement result is defined as the average particle size.

Also preferable, part of the dry powder obtained in step (II) is recovered, and the absorption or reflectance spectrum is measured. If the absorption or reflectance spectrum of the dry powder obtained in step (II) is continuously measured, the ability of the complex oxide catalyst to be obtained can be finally predicted from the absorption or reflectance spectrum. Here, the degree of oxidation and reduction of the complex oxide catalyst is changed, for example, by heating in the drying step, and the ability of the complex oxide catalyst to be obtained is influenced. Accordingly, using this as an example, prediction of the ability of the complex oxide catalyst will be described. When the aqueous raw material (raw material-formulated solution) is spray dried in step (II) to obtain a dry powder, part of the dry powder adheres and is deposited onto the wall surface and/or bottom within the apparatus and remains within the apparatus for a long time. Thereby, heat may be unintentionally applied to the dry powder to change the degree of oxidation and reduction. In the case where the calcining step described later is performed in an air atmosphere, it is presumed that oxidation progresses in the calcining step. Accordingly, the degree of oxidation and reduction of the dry powder hardly influences the ability of the catalyst to be produced. On the other hand, in the case where the calcining step is performed in an inert gas atmosphere, the degree of oxidation and reduction of the dry powder is likely to influence the ability of the complex oxide catalyst. Particularly, in the case where the preparation method is optimized considering the degree of oxidation and reduction of the complex oxide catalyst, the ability of the complex oxide catalyst is naturally likely to be reduced if the degree of oxidation and reduction of the dry powder is out of a suitable range. Although a detailed mechanism is unclear, the color of the dry powder changes as the degree of oxidation and reduction changes. Taking an Mo—V catalyst as an example, particularly, as the color of the dry powder changes black, the ability of the complex oxide catalyst is likely to be reduced. As a reason for this, it is thought that for example, an organic component or an inorganic component contained in the dry powder is thermally decomposed by the unintentional heating to reduce a metal element therearound, or make an oxidation reduction reaction between the metal elements. Accordingly, the absorption or reflectance spectrum of the dry powder is monitored to check the degree of change in the color, and the ability of the complex oxide catalyst can be predicted.

The method for measuring the absorption or reflectance spectrum is not particularly limited. For example, the absorption or reflectance spectrum is determined from the absorbance of the dry powder to be measured using a visible and ultraviolet spectrophotometer. As a result by extensive research by the present inventors, it was found out that the black-colored dry powder having a poor ability has an absorbance at a wavelength of not less than 500 nm larger than that of the dry powder whose color is not changed. Accordingly, the absorbance at a wavelength of not less than 500 nm and preferably at any wavelength in the range of not less than 500 nm and not more than 800 nm can be selected, and used as an index for monitoring.

Preferably, the absorption or reflectance spectrum of the dry powder is continuously measured. Here, "continuously measured" means that measurement is performed once or more every 3 months. The measurement is performed more preferably once per month, still more preferably once per week, and particularly preferably once or more per day. As the absorption or reflectance spectrum is measured more often, a risk of producing a large amount of the dry powder having an unsuitable degree of oxidation and reduction can be more reduced. Depending on the production condition, the absorption or reflectance spectrum of the dry powder hardly changes, and frequent measurement may be unnecessary. Accordingly, the frequency of the measurement may be properly set.

Moreover, in order to prevent deposition of the dry powder within the spray dryer, the measures are not limited. Preferably, a vibrator that vibrates the spray dryer, or an air knocker that gives impact to the spray dryer is attached. Alternatively, preferably, the spray drying is halted at a proper frequency, and the inside of the apparatus is washed by water or the like. The absorption spectrum or reflectance spectrum of the dry powder is preferably measured immediately after step (II) when the unintentional heating is likely to occur.

The operation condition on the air knocker provided in the dryer can be arbitrarily adjusted according to the size of the dryer, the thickness of the wall, a degree of removal of adhering objects, and the like. Examples of the operation condition include strength of a stroke of the air knocker, the frequency of the stroke, increase and reduction in the number of the air knocker to be provided, and change in the position of the air knocker to be provided. The strength of the stroke of the air knocker is preferably such strength that the wall surface and/or other portion of the dryer is not deformed and damaged even in a long-term operation. The frequency of the stroke is preferably once or more per minute, and more preferably one or more per 10 seconds. About the number and position of the air knocker to be provided, preferably, the number of the air knocker is increased in a portion in which a large amount of adhering objects is found after a long-term operation, or the air knocker provided in a portion to which objects hardly adhere is moved to a portion to which objects heavily adhere.

According to the absorption or reflectance spectrum thus measured, the following step (A) for determining the conditions in steps (I) and (II) can be performed when necessary.
[Step (A)]

Step (A) is a step of predicting the ability of the complex oxide catalyst to be finally obtained from the measured absorption or reflectance spectrum of the dry powder, and controlling the operation conditions in the respective steps based on the predicted ability of the complex oxide catalyst. By performing step (A), a catalyst having a higher ability can be efficiently obtained.

To predict the ability of the complex oxide catalyst to be finally obtained using the measured absorption or reflectance spectrum of the dry powder, a correlation between the absorption or reflectance spectrum of the dry powders obtained under different raw material preparing conditions and/or drying conditions and the ability of the complex oxide catalyst obtained from the dry powder can be used. As the absorption or reflectance spectrum of the dry powders obtained under different raw material preparing conditions and/or drying conditions, an absorbance at a specific wavelength to be obtained using an UV-visible spectrophotometer is preferably used.

The dry powders obtained under different raw material preparing conditions are the dry powders obtained, for example, by changing the procedure of dissolving or mixing in step (I) or adding an oxidizing agent or a reducing agent when the raw material for the catalyst constituting element is dissolved or dispersed in an aqueous medium, to change the state of the raw material-formulated solution such as the degree of oxidation and reduction of the catalyst component, and being further subjected to step (II). More specifically, for example, the dry powders are obtained by changing the state of the raw material-formulated solution by a method such as increasing the amount of dicarboxylic acid, adjusting the concentration of the solid content in the solution, increasing the time for the treatment, or changing the temperature in the treatment in step (I), and being further subjected to step (II).

The dry powders obtained under different drying conditions are the dry powders obtained by changing the operation condition and the like in step (II), for example, the amount of the raw material-formulated solution to be fed per unit time, the amount of the heat source for drying to be fed per unit time (for example, the amount of the air to be fed), and the temperature of the heat source for drying (for example, the temperature of the air to be fed) and/or an apparatus for preventing deposition of the dry powder, which is attached to the dryer. In the case of a centrifugal spraying method, the conditions such as the number of rotation of the disk and the size of the disk can be changed to obtain the dry powder. Alternatively, the dry powder obtained by intentionally changing the time and/or the temperature and heating the dry powder obtained in step (II) to change the color may be used.

The absorption or reflectance spectrum of the dry powders obtained under different raw material preparing conditions and/or drying conditions can be measured by the same method as above. Further, the ability of the catalyst is examined when the vapor-phase catalytic oxidation or vapor-phase catalytic ammoxidation reaction of propane or isobutane is performed using the complex oxide catalysts to be obtained by calcining the dry powders under the same condition. Examples of the ability of the catalyst to be examined include a yield, an activity, a conversion, and a yield of a byproduct, and these may be used in combination.

Next, the correlation between the absorption or reflectance spectrum of the dry powders obtained under different raw material preparing conditions and/or drying conditions and the ability of the catalyst is produced. Using the correlation, the ability of the complex oxide catalyst to be finally obtained can be predicted from the measured absorption or reflectance spectrum of the dry powder.

By step (A), the operation conditions in the respective steps can be changed according to the predicted value of the ability of the complex oxide catalyst to be finally obtained to easily obtain a complex oxide catalyst having a higher ability. Industrially, the absorption or reflectance spectrum of the dry powder is continuously monitored, and the operation condition is changed according to the absorption or reflectance spectrum described above. Thereby, a complex oxide catalyst having a high ability can be efficiently obtained.

In step (A), according to the absorption or reflectance spectrum monitored, the operation conditions in the (I) raw material formulating step and the (II) drying step described above are determined. From the viewpoint of easy control, the operation condition in the (II) drying step is preferably determined according to the absorption or reflectance spectrum.

[Step (A-1)]

Step (A-1) is a step of determining the preparing condition in step (I) according to the measured absorption or reflectance spectrum. In the step, the preparing condition is determined so as to provide a high ability of the complex oxide catalyst to be finally obtained, using a correlation between the absorption or reflectance spectrum of the dry powders obtained in step (II) from the raw material-formulated solutions obtained under different preparing conditions in step (I) and the ability of the complex oxide catalyst obtained from the dry powder.

In the step, a method for "determining the preparing condition" is not particularly limited. Examples of the method include a method of controlling the degree of oxidation and reduction of the catalyst component by the procedure of dissolving or mixing when the raw material for the catalyst constituting element is dissolved or dispersed in an aqueous medium; and a method of adding an oxidizing agent or a reducing agent. For example, the preparing condition can be determined by a method such as increasing or decreasing the amount of dicarboxylic acid, adjusting concentration of the solid content in the solution, increasing the time for the treatment, or changing the temperature in the treatment.

[Step (A-2)]

Step (A-2) is a step of determining the drying condition in step (II) according to the measured absorption or reflectance spectrum. In the step, the drying condition is determined so as to provide a high ability of the complex oxide catalyst to be finally obtained, using the correlation between the absorption or reflectance spectrum of the dry powders obtained in step (II) under different drying conditions and the ability of the complex oxide catalysts obtained from the dry powders.

In the step, the method for "determining the drying condition" is not particularly limited. In the case of using the spray dryer, examples of the method include a method of changing the operation condition such as the amount of the aqueous raw material (raw material-formulated solution) to be fed per unit time, the amount of the heat source for drying to be fed per unit time (for example, the amount of the air to be fed), and the temperature of the heat source for drying (for example, the temperature of the air to be fed), and/or an apparatus for preventing deposition of the dry powder, which is attached to the dryer. From the viewpoint of keeping the ability and physical shape and strength of the catalyst to be obtained, the method of changing the operation condition on the apparatus for preventing deposition of the dry powder is more preferred. In the case of a centrifugal spraying method, the conditions such as the number of rotation of the disk and the size of the disk may be changed. Alternatively, these may be used in combination.

The dry powder is prepared so that the content of the particle having a particle size of not more than 25 µm is preferably not more than 20% by mass, more preferably not more than 15% by mass, still more preferably not more than 10% by mass, further still more preferably not more than 5% by mass, and particularly preferably not more than 2% by mass. If the content of the particles having a particle size of not more than 25 µM is more than 20% by mass, the ability of the catalyst to be obtained is likely to be reduced, and the yield of the target product in a fluidized bed reactor is likely to be reduced.

Although the reason for reduction in the ability of the catalyst is not clear, it is thought that if the content of the particles having a particle size of not more than 25 µm is more than 20% by mass, the fluidity is likely to be reduced to produce uneven calcination within a calcining apparatus. Particularly, in continuous calcination, dry powder particles having a small particle size are reversed within the calcining apparatus, and exposed to a calcining atmosphere for a time longer than a desired time. For this reason, a proper reduction rate of the pre-stage calcined product may not be obtained in pre-stage calcination described later, or excessive calcination may be performed in the main calcination, leading to problems such as decomposition of crystal. Further, the particles of the pre-stage calcined product are likely to adhere. For this reason, adhering objects may be deposited on the wall surface of the calcining apparatus to reduce heat transfer to the inside of the apparatus, or a catalyst adhering for a long time and excessively calcined may be mixed. Thus, the reason is presumed. Here, the "pre-stage calcined product" refers to a compound produced in the pre-stage calcination step described later. For the reason above, conventionally, production of the catalyst by continuous calcination has difficulties to stably produce a catalyst having the same ability (for example, the yield of the target product) as that of the catalyst produced by calcination in batch even if the composition of the catalyst is the same. On the other hand, according to the production method in the present embodiment, a catalyst having the same ability as that of the catalyst produced by batch calcination can be obtained even by continuous calcination. The factor is not limited to those described above.

In the case where the catalyst contains Mo, Sb, or the like, a compound having a low melting point is likely to be produced. The particles having a particle size of not more than 25 μm has a proportion of the surface larger than that of the particles having a particle size of more than 25 μm. Accordingly, it is thought that the particles having a particle size of not more than 25 μm are more likely to adhere. If an excessive amount of the particles adhere, the following problems occur: the catalyst layer cannot be calcined at a sufficient calcining temperature, the amount of production cannot be secured, and the like. Accordingly, the proportion of the particles having a particle size of not more than 25 μm is preferably reduced before calcination.

The average particle size of the dry powder is more preferably 35 to 75 μm, and still more preferably 40 to 65 μm, and particularly preferably 45 to 60 μm. When the complex oxide catalyst is used in a fluidized bed catalytic reaction, at an average particle size less than 35 μm, the fluidity may be reduced to reduce the yield of the target product, or the catalyst may be easily scattered from the fluidized bed reactor to increase the loss of the amount of the catalyst. On the other hand, at an average particle size more than 75 μm, the fluidity may be reduced to reduce contact efficiency with a reaction gas, leading to reduction in the yield of the target product.

If the average particle size of the dry powder is adjusted at 35 to 75 μm and the content of the particles having a particle size of not more than 25 μm is adjusted at not more than 20% by mass, the reduction rate of the pre-stage calcined product can be adjusted in a preferred range in the calcining step. The present inventors think the mechanism as follows.

The dry powder usually contains ammonium radicals, organic acids, and inorganic acids. In the case where the dry power is calcined while an inert gas is flowed, the catalyst constituting elements are reduced when ammonium radicals, organic acids, inorganic acids are evaporated or decomposed. The ammonium radicals are evaporated and turned into ammonia gas to reduce the particles of the pre-stage calcined product from a gaseous phase. The reduction rate of the pre-stage calcined product changes depending on particularly the calcining time and calcining temperature in the pre-stage calcination described later. At a longer calcining time, or at a higher calcining temperature, reduction easily progresses, and the reduction rate is higher. In the case where a large amount of a precursor having a relatively small particle size is contained, typically, if the average particle size is less than 35 μm or the content of the particles having a particle size of not more than 25 μm is more than 20% by mass, the amount of smaller particles accompanied by the inert gas or floated along with rotation of a calcining tube and reversed in the calcining tube when the calcining tube is used is increased. As a result, there exist the particles that stagnate in the calcining tube for a time longer than a desired time, leading to difficulties to provide a reduction rate in a preferred range. It is also thought that the small particles have a large area of the surface contacting ammonia gas, and those particles are easily reduced. Conversely, at an average particle size more than 75 μm, the particles are large, and have a small area of the surface contacting ammonia gas. Those particles are difficult to reduce. As a result, it is thought that it is difficult to adjust the reduction rate in a preferred range.

Here, the content of the particles having a particle size of not more than 25 μm can be determined as follows: 20 g of the dry powder is sieved using a sieve having an opening of 25 μm and a diameter of 20 cm while a vibrator (for example, Panabrator made by Panasonic Corporation) for 3 minutes; the mass of the particles passed through the sieve and the mass of the particle left on the sieve are measured; the content of the particles having a particle size of not more than 25 μm is calculated using the following equation:

(content of the particles having a particle size of not more than 25 μm (%))=(mass of the particles passed through the sieve)÷{(mass of the particles passed through the sieve)+(mass of the particle left on the sieve)}×100

The content of the particles having a particle size of not more than 25 μm is measured after part of the dry powder is "calcined in the air at 400° C. for 1 hour," because the dry powder is prevented from being dissolved in water. Namely, "calcination in the air at 400° C. for 1 hour" is mainly for measurement, and has nothing to do with the calcining step described later. It may be thought that the particle size is substantially not changed before and after the calcination. The reduction rate of the calcined sample may be different from that of other dry powder. However, usually, the amount of the sample is extremely small amount. Accordingly, even if the sample is fed or not fed to the calcining step described later, the ability of the whole catalyst is not influenced. The object to be measured for the average particle size may not be always the dry powder. The average particle size of the pre-stage calcined product calcined may be measured when necessary.

Examples of the method for preparing particles in which the content of the particles having a particle size of not more than 25 μm is not more than 20% by mass, and the average particle size is 35 to 75 μm include a method of controlling the condition of spray drying such as the number of rotation of the atomizer, the spray drying temperature, and the amount of the raw material mixed-solution to be fed; and a method of classifying the dry powder. The method of classifying the dry powder is not particularly limited. For example, ordinary methods such as a centrifugal classifier, a wind-power classifier, a gravitational classifier, an inertial classifier, a sieve, and a cyclone can be used. Among dry and wet classifiers, a dry classifier can be suitably used from the viewpoint of preventing elution of the catalyst constituting element into the solvent, and not adversely affecting the ability of the catalyst. From the viewpoint of increasing the amount of the catalyst to be produced, the recovery rate of the dry powder in the classifying operation is preferably not less than 75% by mass, and more preferably not less than 80% by mass. Preferably, an apparatus that can be adjusted to such a condition or satisfy such a condition is selected and used.

((III) Pre-stage Calcination Step and (IV) Main Calcination Step)

Step (III) is a step of pre-stage calcining the dry powder to obtain a pre-stage calcined product.

Step (IV) is a step of main-calcining the pre-stage calcined product to obtain a calcined product having a protrusion on the surface of the particle.

Herein, step (III) and step (IV) are collectively referred as a "calcining step" in some cases.

In steps (III) and (IV), the dry powder obtained in the drying step is calcined. The condition such as the calcining temperature, the time, and the atmosphere may be properly determined from the viewpoint of removing organic components contained in the dry powder or crystal growth of the complex oxide, and is not particularly limited. In the production method according to the present embodiment, the condition such as the temperature is changed, and calcination at multi stages such as pre-stage calcination and main calcination is performed as described later.

(Method of Calcining Dry Powder)

As a calcining apparatus for calcining the dry powder, for example, a rotary furnace (rotary kiln) can be used. The shape of the calcining apparatus in which the dry powder is calcined is not particularly limited. A tubular shape (calcining tube) is preferable and a cylindrical shape is particularly preferable from the viewpoint of enabling continuous calcination. As a heating method, external heating is preferable from the viewpoint of easiness to adjust the calcining temperature in a preferred temperature raising pattern. An electric furnace can be suitably used. The size and material of the calcining tube can be properly selected depending on the calcining condition and the amount of production. The inner diameter of the calcining tube is preferably 70 to 2000 mm, and more preferably 100 to 1200 mm from the viewpoint of providing even calcining temperature distribution within the catalyst layer, and adjusting the calcining time and the amount of production at a proper value. The length of the calcining tube is preferably 200 to 10000 mm, and more preferably 800 to 8000 mm from the viewpoint of reducing the stagnation time of the dry powder and the catalyst precursor particles within the calcining tube, namely, distribution of the calcining time as much as possible, preventing distortion of the calcining tube, and adjusting the calcining time and the amount of production at a proper value.

When an impact is imparted to the calcining device (e.g., calcining tube), the thickness of the calcining device is preferably 2 mm or more, and more preferably 4 mm or more from the viewpoint that the calcining device has an enough thickness not to be broken by the impact. The thickness of the calcining device is preferably 100 mm or less, and more preferably 50 mm or less from the viewpoint that the impact is sufficiently transmitted into the calcining device. The material of the calcining device is not particularly limited as long as the calcining device preferably has heat resistance and strength to the extent not to be broken by the impact. SUS can be appropriately used as the material of the calcining tube.

Herein, the "catalyst precursor" refers to a compound produced at an intermediate stage of the calcining step.

A weir plate having a central part having a hole through which powder passes is provided vertically (or substantially vertically) to the flow of the powder in the calcining tube, and thereby the calcining tube can be also partitioned into two or more zones. A holding time of the powder in the calcining tube is easily secured by disposing the weir plate. The number of the weir plates may be one or more. The material of the weir plate is preferably a metal, and a weir plate made of the same material as that of the calcining tube can appropriately be used from the viewpoint that endurance and heat resistance with respect to a calcining atmosphere are improved. The height of the weir plate can be adjusted in accordance with a holding time which should be secured. For example, when dry powder is supplied at 250 g/hr using a rotary kiln having a calcining tube having an inner diameter of 150 mm and a length of 1150 mm and made of SUS, the height of the weir plate is preferably 5 to 50 mm, more preferably 10 to 40 mm, and still more preferably 13 to 35 mm. The thickness of the weir plate is not particularly limited, and is preferably adjusted in accordance with the size of the calcining tube. For example, in the case of a rotary kiln having a calcining tube having an inner diameter of 150 mm and a length of 1150 mm and made of SUS, the thickness of the weir plate is preferably 0.3 mm or more and 30 mm or less, and more preferably 0.5 mm or more and 15 mm or less.

In order to prevent crack and crazing or the like of the dry powder and to uniformly calcine the dry powder, the calcining tube is preferably rotated. The rotation speed of the calcining tube is preferably 0.1 to 30 rpm, more preferably 0.5 to 20 rpm, and still more preferably 1 to 10 rpm. In a rotary furnace having a calcining tube, the furnace preferably has a vertical inclination to the direction of rotation. More preferably, the rotary furnace is inclined so that a feed side is raised and a powder discharge side after calcination of the powder is lowered. The angle of elevation viewed from the powder discharge side is preferably not less than 0.3° and not more than 15°, and more preferably not less than 0.3° and not more than 5°.

For the calcination of the dry powder, preferably, the heating temperature of the dry powder is continuously or intermittently raised to a temperature in the range of 550 to 700° C. from a temperature lower than 400° C.

A calcining atmosphere may be under an air atmosphere or under an air flow. However, at least a portion of the calcination is preferably carried out while an inert gas which does not substantially contain oxygen, such as nitrogen, flows from the viewpoint of adjusting to preferable oxidation/reduction state. In the case where calcination is performed in batch, the amount of an inert gas to be fed is not less than 50 N liters/hr per 1 kg of the dry powder from the viewpoint of adjustment to a preferred state of oxidation and reduction. The supplied amount of the inert gas is preferably 50 to 5000 N liters/hr, and more preferably 50 to 3000 N liters/hr. Here, "N liter" means a liter measured under normal temperature and pressure conditions, that is, at 0° C. and 1 atm.

In the case where calcination is continuously performed, the amount of an inert gas to be fed is not less than 50 N liters per 1 kg of the dry powder from the viewpoint of adjustment to a preferred state of oxidation and reduction. The amount is preferably 50 to 5000 N liters, and more preferably 50 to 3000 N liters. On this occasion, the flows of inert gas and dry powder may be in the form of a counter flow or a parallel flow. However, counter flow contact is preferable in consideration of gas components generated from the dry powder and a trace amount of air entering together with the dry powder. Particularly, in the case where in the raw material formulating step above, the method for adding the hydrogen peroxide solution to the aqueous mixed-solution (A) is used, and the step of oxidizing molybdenum, vanadium, and antimony in the solution to as high an oxidation number as possible is performed to obtain the raw material-formulated solution, the dry powder is preferably calcined while an inert gas substantially containing no oxygen such as nitrogen is flowed.

Other than moisture, the dry powder usually contains ammonium radicals, organic acids, inorganic acids, and the like. In the case where calcination is performed while the inert gas substantially containing no oxygen is flowed, the catalyst constituting elements are reduced when ammonium radicals, organic acids, inorganic acids, and the like are evaporated or decomposed. In the case where the catalyst constituting element in the dry powder has an almost highest oxidation number, in order to obtain the reduction rate of the catalyst in a desired range, only reduction is performed in the calcining step, and this is industrially simple.

On the other hand, as described later, an oxidizing component or a reducing component may be added into the calcining atmosphere to obtain the reduction rate of the pre-stage calcined product in a desired range. In the production method according to the present embodiment, the reduction rate of the pre-stage calcined product to be obtained is 8 to 12%, preferably 9 to 11%, and more preferably 9.5 to 11%. Preferably, calcination is performed so that the specific surface area of the calcined product is 7 to 20 $m^2/g$. The specific surface area is more preferably 10 to 16 $m^2/g$. If the specific surface area of the calcined product is 7 to 20 $m^2/g$, effects of more sufficient activity, suppression of deterioration, and a higher yield are likely to be obtained. Moreover, an effect of adding the molybdenum compound in order to keep the yield in the oxidation reaction or the ammoxidation reaction is more sufficiently demonstrated, and no rapid reduction is shown. Accordingly, the amount and frequency of the molybdenum compound to be added tend to be able to be reduced. Although the reason is not clear, it is presumed that at a specific surface area of the calcined product less than 7 $m^2/g$, an active species concerning the reaction has a small active surface, and the effect of adding the molybdenum compound is difficult to demonstrate. It is also presumed that at a specific surface area of the calcined product more than 20 $m^2/g$, the active species has a large active surface while molybdenum is lost from the active surface fast. The factor is not limited to this.

The reduction rate of the pre-stage calcined product is represented by the following equation (D):

$$\text{Reduction rate (\%)} = (n_0 - n)/n_0 \times 100 \quad \text{(D)}$$

(wherein n is the number of oxygen atoms that satisfy a valence of constituent elements other than oxygen in the pre-stage calcined product, and $n_0$ is the number of oxygen atoms needed when the respective constituent elements other than oxygen in the pre-stage calcined product have the highest oxidation number).

Specifically, the dry powder is calcined on the calcining condition as follows: the heating temperature of the dry powder is raised from a temperature lower than 400° C., and continuously or intermittently to a temperature in the range of 450 to 700° C. At this time, the calcining condition is adjusted so that the reduction rate of the pre-stage calcined product calcined when the heating temperature reaches 400° C. is 8 to 12%.

The reduction rate of the pre-stage calcined product is usually influenced by the amount of organic components of oxalic acid contained in the dry powder, the amount of ammonium radicals derived from ammonium salts in the raw material, the temperature raising rate at the time of starting calcination, the amount of the inert gas in the case of calcination under the inert gas atmosphere, and the temperature and the time in the case of calcination under the air atmosphere. In order to obtain the reduction rate of the pre-stage calcined product of 8 to 12%, it is important to raise the temperature in the calcination from a temperature lower than 400° C., and decompose oxalic acid radicals and ammonium radicals in the dry powder to almost complete production of gas; thus, the reduction rate of the pre-stage calcined product calcined when the heating temperature reaches 400° C. is obtained in the range of 8 to 12%.

The specific surface area of the calcined product is influenced by the temperature and time of final calcining (heating) and the amount of silica to carry the catalyst in the case where the catalyst is carried on silica, and particularly greatly influenced by the reduction rate when the heating temperature reaches 400° C. and the final calcining temperature. The calcination at a final stage is performed at 450° C. to 700° C. for 0.5 hours to 20 hours. As the final calcining temperature is higher and the time is longer, the specific surface area is smaller. If the reduction rate when the heating temperature reaches 400° C. is lower, the specific surface area of the calcined product is likely to be smaller. If the reduction rate when the heating temperature reaches 400° C. is higher, the specific surface area is likely to be larger. Although the reason is not clear, in the case where the calcination is performed in two stages of the pre-stage calcination and the main calcination and the temperature in the main calcination is kept constant, the higher the highest calcining temperature in the pre-stage calcination is, the larger the specific surface area is. The lower the highest calcining temperature in the pre-stage calcination is, the smaller the specific surface area is.

In the case where calcination is performed by the rotary kiln, the amount of the dry powder to be fed can be adjusted during the calcination to adjust the specific surface area of the calcined product. If a small amount of the dry powder is fed, the dry powder stagnates within the system for a longer time. For this reason, reduction of the dry powder progresses by a reducing gas such as ammonia, which is produced by heating the dry powder in the calcining tube. As a result, the reduction rate is higher, and the specific surface area of the catalyst to be obtained after the main calcination is larger. Conversely, a large amount of the dry powder is fed, the reduction rate is lower, and the specific surface area of the catalyst is smaller. Alternatively, the specific surface area can be adjusted by the amount of nitrogen during the pre-stage calcination. If the amount of nitrogen is increased, the component gas that reduces the pre-stage calcined product during calcination is quickly discharged to the outside of the system. Accordingly, it is thought that the pre-stage calcined product is difficult to reduce, resulting a small specific surface area of the calcined product. Conversely, if the amount of nitrogen is reduced, the reduction rate is higher, and the specific surface area of the calcined product is larger.

In order to obtain the specific surface area of the calcined product of 7 to 20 $m^2/g$, preferably, the reduction rate when the heating temperature reaches 400° C. is in the range of 8 to 12%, and the final calcining temperature is 450° C. to 700° C.

The calcining step includes the pre-stage calcination step and the main calcination step. Preferably, the pre-stage calcination is performed at a temperature in the range of 250 to 400° C., and the main calcination is performed at a temperature in the range of 450 to 700° C. The pre-stage calcination and the main calcination may be successively performed; or the pre-stage calcination may be once completed, and the main calcination may be newly performed. Alternatively, the pre-stage calcination and the main calcination each may have several stages.

In the case where the reduction rate of the pre-stage calcined product during the calcination is measured, the sample may be extracted from the calcining apparatus at the temperature. However, the sample may contact the air at a high temperature to be oxidized, and the reduction rate may be changed. Preferably, after the calcining apparatus is cooled to room temperature, the pre-stage calcined product is extracted from the calcining apparatus, and used as a representative sample. Examples of the method for controlling the reduction rate when the heating temperature reaches 400° C. in a desired range specifically include a method of changing the temperature in the pre-stage calcination, a method of adding an oxidizing component such as oxygen to an atmosphere during calcination, or a method of adding a reducing component to an atmosphere during calcination. Moreover, these may be used in combination.

The method of changing the temperature in the pre-stage calcination is to change the calcining temperature in the pre-stage calcination, and a method of changing the reduction rate when the heating temperature reaches 400° C. Usually, the reduction rate is likely to be reduced by reducing the temperature in the pre-stage calcination, and increased by raising the temperature in the pre-stage calcination. For this reason, the temperature in the pre-stage calcination can be changed to control the reduction rate. The reduction rate can also be controlled by increasing or reducing the amount of nitrogen to be fed in the case of using nitrogen, increasing or reducing the amount of the dry powder to be fed, and increasing or reducing the number of rotation of the rotary kiln in the calcination using the rotary kiln. It is thought that if the amount of the nitrogen to be fed is increased, in the oxidized components evaporated from the dry powder by heating the furnace, the proportion of the oxidized components discharged to the outside of the system without being oxidized by a metal oxide that exists within the calcining furnace (the metal oxide is reduced) is higher, and therefore the calcined product is difficult to reduce. It is also thought that if the amount of the dry powder to be fed is reduced, reduction progresses in the rotary kiln because the catalyst stagnates for a longer time in the rotary kiln. It is also thought that in the case of the rotary kiln, if the number of rotation thereof is reduced, the moving speed of the catalyst within the rotary kiln is reduced; for this reason, reduction progresses because the catalyst contacts a larger amount of the oxidized components for a longer time.

The method of adding an oxidizing component such as oxygen to an atmosphere during calcination in order to control the reduction rate when the heating temperature reaches 400° C. in a desired range is a method that can be used when the reduction rate is reduced. The calcination at this stage is the pre-stage calcination. The oxidizing component added into the atmosphere during the calcination refers to an oxidizing component in the inert gas to be fed to the calcining apparatus. The amount of the oxidizing component to be added is managed by the concentration of the inert gas fed into the calcining apparatus. By addition of the oxidizing component, the reduction rate can be controlled. In the case where the oxidizing component is oxygen, the air (or the inert gas containing the air) can be fed to the calcining apparatus, and oxygen in the air can be used as the oxidizing component.

The method of adding a reducing component to an atmosphere during calcination in order to control the reduction rate when the heating temperature reaches 400° C. in a desired range is a method that can be used when the reduction rate is increased. The reducing component added into the atmosphere during the calcination refers to a reducing component in the inert gas to be fed to the calcining apparatus. The amount of the reducing component to be added is managed by the concentration in the inert gas fed into the calcining apparatus. By addition of the reducing component, the reduction rate can be controlled. Usually, examples of the reducing component include hydrogen, prussic acid, methane, ethane, propane, carbon monoxide, nitrogen monoxide, and ammonia. Among these, one thereof can be used alone, or a plurality of gases can be used in combination. Among these, the gas containing ammonia as a principal component is preferably added.

In the case where the reduction rate of the pre-stage calcined product when the heating temperature reaches 400° C. is not a desired reduction rate, the total amount of a necessary oxidizing substance or reducing substance can be calculated from the difference between the actual reduction rate and the desired reduction rate, and added to the atmosphere during the calcination. An oxidizing component (for example, oxygen) or a reducing component (for example, ammonia) may be added into the calcining atmosphere under a flow of the inert gas, if desired, in order to adjust the reduction rate. In determination of the reduction rate, the value of the $(n_0-n)$ in the equation (2) is obtained by oxidation-reduction titration of a sample with $KMnO_4$. In both of the pre-stage calcined product before the calcination is completed and the calcined product after the calcination is completed, the value of $(n_0-n)$ can be determined by oxidation-reduction titration. In the measurement by oxidation-reduction titration, however, the condition on the pre-stage calcined product before the main calcination is completed is different from that on the calcined product after the main calcination is completed. In each of the pre-stage calcined product before the main calcination is completed and the calcined product after the main calcination is completed, an example of a measurement method is shown in below.

In the pre-stage calcined product before the calcination is completed, the measurement is performed as follows.

Approximately 200 mg of the pre-stage calcined product is weighed and placed in a beaker. Further, an excessive amount of a $KMnO_4$ aqueous solution having a known concentration is added. Further, 150 mL of pure water at 70° C. and 2 mL of 1:1 sulfuric acid (namely, a sulfuric acid aqueous solution obtained by mixing concentrated sulphuric acid with water in a volume ratio of 1/1) are added, and the beaker is covered with a watch glass. The mixed-solution is stirred in a hot water bath at 70° C.±2° C. for 1 hr to oxidize the sample. At this time, $KMnO_4$ excessively exists, and non-reacted $KMnO_4$ exists in the solution. For this, it is checked that the color of the solution is violet. After oxidation is completed, the solution is filtered by a filter paper to recover the total amount of the filtrate. An excessive amount of a sodium oxalate aqueous solution having a known concentration is added to $KMnO_4$ that exists in the filtrate, and heated and stirred so that the temperature of the solution is 70° C. It is checked that the solution becomes colorless and transparent, and 2 mL of 1:1 sulfuric acid is added. Stirring is continued while the temperature of the solution is kept at 70° C.±2° C., and titrated by a $KMnO_4$ aqueous solution having a known concentration. When the color of the solution keeps light pink for approximately 30 seconds by $KMnO_4$, it is the end point.

From the total amount of $KMnO_4$ and the total amount of $Na_2C_2O_4$, the amount of $KMnO_4$ consumed in oxidation of the sample is determined. From the value, $(n_0-n)$ is calculated, and the reduction rate is determined based on the obtained value.

In the calcined product after the main calcination is completed, the measurement is performed as follows.

Approximately 200 mg of the calcined product ground by an agate mortar is weighed and placed in a beaker. 150 mL of pure water at 95° C. and 4 mL of 1:1 sulfuric acid (namely, a sulfuric acid aqueous solution obtained by mixing concentrated sulphuric acid with water in a volume ratio of 1/1) are added. Stirring is continued while the temperature of the solution is kept at 95° C.±2° C., and titrated by a $KMnO_4$ aqueous solution having a known concentration. At this time, although the color of the solution temporarily becomes violet by titration of $KMnO_4$, $KMnO_4$ is slowly titrated little by little so as not to continue the color of violet for not less than 30 seconds. The amount of the solution is reduced by evaporation of water. For this reason, pure water at 95° C. is added so that the amount of the solution is kept constant. When the color of the solution keeps light pink for approximately 30 seconds by $KMnO_4$, it is the end point.

Thus, the amount of $KMnO_4$ consumed in oxidation of the sample is determined. From the value, $(n_0-n)$ is calculated, and the reduction rate is determined based on the obtained value.

Other than the measurement method, the measurement can be performed in the pre-stage calcined product before the main calcination is completed and the calcined product after the main calcination is completed, as follows.

On the condition in which the constituent elements in the sample are not volatilized nor lost, the sample is heated to a temperature higher than the calcining temperature at which the pre-stage calcined product or the calcined product is calcined, and complete oxidation by oxygen is performed. The increased mass (the amount of oxygen bonded) is determined. From this, the value of $(n_0-n)$ is determined. Based on this, the reduction rate is determined.

The method for performing the calcining in an inert gas or a preferred oxidation/reduction atmosphere is not particularly limited. Preferably, the calcining apparatus that has a proper sealing structure, and can sufficiently block contact with an open air is used.

The pre-stage calcination is performed preferably under a flow of an inert gas at a temperature in the pre-stage calcination in the range of preferably 250° C. to 400° C., and more preferably of 300° C. to 400° C. from the viewpoint of easiness to adjust the catalyst to obtained in a preferred state of oxidation and reduction and improvement in the ability of the catalyst. Preferably, the temperature in the pre-stage calcination is kept at a constant temperature in the range of 250° C. to 400° C. The temperature may be changed in the range of 250° C. to 400° C., or mildly raised or lowered. The retention time of the heating temperature is preferably not less than 30 minutes, and more preferably 3 to 12 hours from the viewpoint of easiness to adjust the catalyst to be obtained in a preferred state of oxidation and reduction and improvement in the ability of the catalyst. As the pattern of the temperature that reaches the temperature in the pre-stage calcination, the temperature may be linearly raised, or may be raised as if an arc projected upward or downward is drawn. Moreover, the temperature may be lowered at some time during raising the temperature, or the temperature may be repeatedly raised and lowered. Further, an endothermic reaction occurs during raising the temperature by the component contained in the dry powder and/or the catalyst precursor, and the temperature may be temporarily lowered.

The average temperature raising rate at the time of raising the temperature to the temperature in the pre-stage calcination is not particularly limited. The average temperature raising rate is usually approximately 0.1 to 15° C./min, preferably 0.5 to 5° C./min, and more preferably 1 to 2° C./min from the viewpoint of easiness to adjust the catalyst to be obtained in a preferred state of oxidation and reduction and improvement in the ability of the catalyst.

The main calcination can be performed preferably under a flow of an inert gas at a temperature of preferably of 450 to 700° C., and more preferably of 620 to 700° C. from the viewpoint of easiness to adjust the catalyst to be obtained in a preferred state of oxidation and reduction, sufficient formation of a crystal structure active to the reaction, and improvement in the ability of the catalyst. The calcining temperature in the main calcination (main-calcining temperature) is preferably kept at a constant temperature in the range of 620 to 700° C. The temperature may be changed or mildly raised or lowered in the range of 620 to 700° C. Moreover, the temperature may be lowered at some time during raising the temperature, or the temperature may be repeatedly raised and lowered. An endothermic reaction occurs during raising the temperature by the component contained in the pre-stage calcined product, and as a result, the temperature may be lowered in the pattern.

A protrusion is produced on the surface of the particle of the calcined product subjected to the main calcination step. As a result of examination by the present inventors, it is clear that although the composition of the protrusion depends on the composition at the time of preparation and/or the calcining condition, a relatively large amount of Mo and Sb are contained in the composition of the protrusion, and the ratio thereof is close to Mo:Sb=10:2 or 10:4 (atomic ratio). If the protrusion having such a composition exists in the reactor in the vapor-phase catalytic oxidation reaction or the vapor-phase catalytic ammoxidation reaction of propane or isobutane, the side reaction is easily caused. Desirably, the protrusion is removed before the reaction. Accordingly, in the production method according to the present embodiment, the composition of the raw material-formulated solution to be formulated is designed assuming that the protrusion is removed. In order to optimize the composition of the catalyst to be finally obtained, it is important to sufficiently produce the protrusion in the calcining step, and sufficiently remove the protrusion.

According to examination by the present inventors, the degree of the protrusion to be produced has a correlation with the specific surface area of the calcined product. Although the reason is not clear, the amount of the protrusion is likely to be larger when the specific surface area is smaller. As described above, if the component of the protrusion that easily causes the side reaction is removed, the ability of the catalyst is improved. Then, to sufficiently remove the protrusion in the step of removing the protrusion described later, preferably, adjustment is performed so that a proper amount of the protrusion is produced in the calcining step. Preferably, adjustment is performed so that a complex oxide having the same composition as that of the protrusion does not remain within the catalyst, and the calcined product is obtained at a small surface area and a proper specific surface area in which the ability of the catalyst is not reduced. The catalyst adjusted at a proper specific surface area can keep a stably high ability not only for a short period of time but also for a long period of time. Although the reason is not clear, in the case where the protrusion cannot be sufficiently removed, it is thought that the components of the protrusion that remain within the catalyst or the surface thereof may be partially or entirely fused in the reaction to reduce the fluidity of the catalyst or the ability thereof due to cloggings of the pores of the surface because the components of the protrusion have a low melting point. According to the highest calcining temperature in the main calcination and the amount of the pre-stage calcined product to be fed in the main calcination, the specific surface area can be adjusted. If the highest calcining temperature in the main calcination is raised, sintering of the silica component contained in the pre-stage calcined product progresses. Accordingly, the specific surface area is reduced. If the amount of the pre-stage calcined product to be fed is reduced, the pre-stage calcined product stagnates in the rotary kiln for a longer time. Accordingly, sintering of silica progresses, and the specific surface area is reduced. Although the reason is not clear, at an excessively small specific surface area of the calcined product, the amount of the protrusion is increased to reduce the amount of production. At an excessively large specific surface area of the calcined product, the amount of the protrusion is reduced, and the ability of the catalyst is also reduced. From the viewpoint above, in the production method according to the present embodiment, the specific surface area of the calcined product is adjusted to preferably 7 to 20 m$^2$/g, and more preferably 10 to 16 m$^2$/g.

The specific surface area is determined by a BET single point method using a Gemini 2360 (trade name) made by Micrometrics Instrument Corporation.

The specific surface area of the calcined product can be adjusted by the calcining temperature. A calcined product having a specific surface area can be obtained by increasing or reducing the temperature of the pre-stage calcination or a specific surface area. Preferably, the calcining temperature in the main calcination easily influenced by the specific surface area is adjusted to obtain the target calcined product having a specific surface area.

The time for the main calcination is preferably 0.5 to 20 hours, and more preferably 1 to 15 hours. In the case where the calcining tube is partitioned by a weir plate, the pre-stage calcined product and/or the calcined product continuously passes through at least two zones, preferably 2 to 20 zones, and more preferably 4 to 15 zones from the viewpoint of ensuring the stagnation time of the dry powder or the like in the calcining tube. The temperature can be controlled using one or more controller. In order to obtain the desired calcining pattern, a heater and a controller are preferably provided in each of the zones partitioned by these weirs to control the temperature. For example, in the case where seven weir plates are provided so that the length of the portion of the calcining tube placed within the heating furnace is equally divided into eight zones, and the calcining tube having the eight divided zones is used, preferably, the set temperature in each of the eight zones is controlled by the heater and the controller provided in each of the eight zones so that the temperature of the pre-stage calcined product and/or the main-calcined product is controlled at the desired calcining temperature pattern. For example, in the case where seven weir plates are provided so that the length of the portion of the calcining tube placed within the heating furnace is equally divided into eight zones, and the calcining apparatus having the eight divided zones is used, adjustment can be performed as follows in order to obtain the desired calcining pattern. In the pre-stage calcination, preferably, the temperature of the thermocouple inserted into the central portion of the pre-stage calcined product that stagnates within each of the zones in the calcining apparatus is adjusted so that the zone 1: 120 to 280° C., the zone 2: 180 to 330° C., the zone 3: 250 to 350° C., the zone 4: 270 to 380° C., the zone 5: 300 to 380° C., the zone 6: 300 to 390° C., the zone 7: 320 to 390° C., and the zone 8: 260 to 380° C. from the feeding side of the pre-stage calcined product. Similarly, in the main calcination, adjustment is preferably performed so that the zone 1: 360 to 560° C., the zone 2: 450 to 650° C., the zone 3: 600 to 700° C., the zone 4: 620 to 700° C., the zone 5: 580 to 700° C., the zone 6: 480 to 690° C., the zone 7: 450 to 630° C., and the zone 8: 370 to 580° C.

An example is taken in which the composition at the time of preparation is $Mo_1V_{0.209}Sb_{0.236}Nb_{0.091}W_{0.027}Ce_{0.005}O_x$, the dry powder having the content of silica as the carrier of 47.0% by mass in the total dry powder is continuously calcined using the calcining tube, and the temperature of the pre-stage calcination is 350° C. To obtain a calcined product having a specific surface area of 7 to 20 m$^2$/g, the temperature in the main calcination is preferably 600 to 700° C. To obtain a calcined product having a specific surface area of 10 to 16 m$^2$/g, the temperature in the main calcination is preferably 640 to 700° C. The calcined product having a specific surface area of 7 to 20 m$^2$/g has a large amount of the particles of the protrusion on the outer surface thereof, and the larger amount of the protrusion can be removed in the step of removing the protrusion. Accordingly, the composition of the catalyst to be finally obtained is easily controlled to the optimal value as designed.

For example, while an SUS calcining tube having an inner diameter of 500 mm, a length of 4500 mm, and a thickness of 20 mm, and having an inside partitioned into eight by weir plates is rotated at 6 rpm, the highest calcining temperature in the pre-stage calcination is 350° C. Further, while the amount of the inert gas (nitrogen gas) within the system is flowed at 1050 NL/min in total, the dry powder is fed at a rate of 35 kg/hr to perform the pre-stage calcination. Subsequently, while the same SUS calcining tube is rotated at 6 rpm, strokes are given to the main-calcining tube (calcining tube for performing the main calcination) at 6 times/min using a hammer or the like, and the highest calcining temperature in the main calcination is 650° C. Further, while the amount of the inert gas (nitrogen gas) within the system is flowed at 667 NL/min in total, the pre-stage calcined product is fed at a rate of 20 kg/hr to perform the main calcination. In this case, the reduction rate of the pre-stage calcined product can be 8 to 12%, and the specific surface area of the calcined product can be 7 to 20 m$^2$/g, and more preferably 10 to 16 m$^2$/g. In this case, if the amount of the dry powder or the pre-stage calcined product to be fed is changed, in order to obtain a reduction rate of the pre-stage calcined product of 8 to 12% and a specific surface area of the calcined product of 7 to 20 m$^2$/g and more preferably 10 to 16 m$^2$/g, for example, the condition is preferably changed as follows.

In the pre-stage calcination, an example of a method for optimizing mainly the reduction rate will be shown. In the case where the amount of the dry powder to be fed is increased from 35 kg/hr to 60 kg/hr, in order to obtain a reduction rate of 8 to 12%, the inert gas introduced into the system is preferably increased to 1500 to 1800 NL/min. In the case where the amount of an inert gas to be fed is not increased, the stagnation time of the dry powder in the calcining tube is preferably increased in combination of the methods by increasing the height of the weir, increasing the number of weirs, increasing the length of the calcining tube, and increasing the inner diameter of the calcining tube. Also preferably, the highest calcining temperature in the pre-stage calcination is increased. It is thought that if the number of rotation of the rotary kiln is reduced, it takes a longer time for the dry powder in the vicinity of the interface of the gas flowing in the calcining tube to move to the lower portion of the powder layer in which the dry powder is difficult to contact the flowed gas, and the reduction reaction by the reducing gas easily progresses in the upper portion of the powder layer. Accordingly, by reducing the number of rotation of the rotary kiln, the reduction rate of the pre-stage calcined product can also be increased.

Conversely, in the case where the amount of the dry powder to be fed is reduced from 45 kg/hr to 20 kg/hr, in order to obtain a reduction rate of 8 to 12%, preferably, the inert gas introduced into the system is reduced to 400 to 800 NL/min. In the case where the amount of an inert gas to be fed is not reduced, the stagnation time of the dry powder in the calcining tube is preferably reduced by reducing the height of the weir, reducing the number of weirs, reducing the length of the calcining tube, and reducing the inner diameter of the calcining tube. Also preferably, the highest calcining temperature in the pre-stage calcination is reduced. It is thought that if the number of rotation of the rotary kiln is increased, it takes a shorter time for the dry powder in the vicinity of the interface of the gas flowing in the calcining tube to move to the lower portion of the powder layer in which the dry powder is difficult to contact the flowed gas, and the reduction reaction by the reducing gas is difficult to progress in the upper portion of the powder layer. Accordingly, by increasing the number of rotation of the rotary kiln, the reduction rate of the pre-stage calcined product can also be reduced.

The specific surface area of the pre-stage calcined product can be adjusted to some extent according to the condition of the pre-stage calcination, but not as much as in the case of the specific surface area of the calcined product. Although the reason is not clear, the reduction rate is proportional to the specific surface area, and by performing the same management as above, the range of the specific surface area is easily optimized. However, adjustment of the specific surface area of the calcined product largely depends on the calcining method in the main calcination.

An example will be shown below in which a calcined product having a proper specific surface area is obtained from the pre-stage calcined product having a reduction rate of 8 to 12% in the main calcination.

In the main calcination step, while an SUS calcining tube having an inner diameter of 500 mm, a length of 4500 mm, and a thickness of 20 mm, and having an inside partitioned into eight by weir plates is rotated at 6 rpm, the highest calcining temperature in the main calcination is 650° C. Further, while the amount of inert gas (nitrogen gas) within the system is flowed at 667 NL/min in total, the pre-stage calcined product is fed at a rate of 20 kg/hr to perform the main calcination. In this case, if the specific surface area of the calcined product is controlled in the range of 7 to 20 m$^2$/g, for example, the operation as follows is preferably performed. For example, in the case where the amount of the pre-stage calcined product to be fed into the main-calcining tube is reduced to 10 kg/hr, in order to keep a proper range of the specific surface area, the amount of the inert gas (nitrogen gas) is preferably adjusted to 250 to 400 NL/min. Moreover, the specific surface area can be adjusted in the target range more simply by one of the methods of reducing the height of the weir, reducing the diameter of the calcining tube, reducing the length of the calcining tube, increasing the inclination of the angle of the calcining tube to be provided (however, the downstream side is lowered), reducing the width of the highest temperature region within the calcining tube (the "highest temperature region" here refers to the temperature range of 300 to 390° C. during the pre-stage calcination and the temperature range of 600 to 700° C. in the main calcination.) in the longitudinal direction, and reducing the highest temperature in the main calcination, or in arbitrary combination thereof. On the other hand, in the case where the amount of the pre-stage calcined product to be fed into the main-calcining tube is increased to 40 kg/hr, the amount of the inert gas (nitrogen gas) is preferably adjusted to 1000 to 1600 NL/min. Moreover, the specific surface area can be adjusted in the target range by one of the methods of increasing the weir, increasing the diameter of the calcining tube, increasing the length of the calcining tube, reducing the inclination of the angle of the calcining tube to be provided (however, the downstream side is lowered), reducing the width of the highest temperature region within the calcining tube in the longitudinal direction, increasing the highest calcining temperature in the main calcination, and the like, or in arbitrary combination thereof. Thus, even if the condition is changed in the pre-stage calcination, the condition in the main calcination can be adjusted to keep a proper reduction rate and a proper specific surface area.

The calcining temperature of 650° C. greatly exceeds the melting points of oxides of the constituent metals. For this reason, a large amount of oxides adhere to the wall surface of the calcining tube. Then, the stagnation time of the pre-stage calcined product is preferably increased by giving strokes to the main-calcining tube using a hammer or the like, increasing the number of strokes, or increasing the number of rotation of the rotary kiln (rotary furnace). The rate of the number of strokes or the number of rotation to be increased can be arbitrarily set from a mass balance between the amount of the pre-stage calcined product to be fed to the main-calcining tube and the amount of the calcined product to be discharged from the main-calcining tube. An oxidizing component (for example, oxygen) or a reducing component (for example, ammonia) may be added to the calcining atmosphere under a flow of the inert gas, if desired.

As the pattern of raising the temperature to the main-calcining temperature, the temperature may be linearly raised, or may be raised as if an arc projected upward or downward is drawn. Moreover, the temperature may be lowered at some time during raising the temperature, or the temperature may be repeatedly raised and lowered. An endothermic reaction occurs during raising the temperature by the component contained in the pre-stage calcined product, and as a result, the temperature may be lowered in the pattern.

The average temperature raising rate during raising the temperature at which the temperature reaches the main-calcining temperature is not particularly limited, and preferably 0.5 to 8° C./min. The average temperature falling rate after the main calcination is completed is preferably 0.05 to 50° C./min, and more preferably 0.05 to 20° C./min from the viewpoint of sufficient formation of a crystal structure active to the reaction and improvement in the ability of the catalyst.

Preferably, the temperature is kept once at a temperature lower than the main-calcining temperature and annealing is performed from the viewpoint of sufficient formation of a crystal structure active to the reaction and improvement in the ability of the catalyst. The temperature to be kept is a temperature 5° C., preferably 10° C., and more preferably 50° C. lower than the main-calcining temperature. From the same viewpoint as above, the time to keep is preferably not less than 0.5 hours, more preferably not less than 1 hour, still more preferably not less than 3 hours, and particularly preferably not less than 10 hours. As the stage of annealing, the calcined product may be annealed after the main calcination.

When the main calcination is carried out anew once the pre-stage calcination has been completed, a low temperature treatment can be performed prior to the main calcination. A time required for the low temperature treatment, that is, a time required for reducing the temperature of the pre-stage calcined product and/or the calcined product and raising the temperature to the calcining temperature can appropriately be adjusted by the size, the thickness, and the material of the calcining device, a catalyst production amount, a series of periods for continuously calcining the pre-stage calcined product and/or the calcined product, and a fixing rate and a fixing amount, or the like. The time needed for the low temperature treatment is preferably 30 days or less, more preferably 15 days or less, still more preferably 3 days or less, and particularly preferably 2 days or less during a series of continuous calcination of the calcined product from the viewpoint of sufficiently removing the pre-stage calcined product and/or the calcined product adhering to the wall surface of the calcining tube, stably keeping the temperature of the oxide layer, and improving the ability of the catalyst to be obtained. The temperature of the oxide layer refers to a temperature measured by a thermocouple inserted into the particle-like pre-stage calcined product and/or main-calcined product deposited within the calcining apparatus. Further, for example, when the pre-stage calcined product is supplied at a rate of 35 kg/hr while a rotary kiln having a calcining tube having an inner diameter of 500 mm, a length of 4500 mm, and a thickness of 20 mm and made of SUS is rotated at 6 rpm, and the main calcining temperature is 645° C., the step of lowering a temperature to 400° C. and raising the temperature to 645° C. can be performed in about 1 day after the pre-stage calcination. When calcination is continuously performed for 1 year, the calcination can be performed by carrying out such low temperature treatment once a month while a temperature of an oxide layer is stably maintained.

Moreover, if impact is given to the calcining apparatus in the calcining step, an effect of cracking adhering lumps is likely to be enhanced. In the case where the low temperature treatment is performed, the impact given to the calcining apparatus is preferable because cracked lumps are likely to be easily removed from the calcining apparatus.

The impact given to the calcining apparatus depends on the depth of the layer of the pre-stage calcined product fed into the calcining apparatus, the diameter, length, thickness, and material of the calcining apparatus (for example, the calcining tube), the material, kind, shape, and position of the apparatus to which the impact is given, and the frequency of giving the impact. Preferably, the impact given to the calcining apparatus is properly set depending on these.

The vibration acceleration in the position to which the impact is given (hereinafter, referred to as an impact point.) is preferably not less than $0.1$ m/s$^2$, and more preferably not less than $10$ m/s$^2$ from the viewpoint of sufficiently reducing adhering objects to the inner wall of the calcining apparatus. Moreover, the vibration acceleration is preferably not more than $3000$ m/s$^2$, and more preferably not more than $300$ m/s$^2$ from the viewpoint of preventing damage of the calcining apparatus, and preventing disorder of the flow of the powder flowing within the calcining apparatus.

In the present embodiment, the "vibration acceleration" of the impact given to the calcining apparatus means the average value of values measured in positions located parallel to the flow direction of the powder and $L/4$, $3L/8$, and $L/2$ away from an inlet for the powder in the calcining apparatus to the whole length L of the calcining apparatus in the case where the calcining apparatus is the calcining tube. The position to be measured is the same position as the impact point in the direction of the cross section of the calcining apparatus. The vibration acceleration can be measured by a vibrometer attached to the calcining apparatus. As the vibrometer, an MD220 (trade name) made by ASAHI KASEI TECHNOSYSTEM CO., LTD. can be used.

The method for giving impact is not particularly limited, and an air knocker, a hammer, a hammering apparatus, and the like can be suitably used. The material for a portion directly contacting the calcining apparatus in the end for giving strokes is not particularly limited as long as the material has sufficient heat resistance. For example, impact-resistant resins and metals can be usually used. Among these, metals are preferred. The metals having hardness not to damage or deform the calcining apparatus are preferable. Copper and SUS can be suitably used. The position to which the impact is given is not particularly limited, and the impact can be given to any position convenient to operation. Preferable is a position not covered with the heating furnace in the calcining apparatus because the impact can be given directly to the calcining apparatus without loss.

The position to which the impact is given may be one or several positions. In the case where the calcining tube is used as the calcining apparatus, in order to efficiently conduct the vibration, the impact is preferably given from the direction perpendicular to the rotation axis of the calcining tube. The frequency of giving the impact is not particularly limited. Preferably, the impact is constantly given to the calcining apparatus because adhering objects within the calcining apparatus are likely to be reduced well. Here, "the impact is constantly given" means that the impact is given preferably once per not less than 1 second and not more than 1 hour, more preferably once per not less than 1 second and not more than 1 minute. Preferably, the frequency of giving the impact is properly adjusted depending on the vibration acceleration, the depth of the layer of the pre-stage calcined product fed into the calcining apparatus, the diameter, length, thickness, and material of the calcining apparatus (for example, the calcining tube), and the material, kind, and shape of the apparatus to which the impact is given.

(V) Step of Removing Protrusion

Step (V) in the production method according to the present embodiment is a step of removing the protrusion that exists on the surface of the particle of the calcined product by an air stream.

The protrusion exists on the surface of the particle of the calcined product subjected to the calcining step. In step (V), the protrusion is removed, and the amount of the protrusion that the calcined product has is preferably not more than 2% by mass based on the total mass of the calcined product. As the method for removing the protrusion, several methods can be thought. Among these, preferred is a method in which the protrusion is removed by contacting calcined products under a gas flow. Examples of the method include a method of flowing a gas in a hopper or the like in which the calcined product is stored, and a method of placing the calcined product in a fluidized bed reactor and flowing a gas therein. The method using a fluidized bed reactor is preferred because any special apparatus for removing the protrusion is unnecessary, but is not an apparatus originally intentionally designed to contact the calcined products (catalysts). Probably for this reason, the protrusion may not be sufficiently removed according to the condition such as the amount of the calcined product to be fed, the time to flow the calcined product, and the amount of the gas unless some measures are taken, for example, a small amount of the calcined product is fed and it takes some time to flow the calcined product. According to examination by the present inventors, the air stream at a sufficient flow rate can be contacted with the calcined product having the protrusion to efficiently remove the protrusion. If a proper flow rate is provided in an apparatus having a structure in which the air stream is contacted with the calcined product, the protrusion can be efficiently removed even in a large scale.

For example, an apparatus can efficiently remove the protrusion in a large scale, the apparatus including a main body that accommodates the calcined product, a recover unit for recovering the calcined product provided in an upper portion of the main body, and a returning unit for returning the calcined product and connected to the recover unit. The returning unit is provided so that a lower end thereof is in contact with the air stream. Part of the calcined product contacting the air stream within the main body is recovered by the recover unit, and returned into the main body by the returning unit.

A gas is flowed through the apparatus filled with the calcined product such as a fluidized bed reactor. Thereby, the calcined products contact each other to remove the protrusion. The protrusion removed from the calcined product is much smaller than the calcined product, and discharged with the flowed gas to the outside of the fluidized bed reactor. Preferably, the calcined product is filled into the apparatus so that the density of the calcined product at this time is 300 to 1300 kg/m$^3$. The cross section area of the body of the apparatus to be used is preferably 0.1 to 100 m$^2$, and more preferably 0.2 to 85 m$^2$.

The gas to be flowed is preferably an inert gas such as nitrogen and the air. The linear velocity (linear velocity) of the gas to be flowed through the body of the apparatus filled with the calcined product such as a hopper and a fluidized bed reactor is preferably 0.03 m/s to 5 m/s and more preferably 0.05 to 1 m/s. The time to flow the gas is preferably 1 to 168 hours. Specifically, the apparatus for removing a protrusion according to the present embodiment includes a main body, wherein the calcined product accommodated in the main body is contacted with the air stream, or the particles flowed by the air stream contact with each other to remove the protrusion on the surface of the calcined product from the calcined product. Preferably, the length of the air stream in the direction of the air stream flowing is not less than 55 mm, and the average flow rate of the air stream is not less than 80 m/s and not more than 500 m/s in terms of the linear velocity at 15° C. and 1 atmospheric pressure.

In the case where the catalyst used for the fluidized bed reaction has the protrusion, or the protrusion removed from the calcined product and the catalyst coexist, the fluidity of the catalyst is likely to be reduced. Reduction in the fluidity of the catalyst causes the catalyst to be localized within the reactor. As a result, heat removing efficiency is reduced. The heat may be accumulated to cause an abnormal reaction, or the decomposition reaction of the target product may progress in some reactions. Moreover, in the case where part of the protrusion is removed by contacting the calcined products within the apparatus for removing the protrusion such as a fluidized bed reactor, and discharged to the outside of the system from the inside of the apparatus, it is thought that the protrusion is mixed in the subsequent step to increase the load in the step. Accordingly, preferably, the calcined product and the protrusion does not coexist within the apparatus.

FIG. 1 is a drawing schematically showing an example of a suitable apparatus for removing a protrusion from a calcined product in a large scale. The apparatus shown in FIG. 1 includes a main body 1, a gas inlet pipe 2 penetrating the side surface of the main body 1, and an outlet pipe 3 provided on an upper surface of the main body 1 and connected to a cyclone 4.

The main body 1 has an approximately cylindrical shape, and the lower portion thereof has an inverted conical shape. The main body 1 accommodates the calcined product. From the viewpoint of efficiently removing the protrusion, the calcined product to be accommodated is preferably placed into the main body 1 until a gas inlet located in a highest position in the vertical direction of the gas inlet pipe 2 within the main body 1 is covered with the calcined product in the state where the calcined product stays. A large amount of the calcined product may be accommodated in the main body 1. In this case, an ability to separate of a separating apparatus such as a cyclone needs to be considered.

Figure 2:
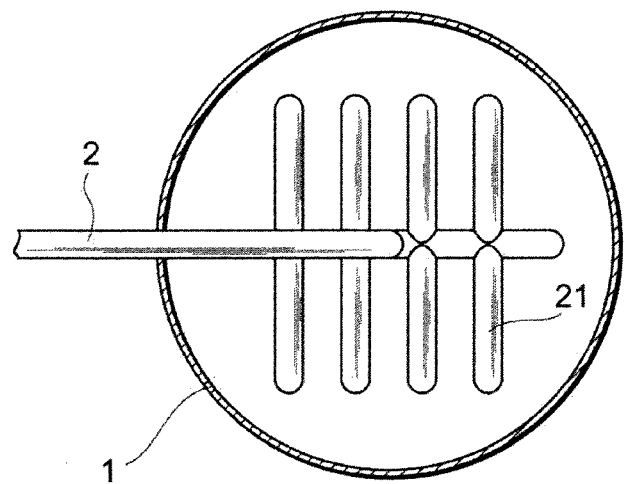
FIG. 2 is a diagram showing the X-X cross-section of the protrusion removing apparatus in FIG. 1.
Figure 3:
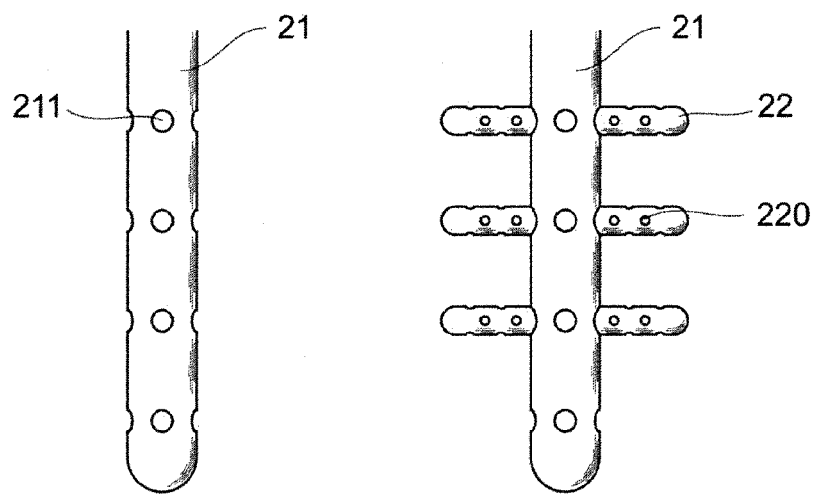
FIG. 3 is a diagram showing one example of branch pipes in a protrusion removing apparatus according to the present embodiment.

The gas inlet pipe 2 is introduced horizontally at a height of approximately a half of that of the main body 1. As shown in FIG. 2, the gas inlet pipe 2 is branched in the vicinity of the center of the main body 1, and further extended downwardly to form a branch pipe 21. In the example shown in FIG. 1, a plurality of branch pipes 21 of the gas inlet pipe 2 is provided downwardly in the vertical direction. The direction of the branch pipe 21 is not limited to this, and may be an upward direction, upward and downward directions, or a horizontal direction. As shown in the partially enlarged view in FIG. 1, each of the branch pipes 21 has a plurality of nozzles 210. The gas fed through the gas inlet pipe 2 is discharged from the respective nozzles 210. The structure of the branch pipe 21 is not limited to that having the nozzles 210. As shown in (A) of FIG. 3, the branch pipe 21 may have a plurality of openings 211. As shown in (B) of FIG. 3, a vertical subbranch 22 may be provided in the branch pipe 21, and the subbranch 22 may have a plurality of openings 220. A plurality of lower gas introducing nozzles 6 is fitted into the conical lower portion of the main body. In the example shown in FIG. 1, the gas introducing nozzle 6 has an L-shape. After the gas introducing nozzle 6 is vertically introduced into the main body, the gas introducing nozzle 6 is opened obliquely downwardly. For this reason, the calcined product placed within the main body is flowed by the gas introduced from the nozzle 6 toward the lower portion of the main body 1. The lower end of the main body 1 is opened, and connected to a second gas inlet pipe 7. Accordingly, the calcined product collected in the lower end by the gas fed from the gas introducing nozzle 6 is flowed within the main body 1 by a gas fed from the second gas inlet pipe 7. The shape of the nozzle front end 61 of the gas introducing nozzle is not limited to the L-shape, and may be an I-shape. Alternatively, no nozzle projected from the inner surface of the main body 1 may be provided, and the wall surface may be opened. In the case of the L-shaped nozzle, the nozzle may not be opened downwardly, and can be properly set according to the correlation with the gas fed from other second gas inlet pipe 7, or the shape of the main body 1. For example, the nozzle may be opened upwardly or horizontally.

One end of the outlet pipe 3 is attached to the central portion of the upper surface of the main body 1, and the other end thereof is connected to the cyclone 4. The cyclone 4 separates the calcined product from the protrusion removed from the calcined product by centrifugal force. The relatively large particles of the calcined product from which the protrusion is removed passes from the lower end of the cyclone through a return pipe 5 to be returned to the main body 1. On the other hand, because the protrusion is light, the protrusion passes through a discharge line 8 opened on the upper surface of the cyclone, and is removed. Preferably, a filter (not shown) is provided downstream of the discharge line 8 to capture the discharged protrusion.

Figure 4:
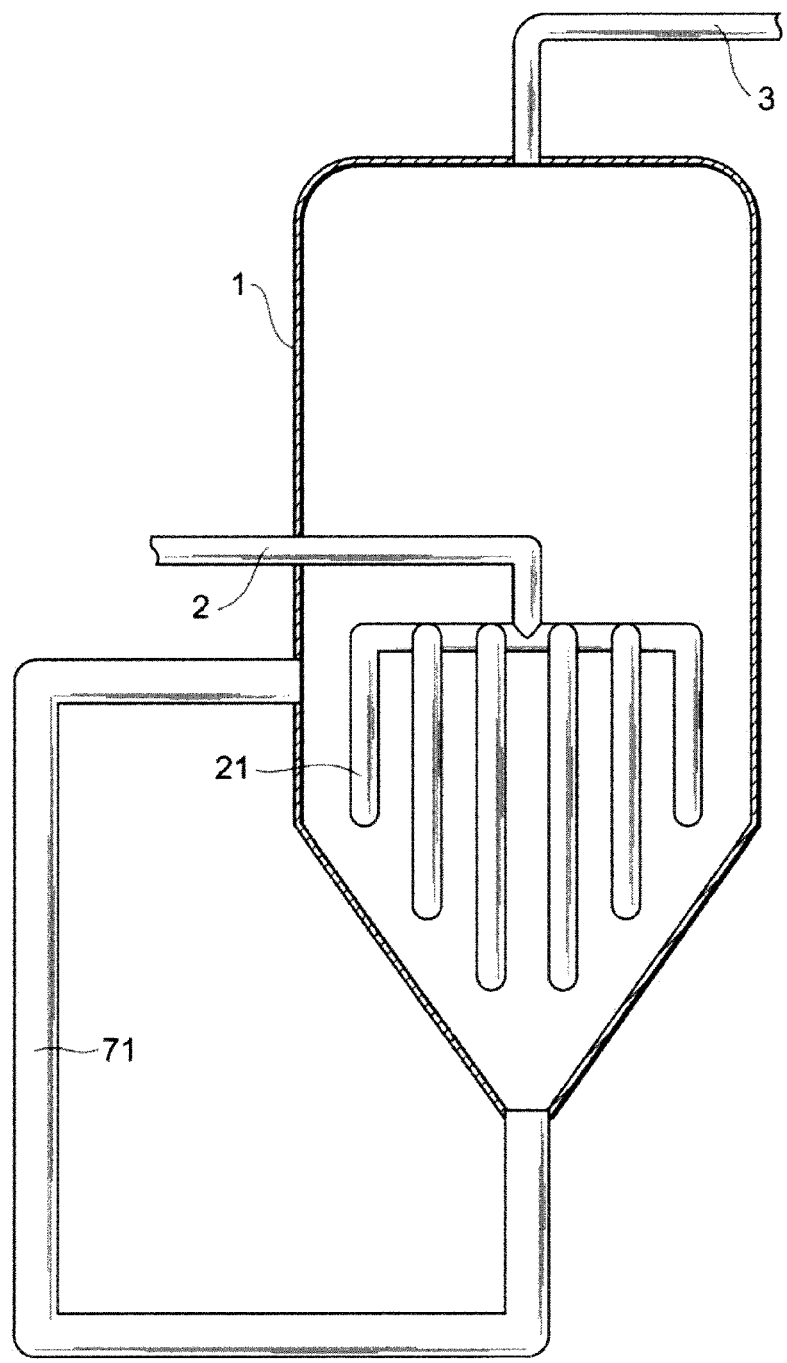
FIG. 4 is a diagram schematically showing one example of a protrusion removing apparatus according to the present embodiment.

The apparatus shown in FIG. 4 has the same configuration as that shown in the example of FIG. 1 except that a calcined product circulation line 71 is provided in the lower end of the main body 1. The other end of the circulation line 71 is opened in the side surface of the main body 1. Accordingly, a pneumer or the like is provided in the line to convey the calcined product flowed into the circulation line 71 by gas and return the calcined product into the main body 1.

Figure 5:
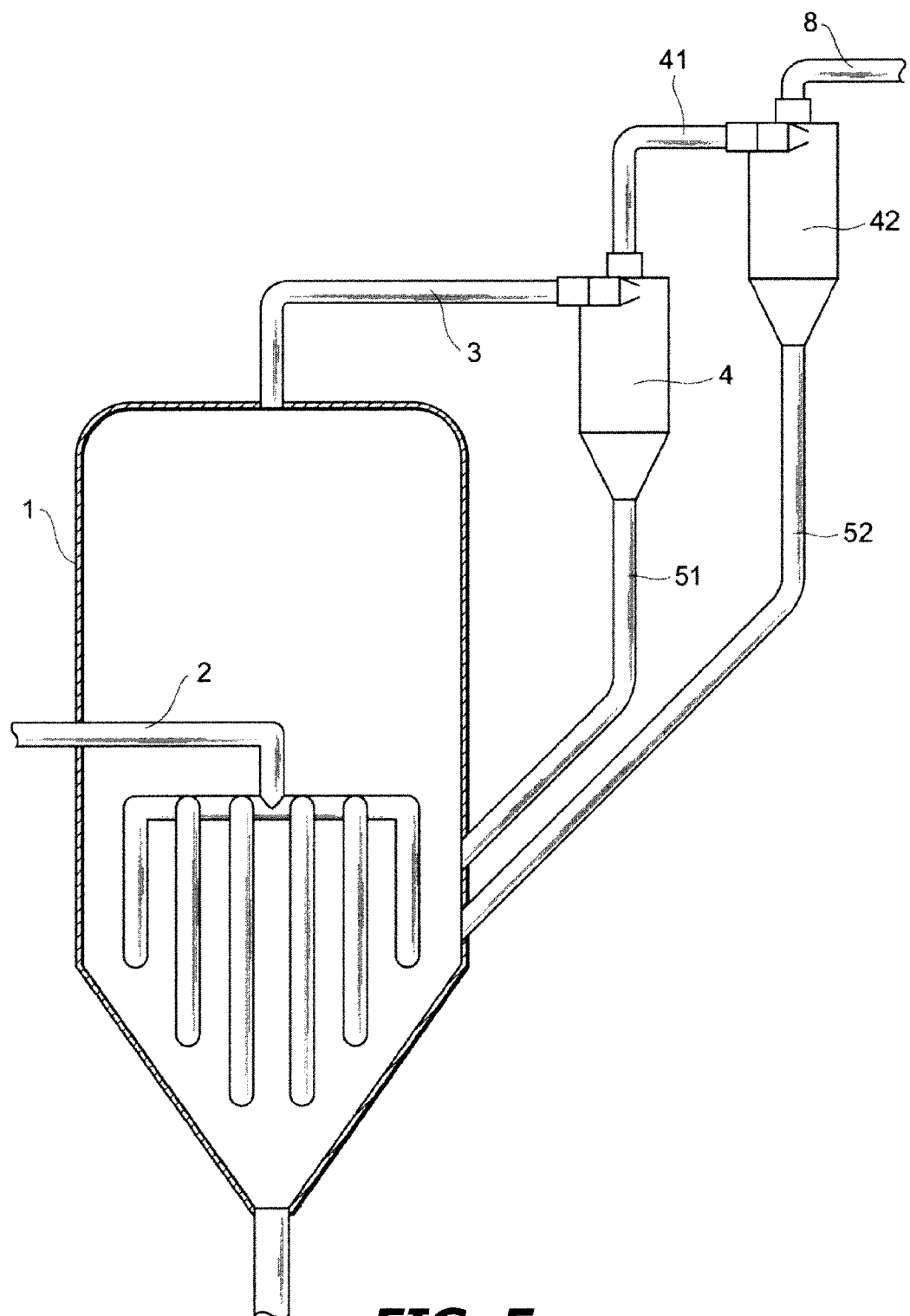
FIG. 5 is a diagram schematically showing one example of a protrusion removing apparatus according to the present embodiment.

The apparatus shown in FIG. 5 has the same configuration as that shown in the example of FIG. 1 except that a second cyclone 42 is connected to the outlet pipe 41 of the first cyclone 4. A return pipe 51 provided in lower end of the first cyclone 4 and a return pipe 52 provided in the lower end of the second cyclone 42 are connected to the side surface of the main body 1, and the recovered calcined product is returned to the main body 1.

Figure 6:
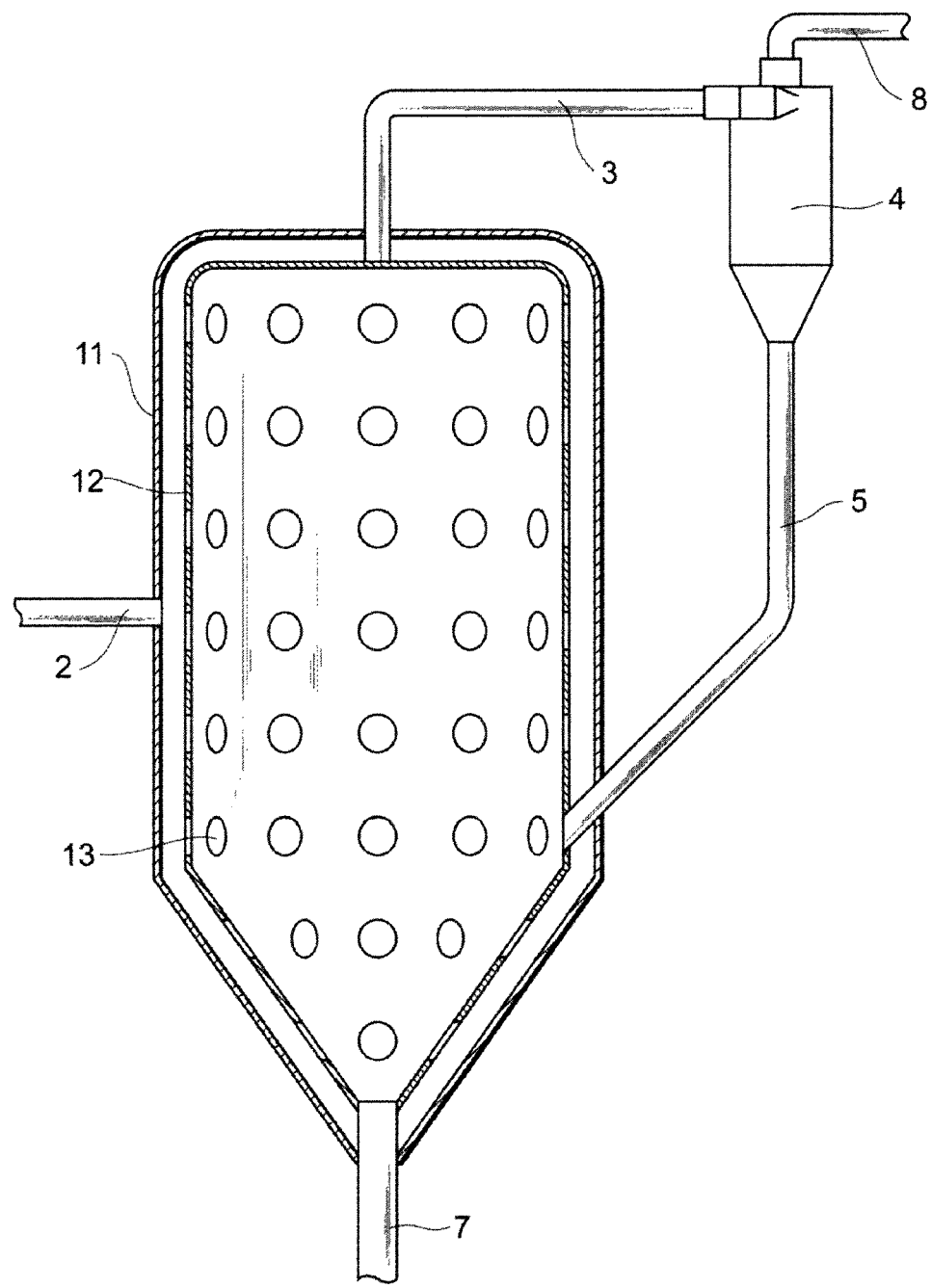
FIG. 6 is a diagram schematically showing one example of a protrusion removing apparatus according to the present embodiment.

The apparatus shown in FIG. 6 including a main body 1 having a double-layer structure including an outer tube 11 and an inner tube 12, an a gas is introduced between the outer tube 11 and the inner tube 12 from a gas inlet pipe 2. Except that, the apparatus shown in FIG. 6 has approximately the same configuration as that in FIG. 1, and only differences will be described below. The inner tube 12 has a plurality of openings 13, and the gas fed between the outer tube 11 and the inner tube 12 is ejected into the main body 1 from the openings 13. The inner tube 12 is opened to the outlet pipe 3 and the return pipe 5, while the outer tube 11 is not connected to the outlet pipe 3 and the return pipe 5. Accordingly, the calcined product does not enter the space between the outer tube 11 and the inner tube 12, and passes through the outlet pipe 3 to enter the cyclone 4, and is returned from the return pipe 5 to the main body 1. The second gas inlet pipe 7 is opened only to the inner tube 12. Thereby, a proper amount of a gas can be fed from the gas inlet pipe 7 so as to prevent stagnation of the calcined product in the bottom of the main body 1.

In the examples shown in FIG. 6, the gas inlet pipe 2 having the plurality of branch pipes 21 is not provided. In the case where the apparatus includes the main body 1 having a double-layer structure, the gas inlet pipe 2 having the branch pipes 21 may also be provided as shown in FIG. 1.

Figure 7:
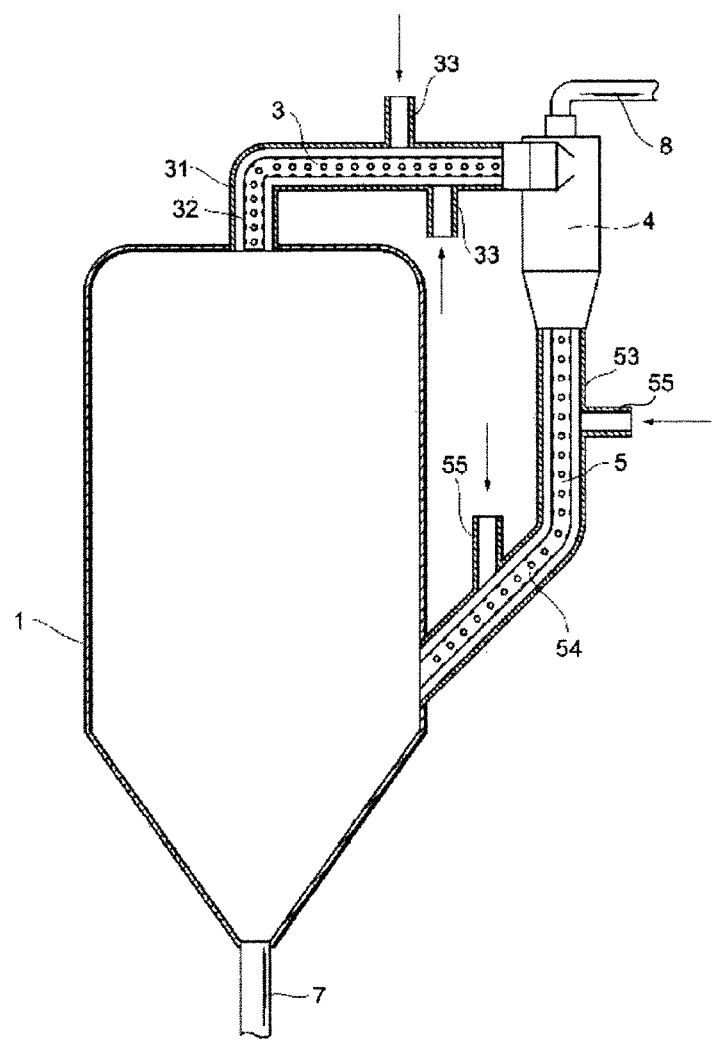
FIG. 7 is a diagram schematically showing one example of a protrusion removing apparatus according to the present embodiment.

The apparatus shown in FIG. 7 includes an outlet pipe 3 and a return pipe 5 each having a double-layer structure. Except that, the apparatus shown in FIG. 7 has approximately the same configuration as that in FIG. 1, and only differences will be described below. The outlet pipe 3 includes an outer pipe 31 and an inner pipe 32, and a gas is fed between these pipes from a nozzle 33. The return pipe 5 includes an outer pipe 53 and an inner pipe 54, and a gas is fed between these pipes from a nozzle 55. The apparatus shown in FIG. 7 may be used in combination with the apparatus shown in FIG. 6.

Preferably, the number of air stream flow ports per unit calcined product is larger from the viewpoint of increasing contact efficiency between the gas and the protrusion. The air stream flow port may be provided by directly making a hole in the wall surface of the main body for accommodating the calcined product to contact the calcined product with the air stream, or the air stream flow port may be provided in the main body via a line or a pipe by making a hole in the line or the pipe. However, in the case where the air streams contact each other, the calcined products may contact each other, and the calcined product may be cracked or chipped. For this, it is preferably designed so that the air streams do not cross. From the viewpoint of preventing cracking of the calcined product and wear of the line and the main body, preferably, the air stream does not directly contact the walls of the pipe and the main body.

Here, the air stream flow port indicates a hole through which the air stream enters the main body, wherein the length of the air stream in the direction of the air stream flowing is not less than 55 mm, and the average flow rate of the air stream is not less than 80.0 m/s and not more than 500 m/s in terms of a linear velocity at 15° C. and 1 atmospheric pressure. For example, the air stream flow port refers to holes represented by reference numeral 210 in FIG. 1, reference numerals 211 and 220 in FIG. 3, reference numeral 13 in FIG. 6, and reference numerals 32 and 54 in FIG. 7.

As the size of the air stream flow port, the diameter is preferably approximately 0.04 mm to 20 cm, and more preferably approximately 0.04 mm to 5 cm. The flow port may have any shape. Moreover, the diameter of the hole for the air stream may not be uniform. Further, the number of the air stream flow port is preferably larger, but it is thought that the calcined products contact each other to be cracked in the case where the holes are provided in a distance at which the air streams contact each other, as described above. Accordingly, desirably, considering the air stream size, air stream length, air stream volume, and the like calculated by the equations according to Literature (1) by Horio et al. and Literature (2) by YATES et al. below, an interval between the flow ports is provided to prevent the calcined products from contacting each other. From the viewpoint of the contact efficiency and fluidity of the catalyst, the air stream length at this time in the direction of the air stream flowing is desirably not less than 55 mm as long as the air stream does not contact the apparatus such as the wall of the main body and the pipe. The air stream length can be calculated using the equation of YATES et al., and the air stream size can be calculated using the equation of Horio et al.

The air stream length is represented by the equation:

$$hj/dor = 21.2 \cdot (uor^2/(g \cdot dp))^{0.37} \cdot (dor \cdot uor \cdot \rho g/\mu)^{0.05} \times (\rho g/\rho p)^{0.68} \cdot (dp/dor)^{0.24} \cdot dor,$$

wherein hj: air stream length [m], dor: orifice diameter [m], dp: particle size of the catalyst [m], uor: flow rate in the orifice [m/s], μ: viscosity of a gas [kg·m/sec], ρg: density of the gas [kg/m$^3$], ρp: density of catalyst particles [kg/m$^3$], g: gravitational acceleration [m/s$^2$].

On the other hand, the air stream size is represented by the equation:

$$(dj/dor) = 1.56 \cdot (fj \cdot Frj)/(k^{0.5} \cdot \tan \phi r))^{0.3} \cdot (dor/lor)^{0.2},$$

wherein dj: air stream size [m], fj: 0.02 (constant), $Frj = \rho g \cdot uor^2/((1-\epsilon mf) \cdot \rho p \cdot dp \cdot g)$, $k = (1-\sin \phi r)/(1+\sin \phi r)$, φr: angle of repose of the catalyst (here, approximated to 30°), lor: pitch [m].

(1) Horio, M., T. Yamada, and I. Muchi: Preprints of the 14th Fall Meeting of Soc. of Chem. Engrs., Japan, p. 760 (1980)
(2) Yates, J. G., P.N. Rowe and D. J. Cheesman: AIChE J., 30, 890 (1984).

The flow rate of the air stream is calculated from the area of the air stream flow port and the flow rate of the gas. In order to efficiently remove the protrusion from the surface of the calcined product, the average flow rate of the air streams ejected from the respective flow ports is not less than 80 m/s and not more than 500 m/s, and preferably not less than 200 m/s and not more than 341 m/s in terms of the linear velocity at 15° C. and 1 atmospheric pressure.

Here, a flow rate of ejection Y (m$^3$/h) and a flow rate of the air stream u (m/s) can be determined by the equation below, wherein the internal pressure of the line of the nozzle is a (kg/cm²G), the pressure of the nozzle is b (kg/cm²G), the temperature of the gas at that time is k (° C.), the pressure is p (kPa), and the area of the gas flow port is S (m²). The determined linear velocity can be averaged to determine the average flow rate of the air stream.

$$Y = 0.77 \times \sqrt{\frac{2 \times (a-b) \times 98067}{1.29 \times \frac{273.15}{(273.15+k)} \times \frac{(1.033+p)}{1.033}}} \times S \times 3600 \quad \text{[Expression 3]}$$

$$u = Y \times \frac{(1.033+a)}{(1.033+b)} \div S \div 3600 \quad \text{[Expression 4]}$$

The time for which the gas is contacted with the calcined product at the linear velocity above is preferably not less than 10 hours and not more than 100 hours. At a contact time less than 10 hours, the protrusion is likely to remain on the surface of the calcined product. At a contact time more than 100 hours, the surface of the calcined product is likely to be scraped to reduce the production efficiency of the catalyst. The contact time between the gas and the calcined product is preferably not less than 15 hours and not more than 60 hours. In order to enhance the circulation of the calcined product, and more efficiently remove the protrusion, a mechanism may be provided, for example, in which the calcined product is conveyed and circulated by a pneumer or the like to be contacted with the air stream. Alternatively, a propeller-like rotating body or a rotary bar-like object may be introduced within the main body of the apparatus, and rotated to stir the calcined product. Thereby, the contact efficiency between the calcined product and the air stream may be increased.

In the step of removing the protrusion according to the present embodiment, a combination of method is preferred, in which a high-speed gas (air stream) is flowed, and the air stream is contacted with the calcined product to flow the calcined product; at the same time, the protrusion on the surface of the calcined product is removed by air stream shear, and simultaneously, removed by mutual contact of the moving particles of the calcined product. At this time, any kind of the gas can be used. Preferable is dry air or an inert gas such as nitrogen.

Here, the present inventors thought that the value obtained by multiplying the air stream volume (V) by the number of the air stream flow ports (K) reflects the total volume of the air stream that can give a velocity to the calcined product, and assumed that the value obtained by multiplying this value by the square of the flow rate of the air stream (u) is equivalent to the total energy used to remove the protrusion. Then, while the respective variables were independently changed, the amount of the remaining protrusion in the calcined product having the amount of the calcined product M was measured over time. The correlation between the value obtained by dividing $u^2 \times V \times K$ by the amount of the calcined product (M) and the time needed to remove a sufficient amount of the protrusion from the surface of the calcined product was examined. As a result, $u^2 \times V \times K/M$ is approximately inversely proportional to the time needed to the treatment. Accordingly, it is suggested that $u^2 \times V \times K/M$ is appropriate as an index of energy (hereinafter, $u^2 \times V \times K/M$ is also referred to as an "energy-converted value" in some cases).

In the case where the catalyst is produced in an industrial scale, preferably, the time needed for each of the steps falls within a constant range in consideration of easiness of work. As for the step of removing the protrusion, if the time for the treatment is set so that the step is completed, for example, within one day, the operation is easier. As described above, the energy-converted value is approximately inversely proportional to the time needed for the removing treatment. Accordingly, if the energy-converted value is increased to some extent, the time needed for the removing treatment approximately inversely proportional to the energy-converted value can fall within a preferred time or less. From the viewpoint of controlling the time needed for the step of removing the protrusion to one day or less, the present inventors examined a preferred energy-converted value experimentally. It was found out that $u^2$, V, K, and M are preferably set so that the energy-converted value $u^2 \times V \times K/M$ (m⁵/s²/kg) represented using the flow rate of the air stream u (m/s), the volume (air stream volume) V (m³) formed by the air stream that passes through the air stream flow port, the number of the air stream flow ports K, and the mass M (kg) of the calcined product accommodated within the system satisfies:

$$14 < u^2 \times V \times K/M$$

On the other hand, from the viewpoint of preventing crack of the calcined product accompanied by contacting the calcined products and/or the calcined product with the wall surface of the system, it was found out that the respective numeric values are preferably set so that the energy-converted value satisfies:

$$u^2 \times V \times K/M < 100$$

Namely, it was found out that if the equation (X):

$$14 < u^2 \times V \times K/M < 100 \quad\quad\quad (X)$$

is satisfied, the treatment time in the removing step can fall within a constant range, and the breakage of the calcined product can be prevented; therefore, the protrusion can be efficiently removed from the surface of the calcined product. A suitable value of the energy-converted value depends on the factor of a removing apparatus, and changes depending on the shape and size of the apparatus, the direction of the nozzle, and contact with the wall. In the case of an apparatus in a scale used industrially, $20 < u^2 \times V \times K/M < 90$ is more preferable, and $30 < u^2 \times V \times K/M < 80$ is still more preferable.

The protrusion removed from the calcined product by the apparatus for removing the protrusion is much smaller than the spherical catalyst, and discharged with the flowed gas. Accordingly, the protrusion can be captured by a filter or the like. At the same time, however, fine (but larger than the protrusion) particles of the catalyst may be captured by the filter. Accordingly, a separating apparatus such as a cyclone is preferably used to increase separation efficiency. A plurality of the separating apparatuses such as a cyclone may be provided, and different separating apparatuses may be used in combination. Considering the case where a mixture of the catalyst having a fine particle size and the protrusion or the like is returned from the cyclone into the main body, for example, a three-way valve or the like may be provided under the cyclone, and a mechanism to individually recover the mixture in the outside of the system may be provided. The separated catalyst component is again conveyed to the inside of the main body. At this time, preferably, the catalyst component is returned to the position in which the catalyst contacts the air stream again. For example, in the case where the entire flow of the gas finally directs upward, it is thought that the catalyst moves upward along with the flow of the gas.

For this reason, preferably, a returning port for the separated catalyst is provided below the air stream port. In the case where the protrusion has a large angle of repose or the protrusion has viscosity, the protrusion may adhere to the wall surface within the main body, and adhere to the line to clog the line. For this reason, preferably, a knocker, a purge air, or the like is properly introduced into the system. Further, in order to remove the protrusion adhering to the line, a mechanism to wash using a liquid such as water and alcohol may be provided.

In the case where the protrusion is removed in a gram scale, the following apparatus can be used. Namely, a vertical tube including a plate having one or more holes formed in the bottom and a paper filter on the top can be used. The calcined product is placed in the vertical tube, and the air is flowed from under the vertical tube. Thereby, the air streams flow through the respective holes to promote contact of the calcined products and remove the protrusion.

In the production method according to the present embodiment, after the protrusion is removed, the complex oxide catalyst to be obtained contains the complex oxide having the composition represented by the formula (1):

$$Mo_1V_aSb_bNb_cW_dZ_eO_n \quad (1)$$

(wherein a component Z represents one or more elements selected from La, Ce, Pr, Yb, Y, Sc, Sr, and Ba; a, b, c, d, e, and n each represent an atomic ratio of an element to one Mo atom; $0.1 \leq a \leq 0.4$, $0.1 \leq b \leq 0.4$, $0.01 \leq c \leq 0.3$, $0 \leq d \leq 0.2$, and $0 \leq e \leq 0.1$; an atomic ratio a/b is $0.85 \leq a/b < 1.0$, an atomic ratio a/c is $1.4 < a/c < 2.3$).

In the production method according to the present embodiment, depending on the composition of the raw material-formulated solution at the time of preparation, usually, by removal of the protrusion, Mo, V, and Sb are reduced, and the atomic ratio a/b satisfies $0.85 \leq a/b < 1.0$, and the atomic ratio a/c satisfies $1.4 < a/c < 2.3$. If the atomic ratio a/b satisfies $0.85 \leq a/b < 1.0$, the yield is not reduced much by burning of propane derived from an excessive amount of V, and other crystal phase derived from an excessive amount of Sb is not grown much. Preferably, $0.88 \leq a/b < 1.0$, and more preferably, $0.90 \leq a/b < 1.0$. Moreover, it is thought that if the atomic ratio a/c satisfies $1.4 < a/c < 2.3$, growth of a crystalline reaction field for proper ammoxidation is promoted. If the amount of Nb is small, the crystalline ammoxidation reaction field is reduced. If the amount of Nb is excessively large, growth of a crystal phase other than the reaction field may be promoted. Preferably, $1.5 < a/c < 2.3$, and more preferably $1.6 < a/c < 2.3$.

The crystallite size of the catalyst is preferably 20 to 250 nm. At a crystallite size less than 20 nm, because crystal particles are small, the active site in the catalyst is also reduced. Moreover, because it is expected that even those that can be intrinsically an active species become other crystal system or amorphous, a side reaction is likely to be caused. At a crystallite size of the catalyst more than 250 nm, one plane of the active species of the catalyst is an active species of the catalyst, and the other plane thereof promotes the side reaction. For this reason, an excessively large catalyst is likely to promote the side reaction. From the same viewpoint, the crystallite size of the catalyst is more preferably 40 to 150 nm.

Usually, the size of the crystal can be measured using X ray diffraction. Herein, the crystallite size of the catalyst (L) is a value determined using a RINT2500 VHF (trade name) made by Rigaku Corporation according to the Scherer equation below.

$$L = K\lambda/(\beta \cos\theta)$$

Here, K is a constant of 0.9. $\lambda$ is a wavelength of the X-ray and 1.5418 Å. $\beta$ is a half width at the angle (unit: radian), and a value obtained by subtracting a half width B by a perfect and well-grown crystal (0.1 is used in the apparatus) from an actual half width b. $\theta$ and $\beta$ are input in radian. Growth of the crystal particles is greatly related with the calcining temperature and the composition of the catalyst. If the composition is the same, the crystallite size of the active species of the catalyst can be increased by increasing the calcining temperature. Moreover, by slowly reducing the temperature falling rate when the temperature is lowered from the main-calcining temperature, the crystallite size is larger. On the other hand, if the temperature is reduced rapidly, the crystallite size is smaller. Further, by the oxidation/reduction condition during calcination, and the composition at the time of preparation of the raw material, for example, increase of the content of the element such as Nb, the crystallite size is smaller. Thus, by adjusting a variety of conditions, the size of the crystallite can be controlled.

The complex oxide catalyst according to the present embodiment contains the complex oxide having the composition represented by the formula (I) at a stage before the complex oxide catalyst is fed to the vapor-phase catalytic oxidation reaction or vapor-phase catalytic ammoxidation reaction of propane or isobutane. After the catalytic reaction is started, the metal composition ratio is changed by sublimation of the metal element such as Mo or the catalyst newly added. In order to show a result of a preferred reaction at an initial stage and a continuous reaction, however, important is to have the composition represented by the formula (1) at a stage before the reaction is started. Namely, because the optimized composition of the complex oxide before the start of the reaction is the composition represented by the formula (1), the complex oxide may have the composition at the time of the start of the reaction even if the composition is changed to a different one later.

[Vapor-phase Catalytic Oxidation Reaction and Vapor-phase Catalytic Ammoxidation Reaction]

The vapor-phase catalytic oxidation reaction according to the present embodiment is a method for producing an unsaturated acid corresponding to propane or isobutane by a vapor-phase catalytic oxidation reaction of propane or isobutane, wherein the complex oxide catalyst is used.

Moreover, the vapor-phase catalytic ammoxidation reaction according to the present embodiment is a method for producing an unsaturated nitrile corresponding to propane or isobutane by a vapor-phase catalytic ammoxidation reaction of propane or isobutane, wherein the complex oxide catalyst is used.

The feed raw materials for propane, isobutane, and ammonia do not always need to have high purity, and a gas of industrial grade can be used. As a feed oxygen source, air, pure oxygen, or air enriched with pure oxygen can be used. Further, as a diluted gas, helium, neon, argon, carbon dioxide gas, steam, nitrogen, and the like may be fed.

The vapor-phase catalytic oxidation reaction of propane or isobutane can be performed on the following condition.

The molar ratio of oxygen to be fed in the reaction to propane or isobutane is preferably 0.1 to 6, and more preferably 0.5 to 4. The reaction temperature is preferably 300 to 500° C., and more preferably 350 to 500° C. The reaction pressure is preferably $5 \times 10^4$ to $5 \times 10^5$ Pa, and more preferably $1 \times 10^5$ to $3 \times 10^5$ Pa. The contact time is preferably 0.1 to 10 (sec·g/cc), and more preferably 0.5 to 5 (sec·g/cc).

In the present embodiment, the contact time is defined by the equation below:

Contact time (sec·g/cc)=$(W/F) \times 273/(273+T)$

Here, W, F, and T are defined as follows:
W=amount of the catalyst to be filled (g)
F=flow rate of the raw material mixed gas (Ncc/sec) in a standard state (0° C., 1.013×10⁵ Pa)
T=reaction temperature (° C.)

The vapor-phase catalytic ammoxidation reaction of propane or isobutane can be performed on the following condition.

The molar ratio of oxygen to be fed in the reaction to propane or isobutane is preferably 0.1 to 6, and more preferably 0.5 to 4. The molar ratio of ammonia to be fed in the reaction to propane or isobutane is preferably 0.3 to 1.5, and more preferably 0.7 to 1.2. The reaction temperature is preferably 350 to 500° C., and more preferably 380 to 470° C. The reaction pressure is preferably 5×10⁴ to 5×10⁵ Pa, and more preferably 1×10⁵ to 3×10⁵ Pa. The contact time is preferably 0.1 to 10 (sec-g/cc), and more preferably 0.5 to 5 (sec·g/cc).

As the reaction method for the vapor-phase oxidation reaction and the vapor-phase ammoxidation reaction, the conventional method such as a fixed bed, a fluidized bed, and a moving bed can be used. Preferred is a fluidized bed reactor in which the reaction heat is easily removed. The vapor-phase catalytic ammoxidation reaction may be a single current system or a recycle system.

EXAMPLES

Hereinafter, the present embodiment will be further described in detail with reference to examples and comparative examples. However, the present embodiment is not limited to the examples.

In the examples and the comparative examples, a propane or isobutane conversion, and yield of acrylonitrile or methacrylonitrile respectively follow the following definitions.

Propane conversion (%)=(Number of moles of reacted propane)/(Number of moles of supplied propane)×100

Yield of Acrylonitrile (AN) (%)=(Number of moles of produced acrylonitrile)/(Number of moles of supplied propane)×100

(Measurement Method of Reduction Index of Pre-stage Calcined Product)

About 200 mg of the pre-stage calcined product was precisely weighed in a beaker. A $KMnO_4$ aqueous solution whose concentration was known was added in an excessive amount thereto. 150 mL of pure water at 70° C. and 2 mL of a 1:1 sulfuric acid (that is, a sulfuric acid aqueous solution obtained by mixing a concentrated sulfuric acid and water in a volume ratio of 1/1; hereinafter, the same) were further added. Then, the beaker was covered with a watch glass, and the solution was stirred in a hot water bath at 70° C.±2° C. for one hour to oxidize the sample. At this time, since $KMnO_4$ was excessively present and unreacted $KMnO_4$ was present in the solution, it was confirmed that the color of the solution was purple. After the completion of the oxidization, the solution was filtrated with a filter paper, and the whole amount of the filtrate was recovered. A sodium oxalate ($Na_2C_2O_4$) aqueous solution whose concentration was known was added in an excessive amount with respect to $KMnO_4$ present in the filtrate, and heated and stirred so that the solution temperature became 70° C. It was confirmed that the solution became colorless and transparent, and 2 mL of a 1:1 sulfuric acid was then added. The solution was stirred continuously with the solution temperature being kept at 70° C.±2° C., and was titrated with a $KMnO_4$ aqueous solution whose concentration was known. At this time, a point at which the solution color assumed a faint light pink color by $KMnO_4$ and lasted for about 30 seconds was defined as an end-point.

The $KMnO_4$ amount consumed for the oxidation of the sample was determined from the total $KMnO_4$ amount and the total $Na_2C_2O_4$ amount. ($n_0-n$) was calculated from the value, and the reduction index was determined based on the ($n_0-n$).

(Measurement Method of Specific Surface Area of Calcined Product)

The specific surface area of a calcined product was determined by BET one-point method using Gemini 2360 (trade name) made by Micromeritics Instrument Corp.

(Preparation of Niobium Mixed-solution)

A niobium mixed-solution was prepared by a method as described below. To 10 kg of water, 1.530 kg of niobic acid containing 79.8% by mass of niobium in terms of $Nb_2O_5$ and 5.266 kg of oxalic acid dihydrate [$H_2C_2O_4 \cdot 2H_2O$] were added. A molar ratio of oxalic acid/niobium as feedstocks was 5.0 and a concentration of feedstock niobium was 0.50 (mol-Nb/kg-solution). The resultant solution was heated for two hours at 95° C. with stirring, thereby obtaining a mixed-solution in which niobium was dissolved. This mixed-solution was left standstill, cooled with ice, subjected to a suction filtration for removing a solid content, thereby obtaining a uniform niobium mixed-solution. The molar ratio of the oxalic acid/niobium of this niobium mixed-solution was 2.68 by the analysis described below.

10 g of this niobium mixed-solution was precisely weighed and put in a crucible, dried for a night at 95° C., and subjected to a heat treatment for one hour at 600° C., thereby obtaining 0.7895 g of $Nb_2O_5$. From this result, the niobium concentration was 0.594 (mol-Nb/kg-solution). 3 g of this niobium mixed-solution was precisely weighed and put in a glass beaker having a capacity of 300 ml, added with 200 ml of hot water having a temperature of about 80° C. and, then, added with 10 ml of a 1:1 sulfuric acid. The resultant mixed-solution was titrated by using a 1/4 N $KMnO_4$ solution with stirring while being kept at a temperature of 70° C. on a hot stirrer. A point at which a faint light pink color by $KMnO_4$ lasted for about 30 seconds or more was defined as an end-point. A concentration of oxalic acid was determined on the basis of the resultant titer in accordance with the following formula and, as a result, it was 1.592 (mol-oxalic acid/kg).

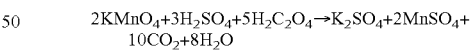

$$2KMnO_4+3H_2SO_4+5H_2C_2O_4 \rightarrow K_2SO_4+2MnSO_4+10CO_2+8H_2O$$

The obtained niobium mixed-solution ($B_0$) was used as a niobium raw-material solution in production of a composite oxide catalyst in Examples 1 to 14 to be described below.

Example 1

(Preparation of Dry Powder)

A dry powder ($D_1$) was produced as follows.

To 1.557 kg of water, 432.1 g of ammonium heptamolybdate [$(NH_4)_6Mo_7O_{24} \cdot 4H_2O$], 59.9 g of ammonium metavanadate [$NH_4VO_3$], 84.3 g of diantimony trioxide [$Sb_2O_3$], and further, 4.8 g of cerium nitrate [$Ce(NO_3)_3 \cdot 6H_2O$] were added and heated for 1 hour at 95° C. with stirring, thereby preparing an aqueous raw-material solution ($A_1$).

To 378.4 g of a niobium mixed-solution ($B_0$), 66.3 g of a hydrogen peroxide solution containing 30% by mass in terms of $H_2O_2$ was added and mixed for 10 minutes at room temperature with stirring, thereby preparing an aqueous raw-material solution ($B_1$).

After the obtained aqueous raw-material solution ($A_1$) was cooled to 70° C., 807.8 g of silica sol containing 34.0% by mass in terms of $SiO_2$ was added thereto and, further, 98.4 g of a hydrogen peroxide solution containing 30% by mass in terms of $H_2O_2$ was added thereto and then, the resultant mixture was continuously stirred for 30 minutes at 55° C. Next, the aqueous raw-material solution ($B_1$), 31.0 g of an aqueous solution of ammonium metatungstate (purity: 50%), and a dispersion liquid in which 211.5 g of silica powder was dispersed in 2.855 kg of water were sequentially added thereto, and then aged for 2.5 hours at 50° C. with stirring, thereby obtaining a slurry aqueous mixed solution ($C_1$) as a raw material-formulated solution.

The obtained aqueous mixed-solution ($C_1$) was supplied to a centrifugal spray dryer (heat source for drying is air. Hereinafter, the same.) and dried, thereby obtaining a microspherical dry powder ($D_1$). The temperatures at the inlet of the dryer was 210° C. and the temperature at the outlet thereof was 120° C.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.2% by mass, and the average particle size was 54 μm. The particle content and the average particle size were measured by LS230 (trade name) made by BECKMAN COULTER, Inc. (hereinafter, the same).

(Calcination of Dry Powder ($E_1$))

The obtained dry powder ($E_1$) was fed in a feed amount of 80 g/hr to a continuous-type cylindrical calcining tube made of SUS and having a diameter (inner diameter; hereinafter, the same) of 3 inches and a length of 89 cm in a rotary furnace. A nitrogen gas at 1.5 NL/min was made to flow in the calcining tube in each direction of the direction opposite to the feed direction of the dry powder (that is, counterflow; hereinafter, the same) and the same direction thereas (that is, concurrent flow; hereinafter, the same), and the total flow rate was made 3.0 NL/min. An air knocker was provided on either end of the calcining tube made of SUS, and the knocking frequency of the air knocker was set so as to make knocks of 10 times per minute. The pneumatic pressure of an air knocker inlet was set so that the vibration acceleration at the surface of the calcining tube made of SUS by the knocks became 50 m/sec². The vibration acceleration was measured using a vibrometer (MD-220 (trade name) made by Asahi Kasei Technosystem Co., Ltd.; hereinafter, the same). A pre-stage calcination was carried out by setting the temperature of the furnace so that the temperature was raised to 370° C. being the maximum calcination temperature over four hours and kept at 370° C. for one hour while the calcining tube was being rotated at a rate of 4 rpm. A small amount of the pre-stage calcined product recovered at a calcining tube outlet was sampled; and the sample was heated to 400° C. under a nitrogen atmosphere, and thereafter measured for the reduction index, which was 10.2%. The pre-stage calcined product recovered was fed in a feed amount of 60 g/hr to a continuous-type calcining tube made of SUS and having a diameter 3 inches and a length of 89 cm in a rotary furnace. A nitrogen gas at 1.1 NL/min was made to flow in the calcining tube in each direction of the direction opposite to the feed direction of the dry powder and the same direction thereas, and the total flow rate was made 2.2 NL/min. An air knocker was provided on either end of the calcining tube made of SUS, and the knocking frequency of the air knocker was set so as to make knocks of 10 times per minute. The pneumatic pressure of an air knocker inlet was set so that the vibration acceleration at the surface of the calcining tube made of SUS by the knocks became 50 m/sec². The vibration acceleration was measured using a vibrometer. A main calcination was carried out by setting the temperature of the furnace so that the temperature was raised to 680° C. over two hours, kept at 680° C. for two hours and descended to 300° C. over eight hours. The specific surface area of a calcined product ($F_1$) obtained from a calcining tube outlet was measured, and was 14.0 m²/g. The specific surface area of the calcined product was determined by BET one-point method using Gemini 2360 (trade name) made by Micromeritics Instrument Corp. (hereinafter, the same).

(Removal of Protrusions)

50 g of the calcined product ($F_1$) was charged in a vertical tube (inner diameter: 41.6 mm, length: 70 cm) in which a holed disc having three holes of 1/64 inch in diameter was provided on the bottom of the tube, and a paper filter was provided in the upper part thereof. Then, air was circulated at room temperature upward from down in the vertical tube through the holes, thereby promoting contact of the calcined product with each other. The length of the air flow in the air flow direction at this time was 56 mm, and the average line speed of the air flow was 332 m/sec. No protrusions were present in a composite oxide catalyst ($G_1$) obtained after 24 hours.

The compositional ratios of a/b and a/c of the composite oxide catalyst ($G_1$) were measured by fluorescent X-ray analysis (apparatus: RINT 1000 (trade name), made by Rigaku Corp.; Cr bulb, bulb voltage: 50 kV, bulb current: 50 mA; hereinafter, the same). The results acquired are shown in Table 1. The composition of the composite oxide catalyst ($G_1$) obtained at this time was $Mo_1V_{0.207}Sb_{0.219}Nb_{0.102}W_{0.030}Ce_{0.005}O_n$/51.0 wt %-$SiO_2$.

X-ray diffractometry of the composite oxide catalyst ($G_1$) was carried out using an X-ray diffractometer (RINT 2500 VHF (trade name), made by Rigaku Corp.; Cu bulb, bulb voltage: 40 kV, bulb current: 200 mA; hereinafter, the same). At this time, a peak of 2θ=8.9° was paid attention to, and the crystal grain diameter was measured from Scherrer equation, and was 52 nm.

(Ammoxidation Reaction of Propane)

Propane was subjected to a vapor-phase ammoxidation reaction by the following method using the composite oxide catalyst ($G_1$) obtained above. 35 g of the composite oxide catalyst was packed in a Vycor glass fluidized bed-type reaction tube having an inner diameter of 25 mm; and a mixed gas of propane:ammonia:oxygen:helium=1:1:3:18 in molar ratio was supplied at a contact time of 2.8 (sec·g/cc) at a reaction temperature of 440° C. under a reaction pressure of normal pressure. The propane conversion after the reaction was 89.2%, and the yield of acrylonitrile was 55.5%. The reaction was carried out continuously for 30 days using the catalyst, and the yield of acrylonitrile was 55.4%.

Example 2

(Preparation of Dry Powder)

A dry powder ($D_1$) was produced as follows.

To 2.202 kg of water, 611.5 g of ammonium heptamolybdate [$(NH_4)_6Mo_7O_{24}\cdot4H_2O$], 84.7 g of ammonium metavanadate [$NH_4VO_3$], 119.3 g of diantimony trioxide [$Sb_2O_3$], and further, 6.8 g of cerium nitrate [Ce (NO$_3$)$_3$.6H$_2$O] were added and heated for 1 hour at 95° C. with stirring, thereby preparing an aqueous raw-material solution (A$_1$).

To 535.5 g of a niobium mixed-solution (B$_0$), 93.8 g of a hydrogen peroxide solution containing 30% by mass in terms of H$_2$O$_2$ was added and mixed with stirring for 10 minutes at room temperature, thereby preparing an aqueous raw-material solution (B$_1$).

After the obtained aqueous raw-material solution (A$_1$) was cooled to 70° C., 429.7 g of silica sol containing 34.0% by mass in terms of SiO$_2$ was added thereto and, further, 98.4 g of a hydrogen peroxide solution containing 30% by mass in terms of H$_2$O$_2$ was added thereto and then, the resultant mixture was continuously stirred for 30 minutes at 55° C. Next, the aqueous raw-material solution (B$_1$), 42.8 g of an aqueous solution of ammonium metatungstate (purity: 50%), and a dispersion liquid in which 112.5 g of silica powder was dispersed in 1519 kg of water were sequentially added thereto, and then aged for 2.5 hours at 50° C. with stirring, thereby obtaining a slurry aqueous mixed-solution (C$_1$) as a raw material-formulated solution.

The obtained aqueous mixed-solution (C$_1$) was fed and dried in a centrifugal spray dryer, thereby obtaining a microspherical dry powder (D$_1$). The temperatures at the inlet the dryer was 210° C. and the temperature at the outlet thereof was 120° C.
(Classification Operation)

The obtained dry powder (D$_1$) was classified using a sieve having a sieve opening of 25 μm to obtain a dry powder (E$_1$) being a classified product. The content of particles of 25 μm or smaller of the obtained dry powder (E$_1$) was 0.3% by mass, and the average particle size was 52 μm.
(Calcination of Dry Powder (E$_1$))

The calcination was carried out under the same calcination condition as in Example 1. The reduction index of the pre-stage calcined product at this time was 10.3%, and the specific surface area of the calcined product after the main calcination was 12.5 m$^2$/g.
(Removal of Protrusions)

Protrusions were removed under the same condition as in Example 1, and the compositional ratios of a/b and a/c of the composite oxide catalyst (G$_1$) were measured by the fluorescent X-ray analysis. The results acquired are shown in Table 1. The composition of the composite oxide catalyst (G$_1$) obtained at this time was Mo$_1$V$_{0.207}$Sb$_{0.219}$Nb$_{0.102}$W$_{0.03}$Ce$_{0.005}$O$_n$/30.0 wt %-SiO$_2$.
(Ammoxidation Reaction of Propane)

The reaction was carried out under the same condition as in Example 1; and the propane conversion after the reaction was 87.2%, and the yield of acrylonitrile was 54.5%.

Example 3

(Preparation of Dry Powder)

A dry powder (D$_1$) was produced as follows.

To 1.027 kg of water, 285.4 g of ammonium heptamolybdate [(NH$_4$)$_6$Mo$_7$O$_{24}$.4H$_2$O], 39.5 g of ammonium metavanadate [NH$_4$VO$_3$], 55.7 g of diantimony trioxide [Sb$_2$O$_3$], and further, 3.2 g of cerium nitrate [Ce(NO$_3$)$_3$.6H$_2$O] were added and heated for one hour at 95° C. with stirring, thereby preparing an aqueous raw-material solution (A$_1$).

To 249.9 g of a niobium mixed-solution (B$_0$), 43.8 g of a hydrogen peroxide solution containing 30% by mass in terms of H$_2$O$_2$ was added and mixed with stirring for 10 minutes at room temperature, thereby preparing an aqueous raw-material solution (B$_1$).

After the obtained aqueous raw-material solution (A$_1$) was cooled to 70° C., 1117.2 g of silica sol containing 34.0% by mass in terms of SiO$_2$ was added thereto and, further, 98.4 g of a hydrogen peroxide solution containing 30% by mass in terms of H$_2$O$_2$ was added thereto and then, the resultant mixture was continuously stirred for 30 minutes at 55° C. Next, the aqueous raw-material solution (B$_1$), 20.4 g of an aqueous solution of ammonium metatungstate (purity: 50%), and a dispersion liquid in which 292.5 g of silica powder was dispersed in 3948 kg of water were sequentially added thereto, and then aged for 2.5 hours at 50° C. with stirring, thereby obtaining a slurry aqueous mixed-solution (C$_1$) as a raw material-formulated solution.

The obtained aqueous mixed-solution (C$_1$) was fed and dried in a centrifugal spray dryer, thereby obtaining a microspherical dry powder (D$_1$). The temperature at the inlet of the dryer was 210° C., and the temperature at the outlet thereof was 120° C.
(Classification Operation)

The obtained dry powder (D$_1$) was classified using a sieve having a sieve opening of 25 μm to obtain a dry powder (E$_1$) being a classified product. The content of particles of 25 μm or smaller of the obtained dry powder (E$_1$) was 0.3% by mass, and the average particle size was 56 μm.
(Calcination of Dry Powder (E$_1$))

The calcination was carried out under the same calcination condition as in Example 1. The reduction index of the pre-stage calcined product at this time was 10.5%, and the specific surface area of the calcined product after the main calcination was 17.0 m$^2$/g.
(Removal of Protrusions)

Protrusions were removed under the same condition as in Example 1, and the compositional ratios of a/b and a/c of the composite oxide catalyst (G$_1$) were measured by the fluorescent X-ray analysis. The results acquired are shown in Table 1. The composition of the composite oxide catalyst (G$_1$) obtained at this time was Mo$_1$V$_{0.207}$Sb$_{0.219}$Nb$_{0.102}$W$_{0.03}$Ce$_{0.005}$O$_n$/68.0 wt %-SiO$_2$.
(Ammoxidation Reaction of Propane)

The reaction was carried out under the same condition as in Example 1; and the propane conversion after the reaction was 88.8%, and the yield of acrylonitrile was 55.1%.

Example 4

(Preparation of Dry Powder)

A dry powder (D$_1$) was produced as follows.

To 1.806 kg of water, 432.1 g of ammonium heptamolybdate [(NH$_4$)$_6$Mo$_7$O$_{24}$.4H$_2$O], 69.4 g of ammonium metavanadate [NH$_4$VO$_3$], 90.1 g of diantimony trioxide [Sb$_2$O$_3$], and further, 4.8 g of cerium nitrate [Ce(NO$_3$)$_3$.6H$_2$O] were added and heated for one hour at 95° C. with stirring, thereby preparing an aqueous raw-material solution (A$_1$).

To 504.5 g of a niobium mixed-solution (B$_0$), 88.4 g of a hydrogen peroxide solution containing 30% by mass in terms of H$_2$O$_2$ was added and mixed with stirring for 10 minutes at room temperature, thereby preparing an aqueous raw-material solution (B$_1$).

After the obtained aqueous raw-material solution (A$_1$) was cooled to 70° C., 807.8 g of silica sol containing 34.0% by mass in terms of SiO$_2$ was added thereto and, further, 98.4 g of a hydrogen peroxide solution containing 30% by mass in terms of H$_2$O$_2$ was added thereto and then, the resultant mixture was continuously stirred for 30 minutes at 55° C. Next, the aqueous raw-material solution (B$_1$), 31.0 g of an aqueous solution of ammonium metatungstate (purity: 50%), and a dispersion liquid in which 211.5 g of silica powder was dispersed in 2.855 kg of water were sequentially added thereto, and then aged for 2.5 hours at 50° C. with stirring, thereby obtaining a slurry aqueous mixed-solution ($C_1$) as a raw material-formulated solution.

The obtained aqueous mixed-solution ($C_1$) was fed and dried in a centrifugal spray dryer, thereby obtaining a microspherical dry powder ($D_1$). The temperature at the inlet of the dryer was 210° C., and the temperature at the outlet thereof was 120° C.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.5% by mass, and the average particle size was 55 μm.

(Calcination of Dry Powder ($E_1$))

The calcination was carried out under the same calcination condition as in Example 1. The reduction index of the pre-stage calcined product at this time was 10.0%, and the specific surface area of the calcined product after the main calcination was 12.5 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.240}Sb_{0.250}Nb_{0.120}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 87.5%, and the yield of acrylonitrile was 55.2%.

Example 5

(Preparation of Dry Powder)

The preparation of a dry powder ($D_1$) was carried out by the same method as in Example 1.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.5% by mass, and the average particle size was 58 μm.

(Calcination of Dry Powder ($E_1$))

The calcination was carried out under the same calcination condition as in Example 1, except for altering the pre-stage calcination temperature to 360° C., and altering the total nitrogen flow rate in the pre-stage calcination to 7.5 NL/min. The reduction index of the pre-stage calcined product at this time was 10.0%, and the specific surface area of the calcined product after the main calcination was 12.0 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 88.8%, and the yield of acrylonitrile was 55.1%.

Example 6

(Preparation of Dry Powder)

The preparation of a dry powder ($D_1$) was carried out by the same method as in Example 1.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.7% by mass, and the average particle size was 54 μm.

(Calcination of Dry Powder ($E_1$))

The calcination was carried out under the same calcination condition as in Example 1, except for altering the total nitrogen flow rate in the pre-stage calcination to 2.3 NL/min (the counterflow and the concurrent flow were each 1.15 NL/min). The reduction index of the pre-stage calcined product at this time was 10.3%, and the specific surface area of the calcined product after the main calcination was 14.8 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 89.0%, and the yield of acrylonitrile was 55.1%.

Example 7

(Preparation of Dry Powder)

The preparation of a dry powder ($D_1$) was carried out by the same method as in Example 1.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.2% by mass, and the average particle size was 53 μm.

(Calcination of Dry Powder ($E_1$))

The calcination was carried out under the same calcination condition as in Example 1, except for altering the total nitrogen flow rate in the main calcination to 3.2 NL/min (the counterflow and the concurrent flow were each 1.6 NL/min). The reduction index of the pre-stage calcined product at this time was 10.3%, and the specific surface area of the calcined product after the main calcination was 13.6 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 88.6%, and the yield of acrylonitrile was 55.1%.

Example 8

(Preparation of Dry Powder)

The preparation of a dry powder ($D_1$) was carried out by the same method as in Example 1.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.3% by mass, and the average particle size was 52 μm.

(Calcination of Dry Powder ($E_1$))

The calcination was carried out under the same calcination condition as in Example 1, except for altering the total nitrogen flow rate in the main calcination to 1.0 NL/min (the counterflow and the concurrent flow were each 0.5 NL/min). The reduction index of the pre-stage calcined product at this time was 10.1%, and the specific surface area of the calcined product after the main calcination was 12.4 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 89.1%, and the yield of acrylonitrile was 55.1%.

Example 9

(Preparation of Dry Powder)

The preparation of a dry powder ($D_1$) was carried out by the same method as in Example 1.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.1% by mass, and the average particle size was 49 μm.

(Calcination of Dry Powder ($E_1$))

The calcination was carried out under the same calcination condition as in Example 1, except for altering the rotation frequency of the calcining tube in the pre-stage calcination to 1 rpm. The reduction index of the pre-stage calcined product at this time was 11.2%, and the specific surface area of the calcined product after the main calcination was 15.6 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 87.2%, and the yield of acrylonitrile was 54.0%.

Example 10

(Preparation of Dry Powder)

The preparation of a dry powder ($D_1$) was carried out by the same method as in Example 1.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.6% by mass, and the average particle size was 55 μm.

(Calcination of Dry Powder ($E_1$))

The calcination was carried out under the same calcination condition as in Example 1, except for altering the maximum calcination temperature in the pre-stage calcination to 330° C., the rotation frequency of the calcining tube to 12 rpm, and the total nitrogen flow rate in the pre-stage calcination to 6.0 NL/min (the counterflow and the concurrent flow were each 3.0 NL/min). The reduction index of the pre-stage calcined product at this time was 9.8%, and the specific surface area of the calcined product after the main calcination was 12.1 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 90.0%, and the yield of acrylonitrile was 54.2%.

Example 11

(Preparation of Dry Powder)

The preparation of a dry powder ($D_1$) was carried out by the same method as in Example 1.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.5% by mass, and the average particle size was 58 μm.

(Calcination of Dry Powder ($E_1$))

The calcination was carried out under the same calcination condition as in Example 1, except for altering the feed amount of the dry powder ($E_1$) in the pre-stage calcination to 72 g/hr. The reduction index of the pre-stage calcined product at this time was 10.5%, and the specific surface area of the calcined product after the main calcination was 14.3 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 87.9%, and the yield of acrylonitrile was 54.9%.

Example 12

(Preparation of Dry Powder)

The preparation of a dry powder ($D_1$) was carried out by the same method as in Example 1.

(Classification Operation)

The obtained dry powder ($D_1$) was classified using a sieve having a sieve opening of 25 μm to obtain a dry powder ($E_1$)

being a classified product. The content of particles of 25 μm or smaller of the obtained dry powder ($E_1$) was 0.4% by mass, and the average particle size was 60 μm.

(Calcination of Dry Powder ($E_1$))

The calcination was carried out under the same calcination condition as in Example 1, except for altering the feed amount of the dry powder ($E_1$) in the pre-stage calcination to 89 g/hr. The reduction index of the pre-stage calcined product at this time was 9.9%, and the specific surface area of the calcined product after the main calcination was 12.2 $m^2/g$.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 87.8%, and the yield of acrylonitrile was 54.6%.

Example 13

(Preparation of Dry Powder)

The preparation of a dry powder ($D_1$) was carried out by the same method as in Example 1.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.4% by mass, and the average particle size was 62 μm.

(Calcination of Dry Powder ($E_1$))

The calcination was carried out under the same calcination condition as in Example 1, except for altering the feed amount of the pre-stage calcined product in the main calcination to 36 g/hr. The reduction index of the pre-stage calcined product at this time was 10.3%, and the specific surface area of the calcined product after the main calcination was 12.0 $m^2/g$.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1N_{0.207}Sb_{0.219}Nb_{0.102}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 88.4%, and the yield of acrylonitrile was 55.2%.

Example 14

(Preparation of Dry Powder)

The preparation of a dry powder ($D_1$) was carried out by the same method as in Example 1.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.4% by mass, and the average particle size was 58 μm.

(Calcination of Dry Powder ($E_1$))

The calcination was carried out under the same calcination condition as in Example 1, except for altering the feed amount of the pre-stage calcined product in the main calcination to 84 g/hr. The reduction index of the pre-stage calcined product at this time was 10.4%, and the specific surface area of the calcined product after the main calcination was 14.0 $m^2/g$.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 88.4%, and the yield of acrylonitrile was 54.3%.

Example 15

(Preparation of Niobium Raw-material Solution)

A niobium raw-material solution was prepared by a method described below. 72.2 kg of niobic acid containing 77.9% by mass in terms of $Nb_2O_5$ and 267 kg of oxalic acid dihydrate [$H_2C_2O_4 \cdot 2H_2O$] were mixed in 500 kg of water. The molar ratio of the oxalic acid/niobium as feedstocks was 5.0, and the concentration of feedstock niobium was 0.552 (mol-Nb/kg-solution).

The resultant solution was heated for one hour at 95° C. with stirring, thereby obtaining an aqueous solution in which the niobium compound was dissolved. The aqueous solution was left standstill, cooled with ice, subjected to a suction filtration for removing a solid content, thereby obtaining a uniform niobium compound aqueous solution. The same operation was repeated several times; and the obtained niobium compound aqueous solutions were unified, thereby making a niobium raw-material solution. The molar ratio of oxalic acid/niobium of the niobium raw-material solution was 2.40 by the analysis described below.

10 g of this niobium raw-material solution was precisely weighed and put in a crucible, dried for a night at 95° C., and subjected to a heat treatment for one hour at 600° C., thereby obtaining 0.835 g of $Nb_2O_5$. From this result, the niobium concentration was 0.590 (mol-Nb/kg-solution).

3 g of this niobium raw-material solution was precisely weighed and put in a glass beaker having a capacity of 300 mL; and 200 mL of hot water having a temperature of about 80° C. was added, and 10 mL of a 1:1 sulfuric acid was then added. The resultant solution was titrated by using a 1/4 N $KMnO_4$ solution with stirring while being kept at a temperature of 70° C. on a hot stirrer. A point at which a faint light pink color by $KMnO_4$ lasted for about 30 seconds or more was defined as an end-point. The concentration of oxalic acid was determined on the basis of the resultant titer in accordance with the following formula and, as a result, it was 1.50 (mol-oxalic acid/kg).

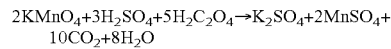

$$2KMnO_4 + 3H_2SO_4 + 5H_2C_2O_4 \rightarrow K_2SO_4 + 2MnSO_4 + 10CO_2 + 8H_2O$$

The present step was repeated and the obtained niobium raw-material solutions were used as niobium raw-material solutions in the following productions of composite oxide catalysts.

(Preparation of Dry Powder)

30.24 kg of ammonium heptamolybdate [$(NH_4)_6Mo_7O_{24} \cdot 4H_2O$], 4.19 kg of ammonium metavanadate [$NH_4VO_3$], 5.52 kg of diantimony trioxide [$Sb_2O_3$], and further a solution in which 371 g of cerium nitrate [$Ce(NO_3)_3 \cdot 6H_2O$] was dissolved in 26 kg of water were added to 100 kg of water, and heated under stirring for one hour at 95° C., thereby obtaining an aqueous mixed-solution (A-1).

3.42 kg of a hydrogen peroxide solution containing 30% by mass in terms of $H_2O_2$ was added to 29.9 kg of the niobium raw-material solution. The mixture was stirred and mixed at a solution temperature being kept at about 20° C., thereby obtaining an aqueous solution (B-1).

The obtained aqueous mixed-solution (A-1) was cooled to 70° C., and 56.55 kg of silica sol containing 32.0% by mass in terms of $SiO_2$ was thereafter added. Then, 6.44 kg of a hydrogen peroxide solution containing 30% by mass in terms of $H_2O_2$ was added, and stirred and mixed for one hour at 50° C.; and thereafter, 2.38 kg of an aqueous solution of ammonium metatungstate was dissolved, and the aqueous solution (B-1) was then added. A solution in which 14.81 kg of a fumed silica was dispersed in 214.7 kg of water was added thereto, and aged for 2.5 hours at 50° C. with stirring, thereby obtaining a slurry aqueous mixed-solution ($C_1$) as a raw material-formulated solution.

The obtained aqueous mixed-solution ($C_1$) was fed and dried in a centrifugal spray dryer, thereby obtaining a microspherical dry powder ($D_1$). The temperature at the inlet of the dryer was 210° C., and the temperature at the outlet thereof was 120° C.

In order to carry out a step of "calcination of a dry powder ($E_1$)" described later in a continuous system, the present step was repeated 38 times, thereby preparing the total of about 2600 kg of the dry powder ($D_1$).

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.8% by mass, and the average particle size was 55 μm.

(Calcination of Dry Powder ($E_1$))

The obtained dry powder ($E_1$) was fed at a rate of 20 kg/hr to a continuous-type cylindrical calcining tube made of SUS, having an inner diameter of 500 mm, a length of 3500 mm and a thickness of 20 mm in a rotary furnace, and provided with seven weir plates having a height of 150 mm so that the length of the heating section was divided into eight equal sections. A nitrogen gas was flowed at 600 NL/min in the calcining tube, and the temperature of the heating furnace was adjusted so as to have a temperature profile of being raised up to 370° C. over about four hours and kept at 370° C. for three hours while the calcining tube was being rotated at 4 rpm, to pre-stage calcine the dry powder, thereby obtaining a pre-stage calcined product. A calcination was carried out on the obtained pre-stage calcined product under the same main calcination condition as shown in Example 1. The reduction index of the pre-stage calcined product was 10.2%, and the specific surface area of the calcined product after the main calcination was 13.5 $m^2/g$.

(Removal of Protrusions)

Protrusions were removed under the same condition as in Example 1, and the compositional ratios of a/b and a/c of the composite oxide catalyst ($G_1$) were measured by fluorescent X-ray analysis. The composition of the composite oxide catalyst ($G_1$) obtained at this time was $Mo_1V_{0.207}Sb_{0.219}Nb_{0.102}W_{0.030}Ce_{0.005}O_n$/51.0 wt %-$SiO_2$.

X-ray diffractometry of the composite oxide catalyst ($G_1$) was carried out. At this time, a peak of $2\theta=8.9°$ was paid attention to, and the crystal grain diameter was measured from Scherrer equation, and was 48 nm.

(Ammoxidation Reaction of Propane)

The reaction was carried out under the same condition as in Example 1; and the propane conversion after the reaction was 89.1%, and the yield of acrylonitrile was 55.0%. The reaction was carried out continuously for 30 days using the catalyst, and the yield of acrylonitrile was 55.3%.

Example 16

A niobium raw-material solution was prepared by the same method as the preparation method used in Example 15.

(Preparation of Dry Powder)

A dry powder ($D_1$) was prepared by the same method as in Example 15.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.4% by mass, and the average particle size was 53 μm.

(Calcination of Dry Powder ($E_1$))

The obtained dry powder ($E_1$) was fed at a rate of 20 kg/hr to a continuous-type cylindrical calcining tube made of SUS, having an inner diameter of 500 mm, a length of 3500 mm and a thickness of 20 mm in a rotary furnace, and provided with seven weir plates having a height of 150 mm so that the length of the heating section was divided into eight equal sections. A nitrogen gas was flowed at 600 NL/min in the calcining tube, and the temperature of the heating furnace was adjusted so as to have a temperature profile of being raised up to 370° C. over about four hours and kept at 370° C. for three hours while the calcining tube was being rotated at 4 rpm, to pre-stage calcine the dry powder, thereby obtaining a pre-stage calcined product. Then, the pre-stage calcined product was fed at a rate of 15 kg/hr in another cylindrical calcining tube made of SUS, having an inner diameter of 500 mm, a length of 3500 mm and a thickness of 20 mm in a rotary furnace, and provided with seven weir plates having a height of 150 mm so that the length of the heating section was divided into eight equal sections, while the tube was being rotated at 4 rpm. At this time, while a portion of the pre-stage calcined product inlet side of the calcining tube (a portion not being covered with the heating furnace) was hammered once at every five seconds from a height of 250 mm above the calcining tube in the direction perpendicular to the rotation axis by a hammering device equipped with a hammer of 14 kg in mass with a hammering tip end made of SUS, and under a nitrogen gas flow at 500 NL/min, the temperature of the heating furnace was adjusted so as to have a temperature profile of being raised up to 675° C. at 2° C./min, kept at 675° C. for two hours for calcination, and descended at 1° C./min, to carry out a main calcination of the pre-stage calcined product, thereby obtaining a calcined product. The reduction index of the pre-stage calcined product obtained in this process was 10.1%, and the specific surface area of the calcined product after the main calcination was 15.2 $m^2/g$.

(Removal of Protrusions)

1800 kg of the calcined product was put in an apparatus as shown in FIG. 1, which was adjusted to exhibit an energy conversion value per catalyst mass ($m^5/sec^2/kg$) at 15° C. and 1 atm of 50, and operated for 24 hours. The length of the air flow in the air flow direction at this time was 390 mm, and the average line speed of the air flow was 341 m/sec; and the number K of holes as air flow holes was 350. The compositional ratios of a/b and a/c of the composite oxide catalyst ($G_1$) after the removal of protrusions were measured by fluorescent X-ray analysis. The results acquired are shown in Table 1. The composition of the composite oxide catalyst ($G_1$) obtained at this time was $Mo_1N_{0.207}Sb_{0.219}Nb_{0.102}W_{0.030}Ce_{0.005}O_n$/51.0 wt %-$SiO_2$.
(Ammoxidation Reaction of Propane)

The reaction was carried out under the same condition as in Example 1; and the propane conversion after the reaction was 89.1%, and the yield of acrylonitrile was 55.2%.

Example 17

(Preparation of Dry Powder)

A dry powder ($D_1$) was prepared in the same manner as in Example 1, except for altering the addition amount of the aqueous solution of ammonium metatungstate to 93.0 g (purity: 50%).
(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.9% by mass, and the average particle size was 56 μm.
(Calcination of Dry Powder ($E_1$))

The calcination was carried out under the same calcination condition as in Example 1. The reduction index of the pre-stage calcined product at this time was 10.2%, and the specific surface area of the calcined product after the main calcination was 14.2 m²/g.
(Removal of Protrusions)

Protrusions were removed under the same condition as in Example 1, and the compositional ratios of a/b and a/c of the composite oxide catalyst ($G_1$) were measured by fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.090}Ce_{0.005}O_n$/51.0 wt %-$SiO_2$.
(Ammoxidation Reaction of Propane)

The reaction was carried out under the same condition as in Example 1; and the propane conversion after the reaction was 88.1%, and the yield of acrylonitrile was 55.2%.

Example 18

(Preparation of Dry Powder)

A dry powder ($D_1$) was prepared in the same manner as in Example 1, except for adding no aqueous solution of ammonium metatungstate.
(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.9% by mass, and the average particle size was 57 μm.
(Calcination of Dry Powder ($E_1$))

The calcination was carried out under the same calcination condition as in Example 1. The reduction index of the pre-stage calcined product at this time was 9.9%, and the specific surface area of the calcined product after the main calcination was 11.0 m²/g.
(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}Ce_{0.005}O_n$/51.0 wt %-$SiO_2$.
(Ammoxidation Reaction of Propane)

The reaction was carried out under the same condition as in Example 1; and the propane conversion after the reaction was 88.7%, and the yield of acrylonitrile was 54.4%.

Example 19

(Preparation of Dry Powder)

A dry powder ($D_1$) was prepared in the same manner as in Example 1, except for adding no cerium nitrate [$Ce(NO_3)_3 \cdot 6H_2O$].
(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.4% by mass, and the average particle size was 55 μm.
(Calcination of Dry Powder ($E_1$))

The calcination was carried out under the same calcination condition as in Example 1. The reduction index of the pre-stage calcined product at this time was 9.9%, and the specific surface area of the calcined product after the main calcination was 15.5 m²/g.
(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}O_n$/51.0 wt %-$SiO_2$.
(Ammoxidation Reaction of Propane)

The reaction was carried out under the same condition as in Example 1; and the propane conversion after the reaction was 89.5%, and the yield of acrylonitrile was 54.3%.

Example 20

(Preparation of Dry Powder)

A dry powder ($D_1$) was prepared in the same manner as in Example 1, except for altering the addition amount of cerium nitrate [$Ce(NO_3)_3 \cdot 6H_2O$] to 8.7 g.
(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.4% by mass, and the average particle size was 52 μm.
(Calcination of Dry Powder ($E_1$))

The calcination was carried out under the same calcination condition as in Example 1. The reduction index of the pre-stage calcined product at this time was 9.7%, and the specific surface area of the calcined product after the main calcination was 12.8 m²/g.
(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Ce_{0.009}O_n$/51.0 wt %-$SiO_2$.

(Ammoxidation Reaction of Propane)

The reaction was carried out under the same condition as in Example 1; and the propane conversion after the reaction was 89.1%, and the yield of acrylonitrile was 54.6%.

Example 21

(Preparation of Dry Powder)

A dry powder ($D_1$) was prepared in the same manner as in Example 1, except for adding 4.8 g of lanthanum nitrate [$La(NO_3)_3 \cdot 6H_2O$] in place of cerium nitrate [$Ce(NO_3)_3 \cdot 6H_2O$].

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.7% by mass, and the average particle size was 51 μm.

(Calcination of Dry Powder ($E_1$))

The calcination was carried out under the same calcination condition as in Example 1. The reduction index of the pre-stage calcined product at this time was 9.9%, and the specific surface area of the calcined product after the main calcination was 14.5 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}La_{0.005}O_n$/51.0 wt %-$SiO_2$.

(Ammoxidation Reaction of Propane)

The reaction was carried out under the same condition as in Example 1; and the propane conversion after the reaction was 88.8%, and the yield of acrylonitrile was 54.0%.

Example 22

(Preparation of Dry Powder)

A dry powder ($D_1$) was prepared in the same manner as in Example 1, except for adding 4.8 g of praseodymium nitrate [$Pr(NO_3)_3 \cdot 6H_2O$] in place of cerium nitrate [$Ce(NO_3)_3 \cdot 6H_2O$].

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.7% by mass, and the average particle size was 56 μm.

(Calcination of Dry Powder ($E_1$))

The calcination was carried out under the same calcination condition as in Example 1. The reduction index of the pre-stage calcined product at this time was 9.9%, and the specific surface area of the calcined product after the main calcination was 14.2 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Pr_{0.005}O_n$/51.0 wt %-$SiO_2$.

(Ammoxidation Reaction of Propane)

The reaction was carried out under the same condition as in Example 1; and the propane conversion after the reaction was 88.7%, and the yield of acrylonitrile was 54.1%.

Example 23

(Preparation of Dry Powder)

A dry powder ($D_1$) was prepared in the same manner as in Example 1, except for adding 4.6 g of ytterbium nitrate [$Yb(NO_3)_3 \cdot 3H_2O$] in place of cerium nitrate [$Ce(NO_3)_3 \cdot 6H_2O$].

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.6% by mass, and the average particle size was 58 μm.

(Calcination of Dry Powder ($E_1$))

The calcination was carried out under the same calcination condition as in Example 1. The reduction index of the pre-stage calcined product at this time was 9.9%, and the specific surface area of the calcined product after the main calcination was 14.0 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Yb_{0.005}O_n$/51.0 wt %-$SiO_2$.

(Ammoxidation Reaction of Propane)

The reaction was carried out under the same condition as in Example 1; and the propane conversion after the reaction was 88.8%, and the yield of acrylonitrile was 54.1%.

Example 24

(Preparation of Dry Powder)

A dry powder ($D_1$) was prepared in the same manner as in Example 1, except for altering the addition amount of diantimony trioxide [$Sb_2O_3$] to 93.5 g; that of the niobium mixed-solution ($B_0$) to 452.6 g; and that of the hydrogen peroxide solution, which was added together with the niobium mixed-solution ($B_0$), containing 30% by mass in terms of $H_2O_2$ to 79.3 g.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.7% by mass, and the average particle size was 53 μm.

(Calcination of Dry Powder ($E_1$))

The calcination was carried out under the same calcination condition as in Example 1. The reduction index of the pre-stage calcined product at this time was 10.8%, and the specific surface area of the calcined product after the main calcination was 14.8 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.243}Nb_{0.122}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 89.1%, and the yield of acrylonitrile was 54.8%.

Example 25

(Preparation of Dry Powder)

A dry powder ($D_1$) was prepared in the same manner as in Example 1, except for altering the amount of water to 1655 g; the addition amount of ammonium heptamolybdate [$(NH_4)_6Mo_7O_{24}\cdot 4H_2O$] to 459.2 g; that of ammonium metavanadate [$NH_4VO_3$] to 63.7 g; that of diantimony trioxide [$Sb_2O_3$] to 99.3 g; that of the niobium mixed-solution ($B_0$) to 363.6 g; and that of the hydrogen peroxide solution, which was added together with the niobium mixed-solution ($B_0$), containing 30% by mass in terms of $H_2O_2$ to 63.7 g.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.8% by mass, and the average particle size was 55 μm.

(Calcination of Dry Powder ($E_1$))

The calcination was carried out under the same calcination condition as in Example 1, except for altering the maximum calcination temperature in the pre-stage calcination to 350° C. and the maximum calcination temperature in the main calcination to 685° C. The reduction index of the pre-stage calcined product at this time was 9.9%, and the specific surface area of the calcined product after the main calcination was 11.0 m²/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.220}Sb_{0.258}Nb_{0.098}W_{0.030}Ce_{0.005}O_n$/51.0 wt %-$SiO_2$. X-ray diffractometry of the composite oxide was carried out. At this time, a peak of 2θ=8.9° was paid attention to, and the crystal grain diameter was measured from Scherrer equation, and was 55 nm.

(Ammoxidation Reaction of Propane)

The reaction was carried out under the same condition as in Example 1; and the propane conversion after the reaction was 88.3%, and the yield of acrylonitrile was 54.6%.

Example 26

(Preparation of Dry Powder)

A dry powder ($D_1$) was prepared by the same method as in Example 1, except for altering the addition amount of diantimony trioxide [$Sb_2O_3$] to 80.8 g; that of the niobium mixed-solution ($B_0$) to 337.6 g; and that of the hydrogen peroxide solution, which was added together with the niobium mixed-solution ($B_0$), containing 30% by mass in terms of $H_2O_2$ to 59.2 g.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.4% by mass, and the average particle size was 49 μm.

(Calcination of Dry Powder ($E_1$))

The calcination was carried out under the same calcination condition as in Example 1, except for altering the maximum calcination temperature in the pre-stage calcination to 350° C. and the maximum calcination temperature in the main calcination to 690° C. The reduction index of the pre-stage calcined product at this time was 9.9%, and the specific surface area of the calcined product after the main calcination was 11.0 m²/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.210}Nb_{0.091}W_{0.030}Ce_{0.005}O_n$/51.0 wt %-$SiO_2$.

X-ray diffractometry of the composite oxide catalyst was carried out. At this time, a peak of 2θ=8.9° was paid attention to, and the crystal grain diameter was measured from Scherrer equation, and was 65 nm.

(Ammoxidation Reaction of Propane)

The reaction was carried out under the same condition as in Example 1; and the propane conversion after the reaction was 89.0%, and the yield of acrylonitrile was 54.5%.

Example 27

(Preparation of Dry Powder)

A dry powder ($D_1$) was prepared in the same manner as in Example 1, except for altering the addition amount of diantimony trioxide [$Sb_2O_3$] to 81.2 g; that of the niobium mixed-solution ($B_0$) to 445.2 g; and that of the hydrogen peroxide solution, which was added together with the niobium mixed-solution ($B_0$), containing 30% by mass in terms of $H_2O_2$ to 78.0 g.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.4% by mass, and the average particle size was 54 μm.

(Calcination of Dry Powder ($E_1$))

The calcination was carried out under the same calcination condition as in Example 1. The reduction index of the pre-stage calcined product at this time was 10.7%, and the specific surface area of the calcined product after the main calcination was 15.6 m²/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1N_{0.207}Sb_{0.211}Nb_{0.120}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 89.0%, and the yield of acrylonitrile was 55.5%.

Example 28

(Preparation of Dry Powder)

A dry powder ($D_1$) was prepared in the same manner as in Example 1, except for altering the addition amount of diantimony trioxide [$Sb_2O_3$] to 81.2 g; that of the niobium mixed-solution ($B_0$) to 519.4 g; and that of the hydrogen peroxide solution, which was added together with the niobium mixed-solution ($B_0$), containing 30% by mass in terms of $H_2O_2$ to 91.0 g.
(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.6% by mass, and the average particle size was 55 μm.
(Calcination of Dry Powder ($E_1$))

The calcination was carried out under the same calcination condition as in Example 1, except for altering the maximum calcination temperature in the pre-stage calcination to 385° C. and the maximum calcination temperature in the main calcination to 680° C. The reduction index of the pre-stage calcined product at this time was 11.0%, and the specific surface area of the calcined product after the main calcination was 16.0 m$^2$/g.
(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.211}Nb_{0.140}W_{0.030}Ce_{0.005}O_n$/51.0 wt %-$SiO_2$.

X-ray diffractometry of the composite oxide catalyst was carried out. At this time, a peak of 2θ=8.9° was paid attention to, and the crystal grain diameter was measured from Scherrer equation, and was 46 nm.
(Ammoxidation Reaction of Propane)

The reaction was carried out under the same condition as in Example 1; and the propane conversion after the reaction was 87.4%, and the yield of acrylonitrile was 54.6%.

Example 29

(Preparation of Dry Powder)

A dry powder ($D_1$) was prepared in the same manner as in Example 1, except for altering the addition amount of diantimony trioxide [$Sb_2O_3$] to 93.5 g; that of the niobium mixed-solution ($B_0$) to 519.4 g; and that of the hydrogen peroxide solution, which was added together with the niobium mixed-solution ($B_0$), containing 30% by mass in terms of $H_2O_2$ to 91.0 g.
(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.5% by mass, and the average particle size was 53 μm.
(Calcination of Dry Powder ($E_1$))

The calcination was carried out under the same calcination condition as in Example 1, except for altering the maximum calcination temperature in the pre-stage calcination to 385° C. and the maximum calcination temperature in the main calcination to 680° C. The reduction index of the pre-stage calcined product at this time was 11.3%, and the specific surface area of the calcined product after the main calcination was 15.0 m$^2$/g.
(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.243}Nb_{0.140}W_{0.030}Ce_{0.005}O_n$/51.0 wt %-$SiO_2$.

X-ray diffractometry of the composite oxide catalyst was carried out. At this time, a peak of 2θ=8.9° was paid attention to, and the crystal grain diameter was measured from Scherrer equation, and was 45 nm.
(Ammoxidation Reaction of Propane)

The reaction was carried out under the same condition as in Example 1; and the propane conversion after the reaction was 87.2%, and the yield of acrylonitrile was 54.4%.

Example 30

(Preparation of Dry Powder)

A dry powder ($D_1$) was prepared in the same manner as in Example 1, except for altering the amount of water to 1505 g; the addition amount of ammonium heptamolybdate [$(NH_4)_6Mo_7O_{24}·4H_2O$] to 417.5 g; that of ammonium metavanadate [$NH_4VO_3$] to 57.9 g; that of diantimony trioxide [$Sb_2O_3$] to 87.4 g; that of the niobium mixed-solution ($B_0$) to 341.3 g; and that of the hydrogen peroxide solution, which was added together with the niobium mixed-solution ($B_0$), containing 30% by mass in terms of $H_2O_2$ to 59.8 g.
(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.8% by mass, and the average particle size was 50 μm.
(Calcination of Dry Powder ($E_1$))

The calcination was carried out under the same calcination condition as in Example 1, except for altering the maximum calcination temperature in the main calcination to 680° C. The reduction index of the pre-stage calcined product at this time was 10.1%, and the specific surface area of the calcined product after the main calcination was 14.3 m$^2$/g.
(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.200}Sb_{0.227}Nb_{0.092}W_{0.030}Ce_{0.005}O_n$/51.0 wt %-$SiO_2$.
(Ammoxidation Reaction of Propane)

The reaction was carried out under the same condition as in Example 1; and the propane conversion after the reaction was 88.3%, and the yield of acrylonitrile was 55.1%.

Example 31

(Preparation Of Dry Powder)

A dry powder ($D_1$) was prepared in the same manner as in Example 1, except for altering the amount of water to 1505 g; the addition amount of ammonium heptamolybdate [$(NH_4)_6Mo_7O_{24}·4H_2O$] to 417.5 g; that of ammonium metavanadate [$NH_4VO_3$] to 57.9 g; that of diantimony trioxide [$Sb_2O_3$] to 87.4 g; that of the niobium mixed-solution ($B_0$) to 426.6 g; and that of the hydrogen peroxide solution, which was added together with the niobium mixed-solution ($B_0$), containing 30% by mass in terms of $H_2O_2$ to 74.8 g.
(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.8% by mass, and the average particle size was 52 μm.

(Calcination of Dry Powder ($E_1$))

The calcination was carried out under the same calcination condition as in Example 1, except for altering the maximum calcination temperature in the main calcination to 680° C. The reduction index of the pre-stage calcined product at this time was 10.0%, and the specific surface area of the calcined product after the main calcination was 13.8 $m^2/g$.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.200}Sb_{0.227}Nb_{0.115}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 88.3%, and the yield of acrylonitrile was 55.2%.

Example 32

(Preparation of Dry Powder)

The preparation of a dry powder ($D_1$) was carried out by the same method as in Example 1.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.4% by mass, and the average particle size was 55 μm.

(Calcination of Dry Powder ($E_1$))

The calcination condition was altered as follows: the feed amount of the dry powder ($E_1$) in the pre-stage calcination was altered to 70 g/hr; the total nitrogen flow rate in the pre-stage calcination, to 0.8 NL/min (the counterflow and the concurrent flow were each 0.4 NL/min); and the maximum calcination temperature in the pre-stage calcination, to 400° C. The feed amount of the pre-stage calcined product in the main calcination was altered to 51 g/hr; and the maximum calcination temperature in the main calcination was altered to 695° C. The calcination was carried out under the same calcination condition as in Example 1, except for these alterations. The reduction index of the pre-stage calcined product at this time was 10.2%, and the specific surface area of the calcined product after the main calcination was 8.0 $m^2/g$.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.102}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 88.4%, and the yield of acrylonitrile was 53.8%.

Example 33

(Preparation of Dry Powder)

A dry powder ($D_1$) was prepared in the same manner as in Example 1, except for altering the addition amount of the niobium mixed-solution ($B_0$) to 500.8 g, and that of the hydrogen peroxide solution, which was added together with the niobium mixed-solution ($B_0$), containing 30% by mass in terms of $H_2O_2$ to 87.8 g.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.4% by mass, and the average particle size was 49 μm.

(Calcination of Dry Powder ($E_1$))

The calcination was carried out under the same calcination condition as in Example 1, except for altering the maximum calcination temperature in the main calcination to 670° C. The reduction index of the pre-stage calcined product at this time was 11.2%, and the specific surface area of the calcined product after the main calcination was 14.8 $m^2/g$.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.135}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 87.5%, and the yield of acrylonitrile was 54.4%. The reaction was carried out continuously for 30 days using the catalyst, and the yield of acrylonitrile was 54.6%.

Example 34

(Preparation of Dry Powder)

A dry powder ($D_1$) was prepared in the same manner as in Example 1, except for altering the amount of water to 1520 g; the addition amount of ammonium heptamolybdate [$(NH_4)_6Mo_7O_{24}\cdot 4H_2O$] to 421.7 g; that of ammonium metavanadate [$NH_4VO_3$] to 58.5 g; that of the niobium mixed-solution ($B_0$) to 437.8 g; and that of the hydrogen peroxide solution, which was added together with the niobium mixed-solution ($B_0$), containing 30% by mass in terms of $H_2O_2$ to 76.7 g.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.7% by mass, and the average particle size was 50 μm.

(Calcination of Dry Powder ($E_1$))

The calcination was carried out under the same condition as in Example 1, except for altering the maximum calcination temperature in the main calcination to 670° C. The reduction index of the pre-stage calcined product at this time was 10.8%, and the specific surface area of the calcined product after the main calcination was 14.3 $m^2/g$.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.202}Sb_{0.219}Nb_{0.118}W_{0.030}Ce_{0.005}O_n/51.0$ wt %-$SiO_2$.
(Ammoxidation Reaction of Propane)

The reaction was carried out under the same condition as in Example 1; and the propane conversion after the reaction was 87.6%, and the yield of acrylonitrile was 52.8%. The reaction was carried out continuously for 30 days using the catalyst, and the yield of acrylonitrile was 54.8%.

Example 35

(Preparation of Dry Powder)

A dry powder ($D_1$) was prepared in the same manner as in Example 1, except for altering the addition amount of the niobium mixed-solution ($B_0$) to 341.3 g; and that of the hydrogen peroxide solution, which was added together with the niobium mixed-solution ($B_0$), containing 30% by mass in terms of $H_2O_2$ to 59.8 g.
(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.2% by mass, and the average particle size was 52 μm.
(Calcination of Dry Powder ($E_1$))

The calcination was carried out under the same calcination condition as in Example 1, except for altering the maximum calcination temperature in the main calcination to 685° C. The reduction index of the pre-stage calcined product at this time was 9.5%, and the specific surface area of the calcined product after the main calcination was 13.5 m²/g.
(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.092}W_{0.030}Ce_{0.005}O_n/51.0$ wt %-$SiO_2$.
(Ammoxidation Reaction of Propane)

The reaction was carried out under the same condition as in Example 1; and the propane conversion after the reaction was 89.6%, and the yield of acrylonitrile was 55.4%. The reaction was carried out continuously for 30 days using the catalyst, and the yield of acrylonitrile was 54.5%.

Comparative Example 1

(Preparation of Dry Powder)

A dry powder ($D_1$) was produced as follows.

438.4 g of ammonium heptamolybdate [$(NH_4)_6Mo_7O_{24}.4H_2O$], 60.8 g of ammonium metavanadate [$NH_4VO_3$], 107.8 g of diantimony trioxide [$Sb_2O_3$], and further 4.8 g of cerium nitrate [$Ce(NO_3)_3.6H_2O$] were added to 1.580 kg of water, and heated under stirring for one hour at 95° C., thereby preparing an aqueous raw-material solution ($A_1$).

65.0 g of a hydrogen peroxide solution containing 30% by mass in terms of $H_2O_2$ was added to 371.0 g of a niobium mixed-solution ($B_0$) prepared in the same manner as in Example 1, and was stirred and mixed for 10 minutes at room temperature, thereby preparing an aqueous raw-material solution ($B_1$).

The obtained aqueous raw-material solution ($A_1$) was cooled to 70° C., and 807.8 g of silica sol containing 34.0% by mass in terms of $SiO_2$ was thereafter added; 98.4 g of a hydrogen peroxide solution containing 30% by mass in terms of $H_2O_2$ was further added, and continuously stirred for 30 minutes at 55° C. Then, the aqueous raw-material solution ($B_1$), 31.0 g of an aqueous solution of ammonium metatungstate (purity: 50%), and a dispersion liquid in which 211.5 g of silica powder was dispersed in 2.855 kg of water were sequentially added thereto, and then aged for 2.5 hours at 50° C. with stirring, thereby obtaining a slurry aqueous mixed-solution ($C_1$).

The obtained aqueous mixed-solution ($C_1$) was fed and dried in a centrifugal spray dryer, thereby obtaining a microspherical dry powder ($D_1$). The temperature at the inlet of the dryer was 210° C., and the temperature at the outlet thereof was 120° C.
(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.9% by mass, and the average particle size was 50 μm.
(Calcination of Dry Powder ($E_1$))

The calcination was carried out under the same calcination condition as in Example 1, except for altering the maximum calcination temperature in the pre-stage calcination to 390° C. and the maximum calcination temperature in the main calcination to 695° C. The reduction index of the pre-stage calcined product at this time was 9.2%, and the specific surface area of the calcined product after the main calcination was 9.0 m²/g.
(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.210}Sb_{0.280}Nb_{0.100}W_{0.030}Ce_{0.005}O_n/51.0$ wt %-$SiO_2$.
(Ammoxidation Reaction of Propane)

The reaction was carried out under the same condition as in Example 1; and the propane conversion after the reaction was 86.0%, and the yield of acrylonitrile was 51.5%. The reaction was carried out continuously for 30 days using the catalyst, and the yield of acrylonitrile was 49.0%.

Comparative Example 2

(Preparation of Dry Powder)

A dry powder ($D_1$) was produced as follows.

480.1 g of ammonium heptamolybdate [$(NH_4)_6Mo_7O_{24}.4H_2O$], 66.6 g of ammonium metavanadate [$NH_4VO_3$], 84.7 g of diantimony trioxide [$Sb_2O_3$], and further 4.8 g of cerium nitrate [$Ce(NO_3)_3.6H_2O$] were added to 1.730 kg of water, and heated under stirring for one hour at 95° C., thereby preparing an aqueous raw-material solution ($A_1$).

58.5 g of a hydrogen peroxide solution containing 30% by mass in terms of $H_2O_2$ was added to 333.9 g of a niobium mixed-solution ($B_0$) prepared in the same manner as in Example 1, and was stirred and mixed for 10 minutes at room temperature, thereby preparing an aqueous raw-material solution ($B_1$).

The obtained aqueous raw-material solution ($A_1$) was cooled to 70° C., and 807.8 g of silica sol containing 34.0% by mass in terms of $SiO_2$ was thereafter added; 98.4 g of a hydrogen peroxide solution containing 30% by mass in terms of $H_2O_2$ was further added, and continuously stirred for 30 minutes at 55° C. Then, the aqueous raw-material solution ($B_1$), 31.0 g of an aqueous solution of ammonium metatungstate (purity: 50%), and a dispersion liquid in which 211.5 g of silica powder was dispersed in 2.855 kg of water were sequentially added thereto, and then aged for 2.5 hours at 50° C. with stirring, thereby obtaining a slurry aqueous mixed-solution ($C_1$) as a raw material-formulated solution.

The obtained aqueous mixed-solution ($C_1$) was fed and dried in a centrifugal spray dryer, thereby obtaining a microspherical dry powder ($D_1$). The temperature at the inlet of the dryer was 210° C., and the temperature at the outlet thereof was 120° C.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.9% by mass, and the average particle size was 52 μm.

(Calcination of Dry Powder ($E_1$))

The calcination was carried out under the same calcination condition as in Example 1, except for altering the maximum calcination temperature in the pre-stage calcination to 345° C. and the maximum calcination temperature in the main calcination to 650° C. The reduction index of the pre-stage calcined product at this time was 9.8%, and the specific surface area of the calcined product after the main calcination was 11.5 m²/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.230}Sb_{0.220}Nb_{0.090}W_{0.030}Ce_{0.005}O_n$/51.0 wt %-$SiO_2$.

X-ray diffractometry of the composite oxide catalyst was carried out. At this time, a peak of 2θ=8.9° was paid attention to, and the crystal grain diameter was measured from Scherrer equation, and was 35 nm.

(Ammoxidation Reaction of Propane)

The reaction was carried out under the same condition as in Example 1; and the propane conversion after the reaction was 84.0%, and the yield of acrylonitrile was 52.3%.

Comparative Example 3

(Preparation of Dry Powder)

A dry powder ($D_1$) was produced as follows.

480.1 g of ammonium heptamolybdate [$(NH_4)_6Mo_7O_{24}.4H_2O$], 66.6 g of ammonium metavanadate [$NH_4VO_3$], 100.1 g of diantimony trioxide [$Sb_2O_3$], and further 4.8 g of cerium nitrate [$Ce(NO_3)_3.6H_2O$] were added to 1.730 kg of water, and heated under stirring for one hour at 95° C., thereby preparing an aqueous raw-material solution ($A_1$).

58.5 g of a hydrogen peroxide solution containing 30% by mass in terms of $H_2O_2$ was added to 333.9 g of a niobium mixed-solution ($B_0$) prepared in the same manner as in Example 1, and was stirred and mixed for 10 minutes at room temperature thereby preparing an aqueous raw-material solution ($B_1$).

The obtained aqueous raw-material solution ($A_1$) was cooled to 70° C., and 807.8 g of silica sol containing 34.0% by mass in terms of $SiO_2$ was thereafter added; 98.4 g of a hydrogen peroxide solution containing 30% by mass in terms of $H_2O_2$ was further added, and continuously stirred for 30 minutes at 55° C. Then, the aqueous raw-material solution ($B_1$), 31.0 g of an aqueous solution of ammonium metatungstate (purity: 50%), and a dispersion liquid in which 211.5 g of silica powder was dispersed in 2.855 kg of water were sequentially added thereto, and then aged for 2.5 hours at 50° C. with stirring thereby obtaining a slurry aqueous mixed-solution ($C_1$) as a raw material-formulated solution.

The obtained aqueous mixed-solution ($C_1$) was fed and dried in a centrifugal spray dryer, thereby obtaining a microspherical dry powder ($D_1$). The temperature at the inlet of the dryer was 210° C., and the temperature at the outlet thereof was 120° C.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.3% by mass, and the average particle size was 56 μm.

(Calcination of Dry Powder ($E_1$))

The calcination was carried out under the same calcination condition as in Example 1, except for altering the maximum calcination temperature in the pre-stage calcination to 390° C. and the maximum calcination temperature in the main calcination to 695° C. The reduction index of the pre-stage calcined product at this time was 9.6%, and the specific surface area of the calcined product after the main calcination was 9.5 m²/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.230}Sb_{0.260}Nb_{0.090}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 81.2%, and the yield of acrylonitrile was 52.0%.

Comparative Example 4

(Preparation of Dry Powder)

A dry powder ($D_1$) was produced as follows.

417.5 g of ammonium heptamolybdate [$(NH_4)_6Mo_7O_{24}.4H_2O$], 57.9 g of ammonium metavanadate [$NH_4VO_3$], 100.1 g of diantimony trioxide [$Sb_2O_3$], and further 4.8 g of cerium nitrate [$Ce(NO_3)_3.6H_2O$] were added to 1.505 kg of water, and heated under stirring for one hour at 95° C., thereby preparing an aqueous raw-material solution ($A_1$).

91.0 g of a hydrogen peroxide solution containing 30% by mass in terms of $H_2O_2$ was added to 519.4 g of a niobium mixed-solution ($B_0$) prepared in the same manner as in Example 1, and was stirred and mixed for 10 minutes at room temperature, thereby preparing an aqueous raw-material solution ($B_1$).

The obtained aqueous raw-material solution ($A_1$) was cooled to 70° C., and 807.8 g of silica sol containing 34.0% by mass in terms of $SiO_2$ was thereafter added; 98.4 g of a hydrogen peroxide solution containing 30% by mass in terms of $H_2O_2$ was further added, and continuously stirred for 30 minutes at 55° C. Then, the aqueous raw-material solution ($B_1$), 31.0 g of an aqueous solution of ammonium metatungstate (purity: 50%), and a dispersion liquid in which 211.5 g of silica powder was dispersed in 2.855 kg of water were sequentially added thereto, and then aged for 2.5 hours at 50° C. with stirring, thereby obtaining a slurry aqueous mixed-solution ($C_1$) as a raw material-formulated solution.

The obtained aqueous mixed-solution ($C_1$) was fed and dried in a centrifugal spray dryer, thereby obtaining a microspherical dry powder ($D_1$). The temperature at the inlet of the dryer was 210° C., and the temperature at the outlet thereof was 120° C.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.3% by mass, and the average particle size was 54 μm.

(Calcination of Dry Powder ($E_1$))

The calcination was carried out under the same calcination condition as in Example 1, except for altering the maximum calcination temperature in the pre-stage calcination to 340° C. and the maximum calcination temperature in the main calcination to 640° C. The reduction index of the pre-stage calcined product at this time was 10.8%, and the specific surface area of the calcined product after the main calcination was 15.2 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.200}Sb_{0.260}Nb_{0.140}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 82.0%, and the yield of acrylonitrile was 51.5%.

Comparative Example 5

(Preparation of Dry Powder)

A dry powder ($D_1$) was produced as follows.

432.1 g of ammonium heptamolybdate [$(NH_4)_6Mo_7O_{24}.4H_2O$], 59.9 g of ammonium metavanadate [$NH_4VO_3$], 84.3 g of diantimony trioxide [$Sb_2O_3$], and further 4.8 g of cerium nitrate [$Ce(NO_3)_3.6H_2O$] were added to 1.557 kg of water, and heated under stirring for one hour at 95° C., thereby preparing an aqueous raw-material solution ($A_1$).

100.8 g of a hydrogen peroxide solution containing 30% by mass in terms of $H_2O_2$ was added to 575.0 g of a niobium mixed-solution ($B_0$) prepared in the same manner as in Example 1, and was stirred and mixed for 10 minutes at room temperature, thereby preparing an aqueous raw-material solution ($B_1$).

The obtained aqueous raw-material solution ($A_1$) was cooled to 70° C., and 807.8 g of silica sol containing 34.0% by mass in terms of $SiO_2$ was thereafter added; 98.4 g of a hydrogen peroxide solution containing 30% by mass in terms of $H_2O_2$ was further added, and continuously stirred for 30 minutes at 55° C. Then, the aqueous raw-material solution ($B_1$), 31.0 g of an aqueous solution of ammonium metatungstate (purity: 50%), and a dispersion liquid in which 211.5 g of silica powder was dispersed in 2.855 kg of water were sequentially added thereto, and then aged for 2.5 hours at 50° C. with stirring, thereby obtaining a slurry aqueous mixed-solution ($C_1$) as a raw material-formulated solution.

The obtained aqueous mixed-solution ($C_1$) was fed and dried in a centrifugal spray dryer, thereby obtaining a microspherical dry powder ($D_1$). The temperature at the inlet of the dryer was 210° C., and the temperature at the outlet thereof was 120° C.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.3% by mass, and the average particle size was 53 μm.

(Calcination of Dry Powder ($E_1$))

The calcination was carried out under the same calcination condition as in Example 1, except for altering the maximum temperature in the pre-stage calcination to 400° C. and the maximum temperature in the main calcination to 700° C. The reduction index of the pre-stage calcined product at this time was 11.5%, and the specific surface area of the calcined product after the main calcination was 15.0 m$^2$/g.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.219}Nb_{0.155}W_{0.030}Ce_{0.005}O_n$/51.0 wt %-$SiO_2$.

(Ammoxidation Reaction of Propane)

The reaction was carried out under the same condition as in Example 1; and the propane conversion after the reaction was 81.7%, and the yield of acrylonitrile was 48.5%. The reaction was carried out continuously for 30 days using the catalyst, and the yield of acrylonitrile was 46.5%.

Comparative Example 6

(Preparation of Dry Powder)

A dry powder ($D_1$) was produced as follows.

432.1 g of ammonium heptamolybdate [$(NH_4)_6Mo_7O_{24}.4H_2O$], 59.9 g of ammonium metavanadate [$NH_4VO_3$], 75.1 g of diantimony trioxide [$Sb_2O_3$], and further 4.8 g of cerium nitrate [$Ce(NO_3)_3.6H_2O$] were added to 1.557 kg of water, and heated under stirring for one hour at 95° C., thereby preparing an aqueous raw-materials solution ($A_1$).

84.5 g of a hydrogen peroxide solution containing 30% by mass in terms of $H_2O_2$ was added to 482.3 g of a niobium mixed-solution ($B_0$) prepared in the same manner as in Example 1, and was stirred and mixed for 10 minutes at room temperature, thereby preparing an aqueous raw-material solution ($B_1$).

The obtained aqueous raw-material solution ($A_1$) was cooled to 70° C., and 807.8 g of silica sol containing 34.0% by mass in terms of $SiO_2$ was thereafter added; 98.4 g of a hydrogen peroxide solution containing 30% by mass in terms of $H_2O_2$ was further added, and continuously stirred for 30 minutes at 55° C. Then, the aqueous raw-material solution ($B_1$), 31.0 g of an aqueous solution of ammonium metatungstate (purity: 50%), and a dispersion liquid in which 211.5 g of silica powder was dispersed in 2.855 kg of water were sequentially added thereto, and then aged for 2.5 hours at 50° C. with stirring, thereby obtaining a slurry aqueous mixed-solution ($C_1$) as a raw material-formulated solution.

The obtained aqueous mixed-solution ($C_1$) was fed and dried in a centrifugal spray dryer, thereby obtaining a microspherical dry powder ($D_1$). The temperature at the inlet of the dryer was 210° C., and the temperature at the outlet thereof was 120° C.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.3% by mass, and the average particle size was 56 μm.

(Calcination of Dry Powder ($E_1$))

The calcination was carried out under the same calcination condition as in Example 1, except for altering the maximum calcination temperature in the pre-stage calcination to 370° C. and the maximum calcination temperature in the main calcination to 680° C. The reduction index of the pre-stage calcined product at this time was 11.2%, and the specific surface area of the calcined product after the main calcination was 14.2 $m^2/g$.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.207}Sb_{0.195}Nb_{0.130}W_{0.030}Ce_{0.005}O_n/51.0$ wt %-$SiO_2$.

(Ammoxidation Reaction of Propane)

The reaction was carried out under the same condition as in Example 1; and the propane conversion after the reaction was 82.3%, and the yield of acrylonitrile was 51.6%.

Comparative Example 7

(Preparation of Dry Powder)

A dry powder ($D_1$) was produced as follows.

417.5 g of ammonium heptamolybdate [$(NH_4)_6Mo_7O_{24}\cdot 4H_2O$], 57.9 g of ammonium metavanadate [$NH_4VO_3$], 94.3 g of diantimony trioxide [$Sb_2O_3$], and further 4.8 g of cerium nitrate [$Ce(NO_3)_3\cdot 6H_2O$] were added to 1.505 kg of water, and heated under stirring for one hour at 95° C., thereby preparing an aqueous raw-material solution ($A_1$).

53.3 g of a hydrogen peroxide solution containing 30% by mass in terms of $H_2O_2$ was added to 304.2 g of a niobium mixed-solution ($B_0$) prepared in the same manner as in Example 1, and was stirred and mixed for 10 minutes at room temperature, thereby preparing an aqueous raw-material solution ($B_1$).

The obtained aqueous raw-material solution ($A_1$) was cooled to 70° C., and 807.8 g of silica sol containing 34.0% by mass in terms of $SiO_2$ was thereafter added; 98.4 g of a hydrogen peroxide solution containing 30% by mass in terms of $H_2O_2$ was further added, and continuously stirred for 30 minutes at 55° C. Then, the aqueous raw-material solution ($B_1$), 31.0 g of an aqueous solution of ammonium metatungstate (purity: 50%), and a dispersion liquid in which 211.5 g of silica powder was dispersed in 2.855 kg of water were sequentially added thereto, and then aged for 2.5 hours at 50° C. with stirring, thereby obtaining a slurry aqueous mixed-solution ($C_1$) as a raw material-formulated solution.

The obtained aqueous mixed-solution ($C_1$) was fed and dried in a centrifugal spray dryer, thereby obtaining a microspherical dry powder ($D_1$). The temperature at the inlet of the dryer was 210° C., and the temperature at the outlet thereof was 120° C.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.4% by mass, and the average particle size was 57 μm.

(Calcination of Dry Powder ($E_1$))

The calcination was carried out under the same calcination condition as in Example 1, except for altering the maximum calcination temperature in the pre-stage calcination to 370° C. and the maximum calcination temperature in the main calcination to 680° C. The reduction index of the pre-stage calcined product at this time was 9.0%, and the specific surface area of the calcined product after the main calcination was 11.0 $m^2/g$.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.200}Sb_{0.245}Nb_{0.082}W_{0.030}Ce_{0.005}O_n/51.0$ wt %-$SiO_2$.

(Ammoxidation Reaction of Propane)

The reaction was carried out under the same condition as in Example 1; and the propane conversion after the reaction was 84.2%, and the yield of acrylonitrile was 49.5%. The reaction was carried out continuously for 30 days using the catalyst, and the yield of acrylonitrile was 44.0%.

Comparative Example 8

(Preparation of Dry Powder)

A dry powder ($D_1$) was produced as follows.

459.2 g of ammonium heptamolybdate [$(NH_4)_6Mo_7O_{24}\cdot 4H_2O$], 63.7 g of ammonium metavanadate [$NH_4VO_3$], 80.8 g of diantimony trioxide [$Sb_2O_3$], and further 4.8 g of cerium nitrate [$Ce(NO_3)_3\cdot 6H_2O$] were added to 1.655 kg of water, and heated under stirring for one hour at 95° C., thereby preparing an aqueous raw-material solution ($A_1$).

71.5 g of a hydrogen peroxide solution containing 30% by mass in terms of $H_2O_2$ was added to 408.1 g of a niobium mixed-solution ($B_0$) prepared in the same manner as in Example 1, and was stirred and mixed for 10 minutes at room temperature, thereby preparing an aqueous raw-material solution ($B_1$).

The obtained aqueous raw-material solution ($A_1$) was cooled to 70° C., and 807.8 g of silica sol containing 34.0% by mass in terms of $SiO_2$ was thereafter added; 98.4 g of a hydrogen peroxide solution containing 30% by mass in terms of $H_2O_2$ was further added, and continuously stirred for 30 minutes at 55° C. Then, the aqueous raw-material solution ($B_1$), 31.0 g of an aqueous solution of ammonium metatungstate (purity: 50%), and a dispersion liquid in which 211.5 g of silica powder was dispersed in 2.855 kg of water were sequentially added thereto, and then aged for 2.5 hours at 50° C. with stirring, thereby obtaining a slurry aqueous mixed-solution ($C_1$) as a raw material-formulated solution.

The obtained aqueous mixed-solution ($C_1$) was fed and dried in a centrifugal spray dryer, thereby obtaining a microspherical dry powder ($D_1$). The temperature at the inlet of the dryer was 210° C., and the temperature at the outlet thereof was 120° C.

(Classification Operation)

The obtained dry powder ($D_1$) was classified using a sieve having a sieve opening of 25 μm to obtain a dry powder ($E_1$) being a classified product. The content of particles of 25 μm or smaller of the obtained dry powder ($E_1$) was 0.4% by mass, and the average particle size was 58 μm.

(Calcination of Dry Powder ($E_1$))

The calcination was carried out under the same calcination condition as in Example 1, except for altering the maximum calcination temperature in the pre-stage calcination to 370° C. and the maximum calcination temperature in the main calcination to 680° C. The reduction index of the pre-stage calcined product at this time was 10.5%, and the specific surface area of the calcined product after the main calcination was 13.8 $m^2/g$.

(Removal of Protrusions)

Protrusions were removed under the same condition as in Example 1, and the compositional ratios of a/b and a/c of the composite oxide catalyst ($G_1$) were measured by the fluorescent X-ray analysis. The results acquired are shown in Table 1. The composition of the composite oxide catalyst ($G_1$) obtained at this time was $Mo_1V_{0.220}Sb_{0.210}Nb_{0.110}W_{0.030}Ce_{0.005}O_n/51.0$ wt %-$SiO_2$.

(Ammoxidation Reaction of Propane)

The reaction was carried out under the same condition as in Example 1; and the propane conversion after the reaction was 84.3%, and the yield of acrylonitrile was 49.5%.

TABLE 1

| | Catalyst composition after removal of protrusions (a/b, a/c) | | AN yield (%) | AN yield after 30 days (%) |
|---|---|---|---|---|
| | a/b | a/c | | |
| Example 1 | 0.95 | 2.03 | 55.5 | 55.4 |
| Example 2 | 0.95 | 2.03 | 54.5 | — |
| Example 3 | 0.95 | 2.03 | 55.1 | — |
| Example 4 | 0.96 | 2.00 | 55.2 | — |
| Example 5 | 0.95 | 2.03 | 55.1 | — |
| Example 6 | 0.95 | 2.03 | 55.1 | — |
| Example 7 | 0.95 | 2.03 | 55.1 | — |
| Example 8 | 0.95 | 2.03 | 55.1 | — |
| Example 9 | 0.95 | 2.03 | 54.0 | — |
| Example 10 | 0.95 | 2.03 | 54.2 | — |
| Example 11 | 0.95 | 2.03 | 54.9 | — |
| Example 12 | 0.95 | 2.03 | 54.6 | — |
| Example 13 | 0.95 | 2.03 | 55.2 | — |
| Example 14 | 0.95 | 2.03 | 54.3 | — |
| Example 15 | 0.95 | 2.03 | 55.0 | 55.3 |
| Example 16 | 0.95 | 2.03 | 55.2 | — |
| Example 17 | 0.95 | 2.03 | 55.2 | — |
| Example 18 | 0.95 | 2.03 | 54.4 | — |
| Example 19 | 0.95 | 2.03 | 54.3 | — |
| Example 20 | 0.95 | 2.03 | 54.6 | — |
| Example 21 | 0.95 | 2.03 | 54.0 | — |
| Example 22 | 0.95 | 2.03 | 54.1 | — |
| Example 23 | 0.95 | 2.03 | 54.1 | — |
| Example 24 | 0.85 | 1.70 | 54.8 | — |
| Example 25 | 0.85 | 2.24 | 54.6 | — |
| Example 26 | 0.99 | 2.27 | 54.5 | — |
| Example 27 | 0.98 | 1.73 | 55.5 | — |
| Example 28 | 0.98 | 1.48 | 54.6 | — |
| Example 29 | 0.85 | 1.48 | 54.4 | — |
| Example 30 | 0.88 | 2.17 | 55.1 | — |
| Example 31 | 0.88 | 1.74 | 55.2 | — |
| Example 32 | 0.95 | 2.03 | 53.8 | — |
| Example 33 | 0.95 | 1.53 | 54.4 | 54.6 |
| Example 34 | 0.92 | 1.71 | 52.8 | 54.8 |
| Example 35 | 0.95 | 2.25 | 55.4 | 54.5 |

TABLE 1-continued

| | Catalyst composition after removal of protrusions (a/b, a/c) | | AN yield (%) | AN yield after 30 days (%) |
|---|---|---|---|---|
| | a/b | a/c | | |
| Comparative Example 1 | 0.75 | 2.10 | 51.5 | 49.0 |
| Comparative Example 2 | 1.05 | 2.56 | 52.3 | — |
| Comparative Example 3 | 0.88 | 2.56 | 52.0 | — |
| Comparative Example 4 | 0.77 | 1.43 | 51.5 | — |
| Comparative Example 5 | 0.95 | 1.34 | 48.5 | 46.5 |
| Comparative Example 6 | 1.06 | 1.59 | 51.6 | — |
| Comparative Example 7 | 0.82 | 2.44 | 49.5 | 44.0 |
| Comparative Example 8 | 1.05 | 2.00 | 49.5 | — |

INDUSTRIAL APPLICABILITY

The present invention has the industrial applicability as a composite oxide catalyst used in a vapor-phase catalytic oxidation or a vapor-phase catalytic ammoxidation reaction of propane or isobutane.

DESCRIPTION OF SYMBOLS

1: MAIN BODY
2: GAS INLET PIPE, 21: BRANCH PIPE, 210: NOZZLE, 211: OPENING, 22: SUBBRANCH, 220: OPENING
3: OUTLET PIPE, 31: OUTER PIPE, 32: INNER PIPE, 33: NOZZLE
4: CYCLON, 41: OUTLET PIPE, 42: CYCLON
5, 51, 52: RETURN PIPE, 53: OUTER PIPE, 54: INNER PIPE, 55: NOZZLE
6: NOZZLE, 61: NOZZLE FRONT END
7: GAS INLET PIPE, 71: CIRCULATION LINE
8: DISCHARGE LINE
11: OUTER TUBE
12: INNER TUBE
13: OPENING

What is claimed is:

1. A complex oxide catalyst used for a vapor-phase catalytic oxidation reaction or vapor-phase catalytic ammoxidation reaction of propane or isobutane, the catalyst comprising a complex oxide represented by the following formula (1):

$$Mo_1V_aSb_bNb_cW_dZ_eO_n \qquad (1)$$

wherein a component Z represents Ce and optionally one or more elements selected from La, Pr, Yb, Y, Sc, Sr, and Ba; a, b, c, d, e, and n each represent an atomic ratio of an element to one Mo atom; $0.1 \le a \le 0.24$, $0.1 \le b \le 0.258$, $0.01 \le c \le 0.3$, $0 \le d \le 0.2$, and $0 \le e \le 0.1$; an atomic ratio a/b is $0.85 \le a/b < 1.0$, and an atomic ratio a/c is $1.4 < a/c < 2.27$, and wherein an amount of protrusions is not more than 2% by mass based on a total mass of the complex oxide catalyst.

2. The complex oxide catalyst according to claim 1, comprising 20 to 70% by mass of silica in terms of $SiO_2$.

3. A method for producing a complex oxide catalyst comprising a complex oxide represented by the following formula (1):

$$Mo_1V_aSb_bNb_cW_dZ_eO_n \qquad (1)$$

(wherein a component Z represents one or more elements selected from La, Ce, Pr, Yb, Y, Sc, Sr, and Ba; a, b, c, d, e, and n each represent an atomic ratio of an element to one Mo atom; $0.1 \le a \le 0.4$, $0.1 \le b \le 0.4$, $0.01 \le c \le 0.3$, $0 \le d \le 0.2$, and $0 \leq e \leq 0.1$; an atomic ratio a/b is $0.85 \leq a/b < 1.0$, and an atomic ratio a/c is $1.4 < a/c < 2.3$), the method comprising the steps (I) to (V):

(I) preparing a raw material-formulated solution comprising Mo, V, Sb, Nb, W, and Z, wherein an atomic ratio a of V to one Mo atom is $0.1 \leq a \leq 0.5$, an atomic ratio b of Sb to one Mo atom is $0.1 \leq b \leq 0.5$, an atomic ratio c of Nb to one Mo atom is $0.01 \leq c \leq 0.5$, an atomic ratio d of W to one Mo atom is $0 \leq d \leq 0.4$, and an atomic ratio e of Z to one Mo atom is $0 \leq e \leq 0.2$;

(II) drying the raw material-formulated solution to obtain a dry powder;

(III) pre-stage calcining the dry powder to obtain a pre-stage calcined product;

(IV) main-calcining the pre-stage calcined product to obtain a calcined product having a protrusion on a surface of a particle; and (V) removing the protrusion existing on the surface of the particle of the calcined product by an air stream, wherein a reduction rate of the pre-stage calcined product is 8 to 12%, and a specific surface area of the calcined product is 7 to 20 $m^2/g$.

4. The method for producing a complex oxide catalyst according to claim 3, wherein a content of particles having a particle size of not more than 25 μm in the dry powder is not more than 20% by mass, and an average particle size of the dry powder is 35 to 75 μm.

5. The method for producing a complex oxide catalyst according to claim 3, wherein in the step (V), the protrusion is removed so that the amount of the protrusion that the calcined product has is not more than 2% by mass based on a total mass of the calcined product.

6. The method for producing a complex oxide catalyst according to claim 3, wherein a length of the air stream in a direction of the air stream flowing is not less than 55 mm, and an average flow rate of the air stream is not less than 80 m/s and not more than 500 m/s as a linear velocity at 15° C. and 1 atmospheric pressure.

7. The method for producing a complex oxide catalyst according to claim 3, wherein the step (I) comprises the steps (a) to (d):

(a) preparing an aqueous mixed-solution comprising Mo, V, Sb, and the component Z;

(b) adding silica sol and a hydrogen peroxide solution to the aqueous mixed-solution obtained in the step (a);

(c) mixing an aqueous solution comprising Nb, dicarboxylic acid, and the hydrogen peroxide solution and a W compound with the solution obtained in the step (b); and (d) adding a powder silica-containing suspension to the solution obtained in the step (c) and aging the solution.

8. The method for producing a complex oxide catalyst according to claim 3, wherein the (III) pre-stage calcination step and/or the (IV) main calcination step comprises the steps (i) and (ii):

(i) giving impact to a calcining apparatus in which the pre-stage calcined product and/or the calcined product is calcined; and (ii) annealing the pre-stage calcined product and/or the calcined product at a temperature lower than the calcining temperature in the main calcination.

9. A method for producing an unsaturated acid using the complex oxide catalyst according to claim 1, wherein propane or isobutane is subjected to a vapor-phase catalytic oxidation reaction to produce a corresponding unsaturated acid.

10. A method for producing an unsaturated nitrile using the complex oxide catalyst according to claim 1, wherein propane or isobutane is subjected to a vapor-phase catalytic ammoxidation reaction to produce a corresponding unsaturated nitrile.

11. The method for producing a complex oxide catalyst according to claim 4, wherein in the step (V), the protrusion is removed so that the amount of the protrusion that the calcined product has is not more than 2% by mass based on a total mass of the calcined product.

12. The method for producing a complex oxide catalyst according to claim 4, wherein a length of the air stream in a direction of the air stream flowing is not less than 55 mm, and an average flow rate of the air stream is not less than 80 m/s and not more than 500 m/s as a linear velocity at 15° C. and 1 atmospheric pressure.

13. The method for producing a complex oxide catalyst according to claim 5, wherein a length of the air stream in a direction of the air stream flowing is not less than 55 mm, and an average flow rate of the air stream is not less than 80 m/s and not more than 500 m/s as a linear velocity at 15° C. and 1 atmospheric pressure.

14. The method for producing a complex oxide catalyst according to claim 4, wherein the step (I) comprises the steps (a) to (d):

(a) preparing an aqueous mixed-solution comprising Mo, V, Sb, and the component Z;

(b) adding silica sol and a hydrogen peroxide solution to the aqueous mixed-solution obtained in the step (a);

(c) mixing an aqueous solution comprising Nb, dicarboxylic acid, and the hydrogen peroxide solution and a W compound with the solution obtained in the step (b); and (d) adding a powder silica-containing suspension to the solution obtained in the step (c) and aging the solution.

15. The method for producing a complex oxide catalyst according to claim 5, wherein the step (I) comprises the steps (a) to (d):

(a) preparing an aqueous mixed-solution comprising Mo, V, Sb, and the component Z;

(b) adding silica sol and a hydrogen peroxide solution to the aqueous mixed-solution obtained in the step (a);

(c) mixing an aqueous solution comprising Nb, dicarboxylic acid, and the hydrogen peroxide solution and a W compound with the solution obtained in the step (b); and (d) adding a powder silica-containing suspension to the solution obtained in the step (c) and aging the solution.

16. The method for producing a complex oxide catalyst according to claim 6, wherein the step (I) comprises the steps (a) to (d):

(a) preparing an aqueous mixed-solution comprising Mo, V, Sb, and the component Z;

(b) adding silica sol and a hydrogen peroxide solution to the aqueous mixed-solution obtained in the step (a);

(c) mixing an aqueous solution comprising Nb, dicarboxylic acid, and the hydrogen peroxide solution and a W compound with the solution obtained in the step (b); and (d) adding a powder silica-containing suspension to the solution obtained in the step (c) and aging the solution.

17. The method for producing a complex oxide catalyst according to claim 4, wherein the (III) pre-stage calcination step and/or the (IV) main calcination step comprises the steps (i) and (ii):

(i) giving impact to a calcining apparatus in which the pre-stage calcined product and/or the calcined product is calcined; and (ii) annealing the pre-stage calcined product and/or the calcined product at a temperature lower than the calcining temperature in the main calcination.

18. The method for producing a complex oxide catalyst according to claim 5, wherein the (III) pre-stage calcination step and/or the (IV) main calcination step comprises the steps (i) and (ii):

(i) giving impact to a calcining apparatus in which the pre-stage calcined product and/or the calcined product is calcined; and (ii) annealing the pre-stage calcined product and/or the calcined product at a temperature lower than the calcining temperature in the main calcination.

19. The method for producing a complex oxide catalyst according to claim 6, wherein the (III) pre-stage calcination step and/or the (IV) main calcination step comprises the steps (i) and (ii):

(i) giving impact to a calcining apparatus in which the pre-stage calcined product and/or the calcined product is calcined; and (ii) annealing the pre-stage calcined product and/or the calcined product at a temperature lower than the calcining temperature in the main calcination.

20. The method for producing a complex oxide catalyst according to claim 7, wherein the (III) pre-stage calcination step and/or the (IV) main calcination step comprises the steps (i) and (ii):

(i) giving impact to a calcining apparatus in which the pre-stage calcined product and/or the calcined product is calcined; and (ii) annealing the pre-stage calcined product and/or the calcined product at a temperature lower than the calcining temperature in the main calcination.

21. A method for producing an unsaturated acid using the complex oxide catalyst according to claim 2, wherein propane or isobutane is subjected to a vapor-phase catalytic oxidation reaction to produce a corresponding unsaturated acid.

22. A method for producing an unsaturated nitrile using the complex oxide catalyst according to claim 2, wherein propane or isobutane is subjected to a vapor-phase catalytic ammoxidation reaction to produce a corresponding unsaturated nitrile.

* * * * *